US012714478B2

(12) United States Patent
Hua et al.

(10) Patent No.: US 12,714,478 B2
(45) Date of Patent: Aug. 25, 2026

(54) SYSTEMS AND METHODS FOR PEDICLE SCREW STABILIZATION OF SPINAL VERTEBRAE

(71) Applicant: SPINE23 INC., Campbell, CA (US)

(72) Inventors: Sherwin Hua, Hillsborough, CA (US); Andrew Huffmaster, Fremont, CA (US)

(73) Assignee: SPINE23 INC., Campbell, CA (US)

(*) Notice: Subject to any disclaimer, the term of this patent is extended or adjusted under 35 U.S.C. 154(b) by 0 days.

(21) Appl. No.: 18/919,351

(22) Filed: Oct. 17, 2024

(65) Prior Publication Data

US 2025/0120750 A1 Apr. 17, 2025

Related U.S. Application Data

(60) Provisional application No. 63/591,099, filed on Oct. 17, 2023.

(51) Int. Cl.
*A61B 17/70* (2006.01)

(52) U.S. Cl.
CPC ...... *A61B 17/7083* (2013.01); *A61B 17/7032* (2013.01); *A61B 17/7082* (2013.01); *A61B 17/7085* (2013.01)

(58) Field of Classification Search
CPC ............ A61B 17/7083; A61B 17/7085; A61B 17/7089
See application file for complete search history.

(56) References Cited

U.S. PATENT DOCUMENTS

| | | |
|---|---|---|
| 4,448,191 A | 5/1984 | Rodnyansky et al. |
| 5,092,866 A | 3/1992 | Breard et al. |
| 5,242,443 A | 9/1993 | Kambin |

(Continued)

FOREIGN PATENT DOCUMENTS

| | | |
|---|---|---|
| CN | 2782035 Y | 5/2006 |
| CN | 1972639 A | 5/2007 |

(Continued)

OTHER PUBLICATIONS

"MANTIS™ Spinal System Surgical Technique", Stryker Spine, Literature No. TLMANST06071, 2006, (Brochure) in 48 pages.

(Continued)

*Primary Examiner* — Nicholas W Woodall
(74) *Attorney, Agent, or Firm* — Knobbe, Martens, Olson & Bear, LLP

(57) ABSTRACT

Disclosed herein are embodiments of a system and embodiments of a method for stabilizing spinal vertebrae through a skin incision. In some embodiments, the system or method can include a first screw having a first screw head, a second screw having a second screw head, and/or a third screw having a third screw head, a first tower having a distal portion, a proximal portion, and a bend between the distal portion and the proximal portion, a second tower having a distal portion, a proximal portion, and a bend between the distal portion and the proximal portion, a third tower having a distal portion and a proximal portion, the third tower configured to be removably coupled with the third screw at a distal end of the third tower, and a rod insertion device configured to rotatably advance a connection element to at least the first and second towers.

19 Claims, 34 Drawing Sheets

(56) References Cited

U.S. PATENT DOCUMENTS 5,300,076 A 4/1994 Leriche
5,306,275 A 4/1994 Bryan
5,324,316 A 6/1994 Schulman et al.
5,411,546 A 5/1995 Bowald et al.
5,531,779 A 7/1996 Dahl et al.
5,672,175 A 9/1997 Martin
5,728,097 A 3/1998 Mathews
5,865,842 A 2/1999 Knuth et al.
5,938,689 A 8/1999 Fischell et al.
5,975,085 A 11/1999 Rise
5,980,521 A 11/1999 Montague et al.
6,011,991 A 1/2000 Mardirossian
6,016,449 A 1/2000 Fischell et al.
6,051,017 A 4/2000 Loeb et al.
6,090,113 A 7/2000 Le Couedic et al.
6,175,764 B1 1/2001 Loeb et al.
6,176,242 B1 1/2001 Rise
6,181,965 B1 1/2001 Loeb et al.
6,185,452 B1 2/2001 Schulman et al.
6,208,881 B1 3/2001 Champeau
6,208,894 B1 3/2001 Schulman et al.
6,214,016 B1 4/2001 Williams et al.
6,227,203 B1 5/2001 Rise et al.
6,235,028 B1 5/2001 Brumfield et al.
6,240,316 B1 5/2001 Richmond et al.
6,263,237 B1 7/2001 Rise
6,343,226 B1 1/2002 Sunde et al.
6,427,086 B1 7/2002 Fischell et al.
6,445,953 B1 9/2002 Bulkes et al.
6,482,182 B1 11/2002 Carroll et al.
6,485,491 B1 11/2002 Farris et al.
6,493,592 B1 12/2002 Leonard et al.
6,530,929 B1 3/2003 Justis et al.
6,546,277 B1 4/2003 Franck et al.
6,549,810 B1 4/2003 Leonard et al.
6,582,441 B1 6/2003 He et al.
6,597,954 B1 7/2003 Pless et al.
6,622,051 B1 9/2003 Bishay et al.
6,623,490 B1 9/2003 Crane et al.
6,665,562 B2 12/2003 Gluckman
6,711,430 B1 3/2004 Ferris et al.
6,731,976 B2 5/2004 Penn et al.
6,735,475 B1 5/2004 Whitehurst et al.
6,764,498 B2 7/2004 Mische
6,782,292 B2 8/2004 Whitehurst
6,788,975 B1 9/2004 Whitehurst et al.
6,793,656 B1 9/2004 Mathews
6,795,737 B2 9/2004 Gielen et al.
6,819,956 B2 11/2004 Dilorenzo
6,830,544 B2 12/2004 Tanner
6,862,479 B1 3/2005 Whitehurst et al.
6,871,098 B2 3/2005 Nuttin
6,916,320 B2 7/2005 Michelson
6,922,590 B1 7/2005 Whitehurst
6,929,606 B2 8/2005 Ritland
6,950,707 B2 9/2005 Whitehurst
6,959,215 B2 10/2005 Gliner et al.
6,970,741 B1 11/2005 Whitehurst et al.
6,978,180 B2 12/2005 Tadlock
6,990,377 B2 1/2006 Gliner et al.
7,003,352 B1 2/2006 Whitehurst
7,006,859 B1 2/2006 Osorio et al.
7,008,422 B2 3/2006 Foley et al.
7,011,660 B2 3/2006 Sherman et al.
7,013,177 B1 3/2006 Whitehurst et al.
7,063,708 B2 6/2006 Gibson et al.
7,063,725 B2 6/2006 Foley
7,066,961 B2 6/2006 Michelson
7,083,621 B2 8/2006 Shaolian et al.
7,103,408 B2 9/2006 Haller et al.
7,107,103 B2 9/2006 Schulman et al.
7,146,217 B2 12/2006 Firlik et al.
7,150,737 B2 12/2006 Purdy et al.
7,151,961 B1 12/2006 Whitehurst et al.
7,158,333 B1 1/2007 Sut ardja et al.
7,167,751 B1 1/2007 Whitehurst et al.
7,174,212 B1 2/2007 Klehn et al.
7,179,225 B2 2/2007 Shluzs et al.
7,179,261 B2 2/2007 Seivol et al.
7,187,967 B2 3/2007 Kennedy
7,188,626 B2 3/2007 Foley et al.
7,209,787 B2 4/2007 Dilorenzo
7,221,981 B2 5/2007 Gliner
7,236,830 B2 6/2007 Gliner
7,236,831 B2 6/2007 Firlik et al.
7,250,052 B2 7/2007 Landry et al.
7,255,686 B2 8/2007 Putz
7,277,758 B2 10/2007 DiLorenzo
7,282,064 B2 10/2007 Chin
7,283,856 B2 10/2007 Boling
7,292,890 B2 11/2007 Whitehurst et al.
7,295,875 B2 11/2007 Wallace et al.
7,299,096 B2 11/2007 Balzer et al.
7,302,298 B2 11/2007 Lowry et al.
7,305,268 B2 12/2007 Gliner et al.
7,306,603 B2 12/2007 Boehm, Jr. et al.
7,326,210 B2 2/2008 Jahng et al.
D565,735 S 4/2008 Washbon
7,353,064 B2 4/2008 Gliner et al.
7,376,468 B2 5/2008 King et al.
7,386,350 B2 6/2008 Villims
7,406,105 B2 7/2008 Delmain et al.
7,440,806 B1 10/2008 Whitehurst et al.
7,465,306 B2 12/2008 Pond, Jr. et al.
7,468,064 B2 12/2008 Bruneau et al.
7,491,208 B2 2/2009 Pond, Jr. et al.
7,491,218 B2 2/2009 Landry et al.
7,493,171 B1 2/2009 Whitehurst et al.
7,497,869 B2 3/2009 Justis
7,515,961 B2 4/2009 Germanson et al.
7,520,879 B2 4/2009 Justis et al.
7,527,638 B2 5/2009 Anderson et al.
7,547,318 B2 6/2009 Birkmeyer et al.
7,575,581 B2 8/2009 Lovell
7,588,575 B2 9/2009 Colleran et al.
7,588,588 B2 9/2009 Spitler et al.
7,604,658 B2 10/2009 Wilson et al.
7,666,189 B2 2/2010 Gerber et al.
7,684,867 B2 3/2010 Jaax et al.
7,686,814 B2 3/2010 Lim et al.
7,691,132 B2 4/2010 Landry et al.
7,708,763 B2 5/2010 Selover et al.
7,717,944 B2 5/2010 Foley et al.
7,725,196 B2 5/2010 Machado et al.
7,736,370 B2 6/2010 Sweeney
7,749,233 B2 7/2010 Farr et al.
7,758,584 B2 7/2010 Bankoski et al.
7,758,617 B2 7/2010 Iott et al.
7,763,055 B2 7/2010 Foley
7,776,051 B2 8/2010 Colleran et al.
7,824,410 B2 11/2010 Simonson et al.
7,846,093 B2 12/2010 Gorek et al.
7,875,031 B2 1/2011 Chin et al.
7,894,912 B2 2/2011 Benabid et al.
7,917,230 B2 3/2011 Bly
7,937,160 B2 5/2011 Garabedian et al.
7,947,045 B2 5/2011 Hestad et al.
7,955,355 B2 6/2011 Chin
7,974,696 B1 7/2011 DiLorenzo
7,991,465 B2 8/2011 Bartic et al.
8,000,795 B2 8/2011 Lozano
8,043,343 B2 10/2011 Miller et al.
8,052,711 B2 11/2011 Hanse et al.
8,052,720 B2 11/2011 Kuester et al.
8,060,207 B2 11/2011 Wallace et al.
8,075,565 B2 12/2011 Wilcox et al.
8,100,959 B2 1/2012 Que et al.
8,103,350 B2 1/2012 Wallace et al.
8,150,524 B2 4/2012 Maschino et al.
8,209,027 B2 6/2012 Butson et al.
8,216,173 B2 7/2012 Dacey, Jr. et al.
8,216,282 B2 7/2012 Hua
8,282,593 B2 10/2012 Dacey, Jr. et al.
8,333,753 B2 12/2012 Nishtala

(56) References Cited

U.S. PATENT DOCUMENTS 8,333,770 B2 12/2012 Hua
8,343,086 B2 1/2013 Dacey, Jr. et al.
8,346,365 B2 1/2013 Lozano
8,366,652 B2 2/2013 Dacey, Jr. et al.
8,366,714 B2 2/2013 Jones et al.
8,401,654 B1 3/2013 Foster et al.
8,417,345 B2 4/2013 Machado et al.
8,460,313 B2 6/2013 Huffmaster
8,515,541 B1 8/2013 Jaax et al.
8,515,542 B2 8/2013 Jaax et al.
8,545,541 B2 10/2013 Hua
8,556,940 B2 10/2013 Hua
8,706,181 B2 4/2014 Stypulkowski et al.
8,721,691 B2 5/2014 Hua
8,731,674 B2 5/2014 Wallace
8,798,754 B2 8/2014 Knudson et al.
8,900,248 B2 * 12/2014 Biyani ............... A61B 17/7002 606/104
9,179,875 B2 11/2015 Hua
9,198,698 B1 12/2015 Doose et al.
9,307,925 B2 4/2016 Russell et al.
9,327,069 B2 5/2016 Foster et al.
9,352,145 B2 5/2016 Whitehurst et al.
9,402,659 B2 * 8/2016 McBride ............ A61B 17/7077
9,402,661 B2 8/2016 Reitblat et al.
9,421,373 B2 8/2016 DiLorenzo
9,480,574 B2 11/2016 Lee et al.
9,630,019 B2 4/2017 Valente et al.
9,636,115 B2 5/2017 Henry et al.
9,642,552 B2 5/2017 Hua
9,724,515 B2 8/2017 Fostick et al.
9,820,668 B2 11/2017 Hua
9,867,978 B1 1/2018 Rapoport et al.
9,877,846 B2 1/2018 Dvorak et al.
9,919,146 B2 3/2018 Hua
9,919,148 B2 3/2018 Howard et al.
9,925,376 B2 3/2018 Hartig et al.
9,955,961 B2 5/2018 Huffmaster et al.
10,004,543 B2 6/2018 Stokes et al.
10,194,960 B1 2/2019 Hammann et al.
10,406,351 B2 9/2019 Hua
10,660,631 B1 5/2020 Boesel et al.
10,702,314 B2 7/2020 Reitblat et al.
10,736,533 B2 8/2020 Hua
10,973,551 B2 4/2021 Hua
11,116,509 B2 9/2021 Follmer et al.
11,160,580 B2 11/2021 Hua
11,759,238 B2 9/2023 Hua
12,076,058 B2 9/2024 Hua et al.
12,268,422 B2 4/2025 Hua
2001/0003156 A1 6/2001 Gill
2002/0151770 A1 10/2002 Nol, III et al.
2003/0028072 A1 2/2003 Fischell et al.
2003/0040753 A1 2/2003 Daum et al.
2003/0088245 A1 5/2003 Woloszko et al.
2003/0093105 A1 5/2003 Huffmaster
2003/0093129 A1 5/2003 Nicolelis et al.
2003/0135147 A1 7/2003 Rosenberg et al.
2003/0171750 A1 9/2003 Chin
2003/0208203 A1 11/2003 Lim et al.
2003/0233125 A1 12/2003 Kaplan et al.
2003/0233126 A1 12/2003 Kaplan et al.
2004/0030236 A1 2/2004 Mazzochi et al.
2004/0082961 A1 4/2004 Teitelbaum
2004/0088024 A1 5/2004 Firlik et al.
2004/0147928 A1 7/2004 Landry et al.
2004/0186532 A1 9/2004 Tadlock
2004/0225335 A1 11/2004 Whitehurst et al.
2004/0243130 A1 12/2004 Biscup
2004/0243207 A1 12/2004 Olson et al.
2004/0267274 A1 12/2004 Patel et al.
2005/0021040 A1 1/2005 Bertagnoli
2005/0049649 A1 3/2005 Luders et al.
2005/0075680 A1 4/2005 Lowry et al.
2005/0101954 A1 5/2005 Simonson
2005/0102006 A1 5/2005 Whitehurst et al.
2005/0131311 A1 6/2005 Leuthardt et al.
2005/0131422 A1 6/2005 Anderson et al.
2005/0137646 A1 6/2005 Wallace et al.
2005/0137652 A1 6/2005 Cauller et al.
2005/0182453 A1 8/2005 Whitehurst et al.
2005/0192570 A1 9/2005 Jackson
2005/0192589 A1 9/2005 Raymond et al.
2005/0203599 A1 9/2005 Garabedian et al.
2005/0228380 A1 10/2005 Moore et al.
2005/0245969 A1 11/2005 Loeb
2005/0251237 A1 11/2005 Kuzma et al.
2005/0267491 A1 12/2005 Kellett et al.
2005/0283203 A1 12/2005 Flaherty et al.
2006/0005845 A1 1/2006 Karr et al.
2006/0025841 A1 2/2006 McIntyre
2006/0030872 A1 2/2006 Culbert et al.
2006/0058854 A1 3/2006 Abrams et al.
2006/0089652 A1 4/2006 Eckman
2006/0095035 A1 5/2006 Jones et al.
2006/0111767 A1 5/2006 Olson et al.
2006/0122597 A1 6/2006 Jones et al.
2006/0173522 A1 8/2006 Osorio
2006/0184143 A1 8/2006 Jolly et al.
2006/0195154 A1 8/2006 Jaax et al.
2006/0206165 A1 9/2006 Jaax et al.
2006/0212087 A1 9/2006 Haller et al.
2006/0212090 A1 9/2006 Lozano et al.
2006/0212091 A1 9/2006 Lozano et al.
2006/0234279 A1 10/2006 Miller et al.
2006/0235279 A1 10/2006 Hawkes et al.
2006/0241600 A1 10/2006 Ensign et al.
2006/0241717 A1 10/2006 Whitehurst et al.
2006/0264942 A1 11/2006 Lim et al.
2006/0264962 A1 11/2006 Chin et al.
2007/0016188 A1 1/2007 Boehm, Jr. et al.
2007/0016198 A1 1/2007 Boehm, Jr. et al.
2007/0016199 A1 1/2007 Boehm, Jr. et al.
2007/0021800 A1 1/2007 Whitehurst et al.
2007/0027498 A1 2/2007 Maschino et al.
2007/0032718 A1 2/2007 Shults et al.
2007/0032839 A1 2/2007 Parramon et al.
2007/0060974 A1 3/2007 Lozano
2007/0078460 A1 4/2007 Frigg et al.
2007/0078503 A1 4/2007 Kuzma et al.
2007/0088417 A1 4/2007 Schouenborg
2007/0093814 A1 4/2007 Callahan, II et al.
2007/0100393 A1 5/2007 Whitehurst et al.
2007/0106143 A1 5/2007 Flaherty
2007/0123954 A1 5/2007 Gielen et al.
2007/0135867 A1 6/2007 Klosterman et al.
2007/0167954 A1 7/2007 Sicvol et al.
2007/0173733 A1 7/2007 Le et al.
2007/0191840 A1 8/2007 Pond, Jr. et al.
2007/0219554 A1 9/2007 Landry et al.
2007/0219854 A1 9/2007 Mueller et al.
2007/0233079 A1 10/2007 Fallin et al.
2007/0233097 A1 10/2007 Anderson et al.
2007/0233158 A1 10/2007 Rodriguez
2007/0239159 A1 10/2007 Altarac et al.
2007/0239259 A1 10/2007 Boylan et al.
2007/0265582 A1 11/2007 Kaplan et al.
2007/0265683 A1 11/2007 Ehrlich
2007/0270815 A1 11/2007 Johnson et al.
2007/0282395 A1 12/2007 Maltan et al.
2007/0282396 A1 12/2007 Overstreet et al.
2007/0299443 A1 12/2007 DiPoto et al.
2007/0299444 A1 12/2007 DiPoto et al.
2008/0004676 A1 1/2008 Osypka et al.
2008/0009864 A1 1/2008 Forton et al.
2008/0009920 A1 1/2008 Gibson et al.
2008/0015582 A1 1/2008 DiPoto et al.
2008/0039838 A1 2/2008 Landry et al.
2008/0045957 A1 2/2008 Landry et al.
2008/0046012 A1 2/2008 Covalin et al.
2008/0051782 A1 * 2/2008 Wu .................... A61B 17/7089 606/250
2008/0071274 A1 3/2008 Ensign
2008/0071323 A1 3/2008 Lowry et al.

(56) References Cited

U.S. PATENT DOCUMENTS

2008/0077139 A1 3/2008 Landry et al.
2008/0086130 A1 4/2008 Lake et al.
2008/0097457 A1 4/2008 Warnick
2008/0097519 A1 4/2008 Calderon et al.
2008/0119849 A1 5/2008 Beardsley et al.
2008/0119850 A1 5/2008 Sicvol et al.
2008/0119862 A1 5/2008 Wicker et al.
2008/0125788 A1 5/2008 Cohen et al.
2008/0125817 A1 5/2008 Arnett et al.
2008/0140075 A1 6/2008 Ensign et al.
2008/0140120 A1 6/2008 Hestad et al.
2008/0140132 A1 6/2008 Perez-Cruet
2008/0140154 A1 6/2008 Loeb et al.
2008/0177269 A1 7/2008 Seelig
2008/0183241 A1 7/2008 Bedenbaugh
2008/0208074 A1 8/2008 Snyder et al.
2008/0208302 A1 8/2008 Alexander et al.
2008/0218472 A1 9/2008 Breen et al.
2008/0221582 A1 9/2008 Gia et al.
2008/0249531 A1* 10/2008 Patterson ........... A61B 17/7089 606/300
2008/0262318 A1 10/2008 Gorek et al.
2008/0312716 A1 12/2008 Russell
2009/0018599 A1 1/2009 Hastings et al.
2009/0054955 A1 2/2009 Kopell et al.
2009/0062857 A1* 3/2009 Ramsay ............. A61B 17/7085 606/279
2009/0082819 A1 3/2009 Blain et al.
2009/0112278 A1 4/2009 Wingeier et al.
2009/0118804 A1 5/2009 Moffitt et al.
2009/0125080 A1 5/2009 Montgomery
2009/0171392 A1 7/2009 Garcia-Bengochea et al.
2009/0187220 A1 7/2009 Hamada
2009/0216278 A1 8/2009 Song
2009/0221878 A1 9/2009 Gorek
2009/0221879 A1 9/2009 Gorek
2009/0222044 A1 9/2009 Gorek
2009/0222045 A1 9/2009 Gorek
2009/0222046 A1 9/2009 Gorek
2009/0234392 A1 9/2009 Dziedzic et al.
2009/0259137 A1 10/2009 Delic et al.
2009/0287061 A1 11/2009 Feigenbaum et al.
2009/0326586 A1* 12/2009 Duarte ............... A61B 17/7089 606/279
2010/0004695 A1 1/2010 Stad et al.
2010/0049206 A1 2/2010 Biyani
2010/0145176 A1 6/2010 Himes
2010/0168803 A1 7/2010 Hestad et al.
2010/0234792 A1 9/2010 Dacey, Jr. et al.
2010/0234793 A1 9/2010 Dacey, Jr. et al.
2010/0240017 A1 9/2010 Dacey, Jr. et al.
2010/0241048 A1 9/2010 Dacey, Jr. et al.
2010/0241050 A1 9/2010 Dacey, Jr. et al.
2010/0241051 A1 9/2010 Dacey, Jr. et al.
2010/0241052 A1 9/2010 Dacey, Jr. et al.
2010/0241053 A1 9/2010 Dacey, Jr. et al.
2010/0249692 A1 9/2010 Dacey, Jr. et al.
2010/0249844 A1 9/2010 Durrani
2010/0292629 A1 11/2010 Dacey, Jr. et al.
2011/0022088 A1 1/2011 Forton et al.
2011/0077692 A1 3/2011 Jackson
2011/0112590 A1 5/2011 Wu et al.
2011/0172674 A1 7/2011 Bankoski et al.
2011/0196426 A1 8/2011 Peukert et al.
2011/0202095 A1 8/2011 Semler et al.
2011/0218560 A1 9/2011 Ramzipoor et al.
2011/0238117 A1 9/2011 Geist et al.
2011/0319938 A1 12/2011 Piza Vallespir et al.
2012/0065693 A1 3/2012 Lim et al.
2012/0089187 A1 4/2012 Forton et al.
2012/0109208 A1* 5/2012 Justis ................. A61B 17/8863 606/264
2012/0239096 A1 9/2012 Gleeson et al.
2012/0316609 A1 12/2012 Wall et al.
2013/0096637 A1* 4/2013 Richelsoph ........ A61B 17/7089 606/86 A
2013/0110184 A1 5/2013 Wing et al.
2013/0184763 A1 7/2013 McClintock et al.
2013/0289385 A1 10/2013 Lozano et al.
2013/0325069 A1 12/2013 Pereiro de Lamo et al.
2014/0039556 A1 2/2014 Rutschmann et al.
2014/0243714 A1 8/2014 Ward et al.
2014/0350612 A1 11/2014 Leroux et al.
2015/0066088 A1 3/2015 Brinkman et al.
2015/0088210 A1 3/2015 Reitblat et al.
2015/0173810 A1* 6/2015 Biedermann ...... A61B 17/7088 606/279
2015/0216568 A1 8/2015 Sanpera Trigueros et al.
2015/0230836 A1 8/2015 Cochran
2015/0374354 A1 12/2015 Boyd et al.
2016/0158051 A1 6/2016 Mische
2016/0166326 A1 6/2016 Bakker et al.
2016/0220821 A1 8/2016 O'Connell et al.
2016/0228693 A1 8/2016 Vardiman
2016/0242827 A1* 8/2016 Viljoen .............. A61B 17/7052
2016/0331410 A1 11/2016 Tsuang et al.
2016/0331971 A1 11/2016 Gill
2016/0367809 A1 12/2016 Patel et al.
2017/0056076 A1* 3/2017 Kim ................... A61B 17/7089
2017/0143966 A1 5/2017 Reymers et al.
2017/0151436 A1 6/2017 Flaherty et al.
2017/0164985 A1 6/2017 Reitblat et al.
2018/0000372 A1 1/2018 Hua
2018/0036037 A1 2/2018 Abell et al.
2018/0070987 A1 3/2018 Su et al.
2018/0303630 A1 10/2018 Lorang et al.
2018/0360514 A1 12/2018 Emery et al.
2019/0069930 A1 3/2019 Su et al.
2019/0090918 A1 3/2019 Jackson
2019/0142470 A1 5/2019 Kim et al.
2019/0183543 A1 6/2019 Hammann et al.
2019/0216453 A1 7/2019 Predick et al.
2019/0216482 A1 7/2019 Huffmaster et al.
2019/0231394 A1 8/2019 Bechtel et al.
2019/0290332 A1 9/2019 Tsuang et al.
2019/0336182 A1 11/2019 Suh et al.
2020/0107865 A1 4/2020 Lu et al.
2021/0121219 A1 4/2021 Huffmaster et al.
2021/0161569 A1* 6/2021 Shin ................... A61B 17/7089
2021/0161579 A1 6/2021 Huffmaster et al.
2022/0031922 A1 2/2022 Tsuji et al.
2022/0361922 A1* 11/2022 Hua ................... A61B 17/7085
2022/0387080 A1 12/2022 Hua et al.
2022/0409246 A1 12/2022 Hua
2024/0407811 A1 12/2024 Hua et al.
2025/0387143 A1 12/2025 Hua

FOREIGN PATENT DOCUMENTS

CN 101022848 A 8/2007
CN 201157401 Y 12/2008
CN 102293680 A 12/2011
CN 103096820 A 5/2013
CN 103930059 A 7/2014
EP 1 062 973 A1 12/2000
EP 2 155 322 A2 2/2010
EP 2 777 573 A1 9/2014
EP 2 851 022 A1 3/2015
EP 3 092 964 A1 11/2016
EP 2 892 452 B1 8/2018
GB 2330078 A 4/1999
JP H10-080431 A 3/1998
JP 2005-516697 A 6/2005
JP 2005-324017 A 11/2005
JP 2006-504505 A 2/2006
JP 2007-520319 A 7/2006
JP 2006-518655 A 8/2006
JP 2006-528028 A 12/2006
JP 2007-502662 A 2/2007
JP 2007-524463 A 8/2007
JP 2008-509759 A 4/2008
JP 2008-539029 A 11/2008
JP 2013-526905 A 6/2013

(56) References Cited

FOREIGN PATENT DOCUMENTS

| | | | |
|---|---|---|---|
| JP | 2015-061602 | A | 4/2015 |
| KR | 10-1703003 | B1 | 2/2017 |
| KR | 10-2145362 | B1 | 8/2020 |
| RU | 2285483 | C2 | 10/2006 |
| SU | 1771717 | A1 | 10/1992 |
| WO | WO 03/005943 | A2 | 1/2003 |
| WO | WO 03/066153 | A2 | 8/2003 |
| WO | WO 2004/041100 | A1 | 5/2004 |
| WO | WO 2004/075768 | A2 | 9/2004 |
| WO | WO 2005/051306 | A2 | 6/2005 |
| WO | WO 2006/015087 | A2 | 2/2006 |
| WO | WO 2006/019723 | A2 | 2/2006 |
| WO | WO 2006/099462 | A2 | 9/2006 |
| WO | WO 2007/002144 | A2 | 1/2007 |
| WO | WO 2008/039247 | A2 | 4/2008 |
| WO | WO 2008/136802 | A1 | 11/2008 |
| WO | WO 2008/149289 | A2 | 12/2008 |
| WO | WO 2010/039817 | A2 | 4/2010 |
| WO | WO 2010/039817 | A3 | 7/2010 |
| WO | WO 2010/085782 | A2 | 7/2010 |
| WO | WO 2010/039817 | A4 | 9/2010 |
| WO | WO 2011/040986 | A1 | 4/2011 |
| WO | WO 2011/084788 | A2 | 7/2011 |
| WO | WO 2011/123580 | A1 | 10/2011 |
| WO | WO 2011/133583 | A1 | 10/2011 |
| WO | WO 2012/012310 | A2 | 1/2012 |
| WO | WO 2013/059113 | A1 | 4/2013 |
| WO | WO 2014/159757 | A2 | 10/2014 |
| WO | WO 2017/039762 | A1 | 3/2017 |
| WO | WO 2021/092495 | A1 | 5/2021 |
| WO | WO 2021/108709 | A1 | 6/2021 |

OTHER PUBLICATIONS

"MANTIS® Spinal System Surgical Technique", Stryker Spine, MIMAN-ST-2_Rev-3, 2015, (Brochure) in 48 pages.

2009 K2M Complex Spine Innovations, "Serengeti Minimally Invasive Retractor System, A Simple Approach to Complex Spine", 2 pages, 2009.

2010 K2M Complex Spine Innovations, Mesa Spinal System Lumbar Products for Surgeons Treating Spinal Disorders, 1 page. Downloaded May 6, 2010.

Buchholz, A. et al., "Deformity Correction Through the Use of Reduction Towers: 2-Dimensional Operative Video", Operative Neurosurgery, Aug. 2020, vol. 19, Issue 2, pp. E157-E158.

Buell. T. et al., "Surgical correction of severe adult lumbar scoliosis (major curves 75° ): retrospective analysis with minimum 2-year follow-up", Journal of Neurosurgery Spine, Jun. 2019, vol. 21, pp. 1-14.

Carbunaru, R. et al., "Rechargeable Battery-Powered bion® Microstimulators for Neuromodulation," Proceedings of the 26th Annual International Conference of the IEEE EMBS San Francisco, CA, USA, Sep. 1-5, 2004. 0-7803-B439-3/04/$20.00 © 2004 IEEE, in 4 pages.

Demura, S. et al., "Influence of Rod Contouring on Rod Strength and Stiffness in Spine Surgery", Orthopedics, Jun. 2015, vol. 38(6), pp. e520-e523.

Ezzyat, Y. et al., "Closed-loop stimulation of temporal cortex rescues functional networks and improves memory", Nature Communications, vol. 9, Feb. 2018, in 8 pages. URL: https://www.nature.com/articles/s41467-017-02753-0.

Giles, Jim, "Electric currents boosts brain power" in Nature, Oct. 26, 2004, in 2 pages.

Hewitt, John, "Rise of the Cyborgs", Extreme Tech, Jan. 14, 2013, in 6 pages. URL: https://www.extremetech.com/extreme/144579-rise-of-the-cyborgs.

Koivisto, A.M. et al., "Poor Cognitive Outcome in Shunt-Responsive Idiopathic Normal Pressure Hydrocephalus", Neurosurgery, Jan. 2013, vol. 72(1), pp. 1-8.

Kokabu, T. et al., "Identification of optimized rod shapes to guide anatomical spinal reconstruction for adolescent thoracic idiopathic scoliosis", Journal of Orthopaedic Research, Jul. 2018, pp. 3219-3224.

Laxton, A. et al., "Deep Brain Stimulation for the Treatment of Alzheimer Disease and Dementias", World Neurosurgery, Sep./Oct. 2013, 80 (3/4), S28.e1-8.

Lindsey, C. et al., "The Effects of Rod Contouring on Spinal Construct Fatigue Strength", Spine, Jul. 2006, vol. 31, Issue 15, pp. 1680-1687.

Loeb, G. et al., "The BION Devices: Injectable Interfaces with Peripheral Nerves and Muscles." Neurosurg Focus. 2006;20(5) © 2006 American Association of Neurological Surgeons Posted Aug. 15, 2006, in 12 pages.

Medtronic CD Horizon® Sextant® II—Rod Insertion System—Surgical Technique, 2010, IRN10910-20-03/0710, in 48 pages.

Medtronic Sofamor Danek METRx™ System Surgical Technique "Minimal Access Spinal Technologies" article, 2004, in 22 pages.

Mims, C., "A Hardware Update for the Human Brain", The Wall Street Journal, Jun. 5, 2017, in 4 pages. URL: https://www.wsj.com/articles/a-hardware-update-for-the-human-brain-1496660400.

Santoni, B.G. et al., "Cortical Bone Trajectory for Lumbar Pedicle Screws", The Spine Journal, 2009, vol. 9, pp. 366-373.

Simonite, Tim. "Brain blanket boosts mind control" in New Scientist. Feb. 15, 2008, posted online, in 3 pages.

Singer, Emily, "Want to Enhance Your Brain Power? Research hints that electrically stimulating the brain can speed learning," MIT Technology Review, Jun. 26, 2008, in 2 pages.

Torres, et al., "Body Fat and Body Weight Reduction Following Hypothalamic Deep Brain Stimulation in Monkeys: an Intraventricular approach", International Journal of Obesity, Feb. 21, 2012, pp. 1537-1544.

* cited by examiner 200
214
244
274
226
224
244
212a
214b
212b
212
224
273
214
266
214a
216a
200
2217
214
214b
244
272
212
212b
215
213
224
273
264
266
216
246
272
274
244
224
230

A6-A6
400

490
A2-A2
A4-A4
416
412
414
464
404
462
451
402
V2
V3
V1
406

SYSTEMS AND METHODS FOR PEDICLE SCREW STABILIZATION OF SPINAL VERTEBRAE

BACKGROUND

Field

Embodiments of the present disclosure relate to devices, systems, and methods for treating the spine, including without limitation devices, systems, and methods for stabilizing adjoining vertebrae in at least the cervical, thoracic, and lumbosacral spine.

Description of the Related Art

While some lower back conditions can be ameliorated with non-surgical approaches, spinal fusion is recommended for certain conditions when non-surgical approaches fail. Non-surgical approaches include medications, physical therapy, chiropractic treatment, traction, epidural steroid injections, facet blocks or rhizotomy, weight loss, smoking cession, and acupuncture. Conditions that commonly serve as indications for spinal fusion or stabilization surgery can be divided generally into three categories: (i) trauma induced, (ii) curvature, and (iii) degenerative.

Trauma induced conditions include fractures and ligamentous injuries. Fractures typically result from an unfortunate incident involving an extraneous force or fall but may also arise from pathologic conditions, such as cancer or osteoporosis. Fractures are often compressive in nature and typically lead to a pathological curving of the spine resulting in a loss of the natural lordotic curvature in the lumbar and cervical spine, known as kyphosis. Fractures of the spine also occur with translational or rotational forces perpendicular to the axis of the spine. These forces result in fractures of the facet or pars interarticularis (pars). If the external forces are large enough, vertebrae can collapse resulting in a burst fracture that can injure all three (3) columns of the vertebrae (anterior, middle, and posterior columns). Many traumatic injuries can heal without surgery, but unstable injuries that pose a risk for neurologic injury and/or pain require stabilization through a procedure such as fusion.

A condition called spondylolisthesis characterized by slippage of the spine bones or vertebrae relative to one another can result from fractures of the pars interarticularis (pars fracture) known as spondylolysis. Spondylolisthesis can also develop from malformation of the facet joints by degenerative arthritis as well as congenital malformation and pathologic conditions such as tumors. If the pars on both sides are fractured, then the spinous process and lamina are essentially completely disconnected from the pedicle and vertebral body. This large fragment is called the Gill body. Pars fractures are actually common in people of all ages (often acquired in the teenage years). While many of these patients are mildly symptomatic and do not require surgery, those with progressive symptoms may require surgical decompression with or without fusion. Spondylolisthesis results in misalignment of the spine and increases the risk of a nerve becoming entrapped. Nerves travel within the spinal canal bounded by the vertebrae and their roots protrude from the curved openings in the sides of the vertebrae called foramina (singular is foramen). These spinal nerves are suspected to be the source of back and radicular pain when they become entrapped or when the nerve endings become irritated by irregular or abrasive motion around a disc, bone, or joint. Spondylolisthesis can also aggravate or be accompanied by degeneration of disc or facet joint which can lead to axial back pain.

The normal curvature of the lumbar and cervical spine is lordosis, where the posterior aspect of these spinal levels forms a concave curve. The thoracic spine normally has a kyphotic or convex curve. Curvature conditions include straightening of the natural curvature as well as abnormal lordosis, abnormal kyphosis or lateral/rotational bending called scoliosis. Curvature conditions can occur idiopathically during adolescence, e.g., adolescent idiopathic scoliosis, or develop as a secondary problem in situations where spinal muscle activation is abnormal such as cerebral palsy, spina bifida, or tethered cord syndrome. Abnormal spinal curvature is common in spinal degeneration when the discs and joints degenerate asymmetrically leading to a progressive curvature (scoliosis, kyphosis, or lordosis) as the biomechanics of the spine are disrupted. Curvature conditions also occur after trauma with compression or burst fractures or with ligamentous injury. Additionally, curvature conditions can occur iatrogenically after previous spinal surgery where the anatomy and biomechanics of the spine have been altered. Such situations include the removal of the posterior tension band after laminectomy as well as the alteration of physiologic movement after spinal fusion leading to adjacent level compensation and degeneration. Curvature conditions lead to abnormal biomechanical stress on the discs and facet joints accompanied by compensatory measures such as facet or ligamentous hypertrophy. Patients can develop both axial back pain and radicular pain. In patients who have failed conservative therapy and bracing, surgery can be effective. Surgery in these conditions includes decompression of nerve or spinal cord compression as well as fusion or stabilization. Curvature can be corrected through surgery, and fusion prevents further curvature from developing.

Degenerative conditions include spinal arthritis and recurrent disc herniation. Spinal arthritis is the most common indication for fusion and may exist in the form of severe disc degeneration (also called Degenerative Disc Disease, DDD) or facet disease. Degenerative arthritis can also be a cause of spondylolisthesis in addition to traumatic fractures discussed above. Degenerative conditions are generally accompanied by nerve compression causing radicular pain in the distribution of the nerve's receptive field, which usually correlates with and is manifested in arm or leg pain. Pure nerve compression syndromes such as herniated nucleus pulposus (herniated discs) or foraminal stenosis (narrowing of the side foramina canals through which the nerves pass) can often be treated with decompression without fusion. Pure disc degeneration syndromes can be treated with fusion without decompression of the nerves. However, most commonly disc degeneration occurs in combination with nerve compression causing both axial back pain and radicular limb pain. In these circumstances, fusion surgery is combined with nerve decompression surgery.

Fusion functions to eliminate motion in the disc space and facet joints between adjacent vertebrae. The vertebrae provide the rigid structural framework of the spine and the fibrocartilaginous disc space acts as a cushion or shock-absorber. Degradation of the disc space can distort alignment and alter the biomechanical cushion that the disc affords the adjacent vertebrae. This degradation alters the forces impacted upon the vertebrae and results in axial back pain. Fusion is designed to eliminate movement between adjacent vertebrae by either forming a solid bridge of bone across the disk space and/or creating new bone formation in the posterolateral space to provide stabilization, rigidity, and strength. Sometimes fusion involves a bone graft taken from another location in the body (e.g., autograft from the iliac crest in the pelvis) or from an external source, e.g., allograft. Physicians commonly refer to the level of a fusion. A single level fusion involves stabilizing the two vertebral bones adjacent to a diseased disc. A two-level fusion involves stabilizing three adjacent vertebral bones spanning two problematic disc spaces. Each vertebra makes contacts (joints) with adjacent vertebrae at three points, the paired facet joints located posteriorly and the intervertebral disc located anteriorly. Thus, lumbar fusion can be directed either at the posterior facet joints or at the anterior interbody/disc space or both. When an anterior interbody fusion is performed in combination with posterior fusion, the procedure is termed 360° fusion. One commonly used technique of posterolateral fusion is pedicle screw fusion where screws are directed into the pedicle portions and the bodies of adjacent vertebrae and then rods are connected to the screws across the disc spaces. The screws and rods hold the adjacent vertebrae motionless relative to one another and allow the bone graft that is placed either in the interbody (disc) space or in the posterolateral space to grow into solid bone. Conventional pedicle screws and rods are metal, typically titanium (Ti) alloy but have been made from stainless steel, cobalt chrome, and molybdenum rhenium as well. Recently rods have been made from a minimally flexible polymer called polyetheretherketone (PEEK). Other metals have been used and can also be adopted. These can include, for example, cobalt, molybdenum, and other metallic as well as nonmetal polymers.

A newer lumbar pedicle screw technique involves placing screws from a midline incision and placing screws superiorly and laterally instead of the typical trajectory of starting laterally and aiming medically through the pedicle into the vertebral body. This technique has been named Cortical Bone Trajectory (CBT) because the trajectory of the screw transverses more cortical bone in contrast to cancellous bone. Cortical bone is typically harder and thus provides greater pullout strength. Thus cortical bone trajectory allows smaller and shorter screws with a single midline incision instead of bilateral Wiltse style incisions. The issue with CBT screw trajectory is that the superior screw in a lumbar fusion such as L4 trajectory in a L4, L5 TLIF surgery, has a trajectory that is aimed more superiorly and laterally rather than a medical trajectory. The inferior screw can have a parallel trajectory or have a more straight-in trajectory in the sagittal plane (rather than superior direction). This configuration causes a natural crossing of the superior screw with the inferior screw in that the superior screw is aimed superiorly so a minimally invasive spinal (MIS) screw attached to a tower has the tower pointing inferiorly because the screw is directed superiorly. While the inferior screw is directed is a less superior trajectory so the towers attached to these two screws are bound to interfere. Furthermore since the incision is midline and the screws are directed from medial to lateral direction, then the screws from ipsilateral and contralateral sides also are bound to intersect. Thus cortical bone trajectory is a technique that would benefit from towers attached to screws that did not interfere with each other due to the fact that they have interfering trajectories.

Although anterior and lateral approaches can be performed stand-alone (without posterior instrumentation), many surgeons will back-up or supplement anterior or lateral interbody fusions by placing pedicle screws posteriorly after the interbody cage or graft has been placed. This 360° fusion limits movement more than just an isolated anterior or posterior fusion, and fusion rates are increased. However, in ALIF and lateral interbody (DLIF™, XLIF™) cases, two sets of incisions are required for a 360° fusion.

The posterior approaches (TLIF and PLIF) allow an interbody fusion, pedicle screw fusion, and neural decompression to be done all through the same posterior incision(s). In the TLIF, a single large interbody spacer is inserted on the side ipsilateral to the patient's symptomatic side after neural decompression is completed. If both sides are symptomatic then decompression is required on both sides. A PLIF is performed by placing two interbody spacers, one on each side. Posterior procedures may be done according to: (i) an invasive open procedure in which a large incision and/or several incisions are made, (ii) a percutaneous approach in which small incisions and/or few incisions are made, and potentially (iii) an endoscopic approach in which small incisions are made and all tools and devices are inserted through portals with visualization provided on an external monitor.

Dynamic stabilization techniques have been developed for the posterior spine. These posterior techniques utilize pedicle screws and a dynamic rod. Typically the dynamic rod has a mechanism to bend under certain loads or forces, thereby absorbing some stress and strain that is applied to the spine. The advantage of dynamic stabilization is that motion is preserved in the spine. However, the durability of these systems may be an issue. In fusions, the bone graft (interbody or posterolateral) eventually fuses the vertebrae eliminating the need for the spinal instrumentation (screws and rods). However in dynamic stabilization, fusion does not occur, so the screws and dynamic rods will always be subjected to the strain and forces of the spine. Over time, the possibility of loosening of the pedicle screws or mechanical failure may increase. Sometimes the use of a slightly flexible rod such as a rod made of PEEK may actually increase fusion by reducing stress shielding. Stress shielding occurs when rigid fusion constructs shield the vertebral bone in contact with the bone graft from the stresses required to form and remodel bone.

Posterior lumbar stabilization (fusion and dynamic stabilization) techniques have evolved into minimally invasive approaches because such minimized exposures reduce patient morbidity and facilitate patients' recovery to function. Blood loss and hospital stays are shorter. The process of performing a minimally invasive pedicle screw fusion is the same as that for dynamic stabilization and involves two basic parts. First, screws are placed percutaneously through the pedicle into the vertebral body. For minimally invasive systems, cannulated screws are placed percutaneously over a fluoroscopically (an X-ray that can be seen on a video screen) guided guidance element. Recent advances also allow screws, either cannulated or noncannulated, to be placed using intraoperative navigation, using robotic guidance, or using virtual reality guidance. Generally, two screws are used on each vertebral body being fused, one on a right side and the other on a left side. A single level fusion involves connecting the vertebral bodies that are next to the disc level that is being fused. For instance, a L5, S1 fusion requires screws to be placed at L5 and S1, usually bilaterally, in order to immobilize the L5, S1 disc. The second part of the process involves connecting the screws with a rod and locking the rod and screws together. In dynamic stabilization, the rod or rod-like device (flexible connector) is bendable, but the process of inserting this bendable rod is the same as that for fusion. For example, a rod-like device (flexible connector), like a rod, fits within the screw heads, but may also include an element (a shock absorber, a spring, etc.) that allows some motion. The variations between different minimally invasive systems mostly arise in the method of placing the rod and locking the rod with the screws through a minimal incision.

Before the intervertebral body spacer is inserted, the damaged or degenerated disc within the disc space must be removed. In the TLIF approach, the disc space is accessed through a facetectomy in which the foramen around the nerve roots is opened with a bone-cutting tool such as an osteotome or a high-speed drill. In the PLIF approach, laminectomies or laminotomies are performed to access the disc space. Both TLIF and PLIF allow for decompression of the spinal thecal sac and the nerve roots; however, the facetectomy in a TLIF allows the maximum decompression of the exiting nerve root on that side. With gentle retraction of the thecal sac, the disc space is easily accessed. Then the instruments used for clearing out the degenerated disc may be inserted into the disc space to complete the discectomy.

Following removal of the disc, the surgeon should prepare the bony surfaces, known as the end plates, of the vertebral bodies on each side of the disc that was removed. Peeling off the end plate with a tool such as a curette induces bleeding which stimulates healing and assimilation of the bone graft to be inserted into the interbody space. The spacer or cage that is to be inserted is typically constructed of bone, titanium, carbon fiber, or polymers such as PEEK. The spacer is usually hollow or at least porous to accommodate bone graft material therein. Bone inducing protein such as bone morphogenetic protein (BMP) is also commonly placed within the spacer. After placing the spacer and bone graft, the rods may be inserted into the pedicle screws and the screws can be tightened to lock the rods in place.

Pedicle screw fusions such as the TLIF can be done open through a single large incision or through a minimally invasive (MIS) approach in which the incision size(s) are smaller, and less tissue is damaged or injured. MIS TLIF typically uses percutaneous pedicle screws where each screw is placed through a small incision just about the side of the diameter of a single screw, screw head, or the largest screw insertion tool. Typically, the placement of the percutaneous screws is straightforward. This is because screws are long and thin and are screwed through the tissue into the bone either directly or over a guidewire that is placed through either fluoroscopic guidance or using stereotactic navigation sometimes with the aid of a surgical robotic. Whereas in the open approach the screws are placed using visually identified anatomic landmarks and fluoroscopic guidance, though navigation and robotic guidance can help in open cases as well. Because percutaneous pedicle screws are placed through small incisions that are barely large enough to fit the screw or screw insertion tools, virtually no visual landmarks are available. There are miniopen approaches where visual landmarks for placing pedicle screws can be identified through tiny incisions using either a microscope or endoscope through either a small tubular retractor or endoscope. The key is that once the pedicle screw tract is located and the guidewire is placed into the pedicle screw tract, then placing a percutaneous pedicle screw over the guidewire is relatively easy. Also, stereotactic navigation and robotic guidance has also made placement of pedicle screws relatively easy.

In most of the minimally invasive surgery (MIS) systems used today, a guidance element, such as a wire or guidewire, is placed percutaneously under fluoroscopic guidance through the pedicle. Recent advances also allow screws, either cannulated or noncannulated, to be placed using intraoperative navigation, using robotic guidance, intraoperative CT, or using virtual reality guidance. These methods also allow accurate placement of pedicle screws directly without guidewire and without cannulation. If a guidewire system is used, percutaneous cannulated drills and screw taps are inserted over the guidance element/wire to prepare the tract through the pedicle and vertebral body for pedicle screw insertion. Dilating tubes and a guidance tube or a retractor system can often be used to dilate and hold open the path around the guidance element through skin and muscle to reduce injury to muscle and tissue when pedicle screws and insertion tools are inserted. Pedicle screws are inserted over the guidance elements either with or without passage through a guidance tube/retractor. Again, because of the development and wide spread use of intraoperative navigation to guide pedicle screw placement, some pedicle screws can be placed without the use of predrilling a hole or the use of a guidewire. These systems use intraoperative navigation to directly place the pedicle screw through the tissue into bone without predrilling a hole or tapping the hole. Additionally robotic arms can now be used to also aid in the accurate placement of pedicle screws in addition and often combination with navigation systems.

In MIS pedicle screw fusion, after the pedicle screw has been inserted, there are still critical steps in connecting the screw heads and locking adjacent screws using a rod and locking cap. The insertion of rods that connect the screw heads and locking caps to lock the rod inside the screw heads are currently some of the most difficult steps while using a MIS approach through a minimal incision. In order to place the rod and locking assembly into the screw heads, each screw head is associated with blades or towers that extend upwards from the screwhead through the skin incision. The tower has to accommodate the rod and locking assemblies so it is typically the same size or larger than the maximum diameter of the screw head. Once the towers attached to the screws are in place, the rod is then inserted through one of a variety of methods. The leading MIS system is Sextant™ by Medtronic. In this system, the rod is placed by forming a pendulum like mechanism. The two or three towers (for one or two-level fusion, respectively) are coupled together to align the towers, and the rod is swung around through a separate incision superior or inferior to the towers in a pendulum fashion. Once the rod is swung in place, locking caps are placed through the towers and tightened. Alternatively, most of the existing systems insert the rod through one of the towers and then turn the rod approximately 90° to capture the other screws in the other towers. Inserting the rod through the screw heads in a minimally invasive system is done blindly, e.g., without direct visualization of the screw head. Thus, this process is sometimes tedious and frustrating.

The Sextant™ system and other existing systems that use towers are hindered by both the number of incisions required. The use of a separate tower for each screw requires a separate incision for each tower, or a single incision long enough to accommodate two towers. The Sextant™ system also requires an additional incision for the rod, equaling six incisions (three on each side) for a single level fusion and eight incisions for a two level fusion. The other existing tower systems that use the direct rod insert and turn mechanism still require one incision for each screw and each incision has to be larger than the size of a tower through which the screws are inserted. Typically, each incision is at least 15 mm in length. When the sum of the lengths of all incisions on both sides are totaled, the total length of the current leading minimally invasive systems often are longer than the single midline incision of a traditional "open" approach for a single or two level pedicle screw fusion.

Furthermore none of the current MIS pedicle screw systems has been designed to take advantage of the lumbar lordosis that is typically present in most patients. About 80% of lumbar pedicle screw fusions are performed at the lowest two levels L4 to L5 and L5 to S1. These lowest lumbar levels also typically exhibit the strongest lumbar lordosis such that pedicle screw tracts through L4, L5, S1 and even L3 often intersect near a single point often near the skin similar to spokes on a bicycle tire. For most pedicle screw systems, this lordotic curvature is a hindrance in which the towers of the pedicle screws all intersect and cross. Crossing of the towers make it difficult for these MIS screw systems to allow a rod to be placed through the channels of the towers.

SUMMARY OF SOME EXAMPLE EMBODIMENTS

Some embodiments described in this application are directed to systems, devices and/or methods for bone stabilization, such as for stabilizing the spine. In some embodiments, one or more guiding elements may be provided, which may also be referred to herein as guidance elements, guide elements, towers, or extensions or other terms as later described. Guiding elements may be connectable with, attachable to, and/or engageable with bone screws, such as pedicle screws. These guiding elements may be utilized in some embodiments to deliver a connecting member, such as a rod, to bone screws implanted within a patient's vertebrae. Additional systems, devices and methods are described herein, including but not limited to rod insertion devices and guidance tools for drills. The systems, methods and devices of this disclosure each have several innovative aspects, implementations, or aspects, no single one of which is solely responsible for the desirable attributes disclosed herein.

Some embodiments of a system for bone stabilization disclosed herein can have a first guiding element comprising an elongate body having a first longitudinal axis, a proximal end and a distal end, the distal end configured to engage with a first bone screw, a second guiding element comprising an elongate body having a second longitudinal axis, a proximal end and a distal end, the distal end configured to engage with a second bone screw, and an opening provided at an intermediate portion of the first guiding element when in use. In some embodiments, the opening can be sized and configured to allow for passage of the second guiding element therethrough such that the second longitudinal axis is at an angle relative to the first longitudinal axis, wherein the opening is sized and configured to limit movement and/or rotation of the second guiding element along the first longitudinal axis relative to the first guiding element.

Disclosed herein are embodiments of a system for stabilizing spinal vertebrae through a skin incision. In some embodiments, the system can include a first screw having a first screw head and a second screw having a second screw head, a first tower having a distal portion, a proximal portion, and a bend between the distal portion and the proximal portion, and a second tower having a distal portion, a proximal portion, and a bend between the distal portion and the proximal portion. In some embodiments, the system can further include a third tower having a distal portion and a proximal portion, the third tower configured to be removably coupled with a third screw at a distal end of the third tower.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first tower can be configured to be removably coupled with the first screw at a distal end of the first tower; wherein the second tower can be configured to be removably coupled with the second screw at a distal end of the second tower; wherein the first tower is configured to removably couple with the first screw such that, when the first tower is coupled with the first screw, an axial centerline of the distal portion of the first tower is approximately collinear with an axial centerline of the first screw; wherein the second tower is configured to removably couple with the second screw such that, when the second tower is coupled with the second screw, an axial centerline of the distal portion of the second tower is approximately collinear with an axial centerline of the second screw; wherein the proximal portion of the first tower extends at an acute, nonzero angle away from the axial centerline of the distal portion of the first tower; wherein the proximal portion of the second tower extends at an acute, nonzero angle away from the axial centerline of the distal portion of the second tower; wherein, in an operable state, the first, second towers are configured to intersect one another; and/or wherein the proximal portions of one or more of the towers (for example and without limitation, the first and third towers or extensions) are configured to be compatible with graspers, coupling mechanisms, and other components of surgical robotic systems. Additionally and/or alternatively, any embodiments of the system disclosed herein may further include a third screw and a third tower wherein the third tower is configured to removably couple with the third screw such that, when the third tower is coupled with the third screw, an axial centerline of the distal portion of the third tower is approximately collinear with an axial centerline of the third screw Also disclosed herein are embodiments of a system for stabilizing spinal vertebrae through a skin incision that can include a first screw having a first screw head, and a second screw having a second screw head, a first tower having a distal portion and a proximal portion, and a second tower having a distal portion and a proximal portion. Additionally and/or alternatively, the system can further include a third screw having a third screw head, and a third tower having a distal portion and a proximal portion, the third tower configured to be removably coupled with the third screw at a distal end of the third tower.

Also disclosed herein are embodiments of a system for inserting a connection element or rod through a separate incision than the incision used for receiving the first and second towers. The system may be or may include a rod insertion device that can include at least a radial member and an arc member. The rod insertion device can be configured to couple to at least one of the first or second towers to rotatably insert the connection element or rod through the second incision into a position to engage with the first and second screws, respectively.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first tower can be configured to be removably coupled with the first screw at a distal end of the first tower; wherein the third tower can be configured to be removably coupled with the third screw at a distal end of the third tower; wherein the first tower is configured to removably couple with the first screw such that, when the first tower is coupled with the first screw, an axial centerline of the distal portion of the first tower is approximately collinear with an axial centerline of the first screw; wherein the second tower is configured to removably couple with the second screw such that, when the second tower is coupled with the second screw, an axial centerline of the distal portion of the second tower is approximately collinear with an axial centerline of the second screw; wherein the third tower is configured to removably couple with the third screw such that, when the third tower is coupled with the third screw, an axial centerline of the distal portion of the third tower is approximately collinear with an axial centerline of the third screw; wherein the proximal portion of the first tower extends at an acute, nonzero angle away from the axial centerline of the distal portion of the first tower; wherein the proximal portion of the third tower extends at an acute, nonzero angle away from the axial centerline of the distal portion of the third tower; wherein, in an operable state, the proximal portion of the first tower extends away from the second tower in a first direction; and/or wherein, in an operable state, the proximal portion of the third tower also extends away from the second tower in the first direction.

Also disclosed herein are embodiments of a method of stabilizing spinal vertebrae. In some embodiments, the method can include implanting a first screw that is coupled with a first tower through an incision into a first vertebra, advancing a second tower that is coupled with a second screw through the opening formed in the first tower and implanting the second screw into a second vertebra, and moving a proximal portion of the first tower toward a proximal portion of the second tower to move the first vertebra from a first position relative to the second vertebra to a second position relative to the second vertebra. Additionally and/or alternatively, the method can include further advancing a third screw that is coupled with a third tower through an opening formed in the first tower and the second tower and implanting the third screw into a third vertebra.

Also disclosed herein are embodiments of a method of stabilizing spinal vertebrae. In some embodiments, the method can include implanting a first screw that is coupled with a first extension through a single incision into a first vertebra, the first extension having a proximal portion and a distal portion, advancing a second extension that is coupled with a second screw through the single incision and through the first opening formed in the first extension so that an axial centerline of at least a distal portion of the second extension is at an acute angle relative to the axial centerline of at least the distal portion of the first extension, and implanting the second screw into a second vertebra. Additionally and/or alternatively, the method can include advancing a third extension that is coupled with a third screw through the single incision and through a first opening formed in the first extension so that an axial centerline of at least a distal portion of the third extension is at an acute angle relative to an axial centerline of at least the distal portion of the first extension, implanting the third screw into a third vertebra.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein, in an operable state, the first, second, and third towers are configured to intersect at or adjacent to a skin level of a patient; wherein, in an operable state, the first, second, and third towers are configured to intersect in an operable state at or adjacent to a skin level of a patient such that a distance from the skin level to a proximal most end of the distal portion of the first tower is less than or equal to 10% of a length of the distal portion of the first tower and a distance from the skin level to a proximal most end of the distal portion of the third tower is less than or equal to 10% of a length of the distal portion of the third tower; wherein the first tower has an opening therein sized and configured to receive the second tower and the third tower therein such that, in an operable state, an outer wall of a portion of the first tower surrounds an outer surface of a portion of the second and third towers; wherein the opening extends at least through a proximal end of the distal portion of the first tower; wherein the opening extends along the first tower to an edge that is adjacent to a proximal end of the distal portion of the first tower; wherein the proximal portion of the first tower is configured such that, in an operable state of the system, the proximal portion of the first tower also extends at an acute, nonzero angle away from the axial centerline of the proximal portion of the second tower so that the proximal portion of the first tower forms an acute angle relative to the proximal portion of the second tower; wherein the distal portion of the first tower is configured such that, in an operable state of the system, the distal portion of the first tower extends at an acute, nonzero angle away from the axial centerline of the distal portion of the second tower so that the distal portion of the first tower forms an acute angle relative to the distal portion of the second tower; wherein the proximal portion of the third tower is configured such that, in an operable state of the system, the proximal portion of the third tower also extends at an acute, nonzero angle away from the axial centerline of the proximal portion of the second tower so that the proximal portion of the third tower forms an acute angle relative to the proximal portion of the second tower; wherein the distal portion of the third tower is configured such that, in an operable state of the system, the distal portion of the third tower extends at an acute, nonzero angle away from the axial centerline of the distal portion of the second tower so that the distal portion of the third tower forms an acute angle relative to the distal portion of the second tower; and/or wherein the distal portion of the first tower and/or the third tower has a curved cross-sectional profile and the proximal portion of the first tower and/or the third tower has a flat or rectangular cross-sectional profile.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first tower is sized and configured such that, in an operable state, the proximal portion of the first tower extends away from a skin incision in a first direction and the proximal portion of the third tower also extends away from the skin incision in the first direction; wherein, in an operable state, the proximal portion of the third tower is positioned between the proximal portion of the first and second towers; wherein the first tower is sized and configured such that, in an operable state, the proximal portion of the first tower extends away from a skin incision in a first direction and the proximal portion of the third tower also extends away from the skin incision in the first direction; wherein the distal portion of the first tower extends away from the first screw to a height just below the skin incision, or to a height level with the skin of a patient, when the first screw is fully implanted in a first vertebra; wherein the proximal portion of the first tower is configured to be grasped by a surgeon to enable a surgeon to exert a counter-torque force on the first tower about at least the axial centerline of the distal portion of the first tower; wherein, in an operable state, the proximal portion of the third tower is configured to be grasped by a surgeon to enable a surgeon to exert a rotational force on the third tower about at least the axial centerline of the distal portion of the third tower; wherein, in an operable state, the system is configured such that moving the proximal portion of the first tower toward the proximal portion of the third tower will cause a compressive force on at least a first vertebra that the first screw is implanted in relative to a third vertebra that the third screw is implanted in; wherein the first tower and the third tower are sized and configured such that only the proximal portions of the first and third towers are outside of a skin incision when the first screw is implanted in a first vertebra; wherein the system is configured such that the first, second, and third screws are implanted through the same skin incision; wherein the proximal portion of the first tower has a length that is approximately the same as a length of the distal portion of the first tower; wherein the proximal portion of the first tower has a length that is at least 80% of a length of the distal portion of the first tower; wherein the proximal portion of the first tower is removably coupled with the distal portion of the first tower and the proximal portion of the third tower is removably coupled with the distal portion of the third tower; wherein the proximal portion of the first tower is non-removably coupled with the distal portion of the first tower and the proximal portion of the third tower is non-removably coupled with the distal portion of the third tower; wherein the proximal portion of the first tower is integrally formed with the body portion of the first tower; wherein at least the distal portions of the first tower, the second tower, and the third tower have a complete or a partial tubular shape; wherein the first tower has a pair of hooks configured to receive a pair of wires used during an implantation procedure; wherein the hooks are configured to provide a surface against which the third tower can rotate; wherein the first tower has a projection which provides a fulcrum for rotation of the third tower relative to the first tower; wherein the third tower can have an opening formed through a wall portion of the third tower, wherein the opening can be configured to allow the second tower to pass through the opening of the third tower in an operable state and such that at least a portion of a wall of the third portion at least partially surrounds an outside surface of the second tower; wherein the distal portion of the first tower and/or the third tower is open along one side thereof and not fully enclosed; and/or wherein, in an operable state, an axial centerline of both the distal portion of the third tower and the proximal portion of the third tower extend at a nonzero angle away from the axial centerline of the second tower in a same direction.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein at least the distal portion of the first tower and the distal portion of the third tower have an adjustable length; wherein at least the distal portion of the first tower, the distal portion of the second tower, and the distal portion of the third tower are generally cylindrically shaped; wherein the proximal portion of the first tower and the proximal portion of the third tower have a cross-sectional profile having a curved shape; wherein the proximal portion of the first tower and the proximal portion of the third tower have a cross-sectional profile having a semi-circular tubular shape; wherein the proximal portion of the first tower and the proximal portion of the third tower have a planar shape; wherein the device, system, or method can include: a rigid connecting element; a first receiving element coupled with the first screw head; a second receiving element coupled with the second screw head; and a third receiving element coupled with the third screw head; wherein the first, second, and third receiving elements are configured to operably receive the connecting element that, in an operable state, extends between the first, second, and third receiving elements when the first, second, and third screws are implanted in a first, second, and third vertebra, respectively; wherein the first tower has at least one opening extending through a side of the distal portion thereof configured to receive a connecting element that is configured to extend between the first, second, and third screws in an operable state, wherein the second tower has at least one opening extending through a side of the body portion thereof configured to receive a connecting element that is configured to extend between the first, second, and third screws in an operable state, and the third tower has at least one opening extending through a side of the body portion thereof configured to receive a connecting element that is configured to extend between the first, second, and third screws in an operable state; wherein the device, system, or method can include one or more covers configured to selectively couple with the first tower, the second tower, and/or the third tower to selectively cover a channel or an opening of the first tower, the second tower, and/or the third tower and increase a torsional or bending rigidity of the first tower, the second tower, and/or the third tower; and/or wherein the device, system, or method can include two or more of the first towers and/or two or more of the third towers, wherein each of the two or more of the first towers define a different angle between the proximal portion and the distal portion of the first towers and each of the two or more of the third towers define a different angle between the proximal portion and the distal portion of the third towers.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein, in an operable state, the first and second towers are configured to intersect at or adjacent to a skin level of a patient; wherein the device, system, or method can include advancing a connecting element toward the first screw and the second screw and securing the connecting element to the first screw and/or the second screw to prevent the first vertebra from moving back to the first position relative to the second vertebra; wherein the first extension has a proximal portion, a distal portion, and a bend between the proximal and distal portions; wherein the second extension; wherein the first and the second extensions are sized and configured such that the proximal portion of the first and the second extensions are positioned under an outside surface of a patient's skin; and/or wherein the device, system, or method can include advancing the first and the third extensions through a single incision in a patient's skin. Additionally and/or alternatively, in an operable state, a third tower may be further configured to intersect at or adjacent to a skin level of a patient similar to the first and third towers.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first extension has a bend between the proximal portion of the first extension and the distal portion of the first extension such that an axial centerline of the proximal portion of the first extension is at an acute angle relative to an axial centerline of the distal portion of the first extension; wherein the second extension has a bend between the proximal portion of the second extension and the distal portion of the second extension such that an axial centerline of the proximal portion of the third extension is at an acute angle relative to an axial centerline of the distal portion of the third extension; and/or wherein the device, system, or method can include moving the proximal portion of the first extension toward a proximal portion of the second extension to rotate the first extension relative to the second extension and move the first screw toward the second screw, thereby moving the first vertebra toward the second vertebra.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein a rod insertion device having a spacer, a radial member, and an arc member are provided for advancing a connection element toward the first and second towers. The body portion may be any desired length to extend the effective length of the towers. The radial member defines a radius of a circumferential path along which the arc member is advanced. The arc member has a curvature corresponding the curvature of the circumferential path defined by the length of the radial member. The arc member is configured to engage a connection element for approaching the towers and/or screws. The arc member is configured to enter a second incision separate from the first incision through which the towers engage the vertebrae.

Some embodiments disclosed herein can be described as follows:

1. A system for bone stabilization, comprising:
   - a first guiding element comprising an elongate body having a first longitudinal axis, a proximal end and a distal end, the distal end configured to engage with a first bone screw;
   - a second guiding element comprising an elongate body having a second longitudinal axis, a proximal end and a distal end, the distal end configured to engage with a second bone screw;
   - an opening provided at an intermediate portion of the first guiding element when in use, wherein the opening is sized and configured to allow for passage of the second guiding element therethrough such that the second longitudinal axis is at an angle relative to the first longitudinal axis, wherein the opening is sized and configured to limit movement of the second guiding element along the first longitudinal axis; and
   - a rod insertion device having a rotating arm configured to couple with at least one of the first guiding element and the second guiding element such that the rotating arm can rotate about an axis of rotation relative to the first guiding element and/or the second guiding element, wherein the rod insertion device is configured to advance a connecting element (also referred to herein as a rod) into a screwhead of the first bone screw and a screwhead of the second bone screw.
2. The system of Embodiment 1, wherein the first and second guiding elements each comprise a pair of blades.
3. The system of Embodiment 2, wherein each pair of blades has one or more bends or curves to increase a separation distance between opposing blades when the pair of blades is engaged with a bone screw.
4. The system of Embodiment 1, wherein the first and second guiding elements comprise partial tubes.
5. The system of any one of the previous Embodiments, wherein the opening is provided within an intermediate portion of the first guiding element.
6. The system of any one of Embodiments 1-4, wherein the opening is provided by an external restraint configured to surround at least the first guiding element.
7. The system of any one of the previous Embodiments, wherein at least a proximal portion of the first guiding element is in a first plane and at least a proximal portion of the second guiding element is also in the first plane.
8. A system for bone stabilization, comprising:
   - a first guiding element comprising an elongate body having a first longitudinal axis, a proximal end and a distal end, the distal end configured to engage with a first bone screw;
   - a second guiding element comprising an elongate body having a second longitudinal axis, a proximal end and a distal end, the distal end configured to engage with a second bone screw,
   - wherein the second guiding element is configured to pass through a portion of the first guiding element when the first and second guiding elements are engaged with the first and second bone screws, respectively, and the first and second bone screws are implanted within a patient;
   - means for limiting relative movement and creating a fulcrum between the first and second guiding elements when the second guiding element passes through a portion of the first guiding element and when the first and second guiding elements are engaged with the first and second bone screws, respectively, and the first and second bone screws are implanted within a patient;
   - a rod insertion device comprising a rotating arm configured to couple with at least one of the first guiding element and the second guiding element such that the rotating arm can rotate about an axis of rotation relative to the first guiding element and/or the second guiding element, wherein the rod insertion device is configured to advance a connecting element (also referred to herein as a rod) into a screwhead of the first bone screw and a screwhead of the second bone screw.

Some embodiments are directed to a screw comprising one or more features of the foregoing description. Some embodiments are directed to a device, system and/or method as illustrated and/or described. Some embodiments are directed to a method of operating any of the devices or systems of the foregoing description. Further embodiments are described throughout the following description, including but not limited to systems for stabilizing spinal vertebrae, methods for stabilizing spinal vertebrae, guiding assemblies, screws, rod inserters, methods of operating any of the foregoing, and other devices, systems and methods.

In one aspect of the system and methods disclosed herein, a system for stabilizing spinal vertebrae through a skin incision is described. The system includes a first screw having a first screw head, and a second screw having a second screw head. The system further includes a first tower and a second tower. The first tower has a distal portion, a proximal portion, and a bend between the distal portion and the proximal portion. The first tower is configured to be removably coupled with the first screw at a distal end of the first tower. The second tower has a distal portion and a proximal portion. The second tower is configured to be removably coupled with the second screw at a distal end of the second tower. The system further includes a rod insertion device. The rod insertion device includes a rotating arm. The rod insertion device is configured to couple with at least one of the first tower and the second tower such that the rotating arm can rotate about an axis of rotation relative to the first tower and/or the second tower. The rod insertion device is configured to advance a connecting element into the first screw head of the first screw and the second screw head of the second screw. In some examples, the rod insertion device is configured to be removably coupled to at least one of the first tower and the second tower. In some examples, the rod insertion device is configured to be removably coupled to only one of the first tower or the second tower at a time. In some examples, the rod insertion device further includes a body portion including a longitudinal lumen and a transverse lumen. The rotating arm includes a radial member and an arc member extending from a distal end of the radial member, wherein the rotating arm is rotatably coupled to the body portion about the transverse lumen. In some examples, the first tower has an opening therein that is completely enclosed, wherein the second tower and at least part of the rod insertion device are received within the opening in an operable state of the system such that an outer wall of a portion of the first tower surrounds an outer surface of a portion of the second tower and an outer surface of at least part of the rod insertion device. In some examples, the opening extends at least through a proximal end of the distal portion of the first tower. In some examples, the proximal portion of the first tower is configured such that, in an operable state of the system, the proximal portion of the first tower also extends at an acute, nonzero angle away from a longitudinal centerline of the proximal portion of the second tower so that the proximal portion of the first tower forms an acute angle relative to the proximal portion of the second tower. In some examples, the distal portion of the first tower is configured such that, in an operable state of the system, the distal portion of the first tower extends at an acute, nonzero angle away from a longitudinal centerline of the distal portion of the second tower so that the distal portion of the first tower forms an acute angle relative to the distal portion of the second tower. In some examples, the first tower includes one or more longitudinal axes that extend axially through a portion of the first tower and the second tower includes one or more longitudinal axes that extend axially through a portion of the second tower, wherein, in an operable state of the system, the one or more longitudinal axes that extend axially through a portion of the first tower and the one or more longitudinal axes that extend axially through a portion of the second tower are coplanar. In some examples, in an operable state of the system, the proximal portion of the first tower extends in the direction of the spine. In some examples, in an operable state of the system, the proximal portion of the first tower is axially displaced from the proximal portion of the second tower in the direction of the spine.

In one aspect of the system and methods disclosed herein, a system for stabilizing spinal vertebrae through a skin incision is described. The system includes a first screw having a first screw head and a second screw having a second screw head. The system further includes a first tower and a second tower. The first tower has a first outer wall defining a lumen extending along a first longitudinal centerline, and a first opening orthogonal to the first longitudinal centerline, the opening positioned at a proximal end of the first outer wall. The first tower is configured to be removably coupled with the first screw at a distal end of the first tower. The second tower has a second outer wall defining a lumen extending along a second longitudinal centerline, and a second opening orthogonal to the second longitudinal centerline, the second opening positioned at a proximal end of the second outer wall. The second tower is configured to be removably coupled with the second screw at a distal end of the second tower. The system further includes a rod insertion device. The rod insertion device includes a body portion, a rotating member, an arc member; and an insertable support pin. The body portion is configured to be removably coupled to at least one of the first tower and the second tower. The body portion includes a longitudinal lumen and a transverse lumen orthogonal to the longitudinal lumen. The rotating member is configured to be rotatably coupled to the body portion about the transverse lumen. The arc member extends from a distal end of the rotating member opposite the body portion. The arc member is configured to removably support a connection rod. The insertable support pin is configured to be removably inserted through the longitudinal lumen of the body portion and into the lumen of at least one of the first tower and the second tower. The rod insertion device is configured to advance the connection rod to at least the first screw and the second screw. The longitudinal lumen is configured to be coaxial with at least one of the first longitudinal centerline or the second longitudinal centerline. In some examples, the first tower further includes a first distal portion defining the first outer wall and a first proximal portion adjacent to the first distal portion, wherein the first opening is positioned at the proximal end of the first distal portion, and the second tower further includes a second distal portion defining the second outer wall and a second proximal portion adjacent to the second distal portion, wherein the second opening is positioned at the proximal end of the second distal portion. In some examples, the first proximal portion extends at an acute, nonzero angle away from the first longitudinal centerline of the first distal portion and the second proximal portion extends at an acute, nonzero angle away from the second longitudinal centerline of the second distal portion. In some examples, the first longitudinal centerline and the second longitudinal centerline are coplanar.

In one aspect of the system and methods disclosed herein, a method of stabilizing spinal vertebrae is described. The method includes implanting two or more screws coupled with a corresponding one of two or more towers through an incision into a corresponding vertebra, aligning a longitudinal lumen of a body portion of a rod insertion device with a longitudinal centerline of at least one of the two or more towers, inserting an insertion support pin through the longitudinal lumen and into a lumen defined by an outer wall of the at least one of the two or more towers, moving a first tower of the two or more towers relative to a second tower of the two or more towers to move a first vertebra from a first position relative to a second vertebra to a second position relative to the second vertebra, and advancing a connecting element toward the two or more screws; and securing the connecting element to at least one of the two or more screws to prevent the first vertebra from moving back to the first position relative to the second vertebra. In some examples, implanting two or more screws coupled with a corresponding tower through an incision into a corresponding vertebra includes inserting a first screw that is coupled with the first tower through an incision into the first vertebra and advancing the second tower that is coupled with a second screw through an opening formed in the first tower and implanting the second screw into the second vertebra. In some examples, advancing the connecting element toward the two or more screws includes rotating a radial arm of the rod insertion device about a transverse lumen, wherein an arc member extending from a distal end of the radial arm follows an arcuate path to the two or more screws. In some examples, the method further includes retracting the insertion support pin from the at least one of the two or more towers after the connecting element is advanced past a first screw of the two or more screws, aligning the longitudinal lumen of the body portion of the rod insertion device with a longitudinal centerline of another one of the two or more towers, inserting the insertion support pin through the longitudinal lumen and into a lumen defined by an outer wall of another one of the two or more towers and advancing the connecting element toward a second one of the two or more screws. In some examples, the two or more towers include a first tower and a second tower. The first tower has a proximal portion, a distal portion, and a bend between the proximal portion of the first tower and the distal portion of the first tower such that an axial centerline of the proximal portion of the first tower is at an acute angle relative to an axial centerline of the distal portion of the first tower. The second tower has a proximal portion, a distal portion, and a bend between the proximal portion of the second tower and the distal portion of the second tower such that an axial centerline of the proximal portion of the second tower is at an acute angle relative to an axial centerline of the distal portion of the second tower.

BRIEF DESCRIPTION OF THE DRAWINGS

The accompanying drawings, which are incorporated in and constitute a part of the specification, illustrate embodiments of the present disclosure, and together with the general description given above and the detailed description of the embodiments given below, serve to explain the principles of the embodiments of the present disclosure.

DETAILED DESCRIPTION OF SOME EXEMPLIFYING EMBODIMENTS

Figure 1A:
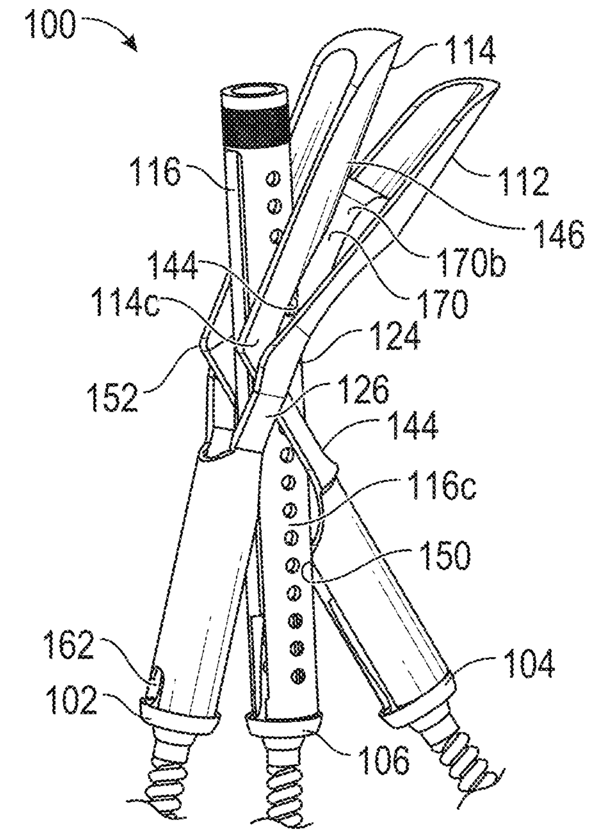
FIGS. 1A-1G illustrate an embodiment of a system for stabilizing spinal vertebrae comprising spinal screws.

Embodiments of the present disclosure relate to medical devices, systems and methods for bone fixation. Specifically, some embodiments disclosed herein can be configured to stabilize adjoining vertebrae in at least the cervical, thoracic, and lumbosacral spine. In addition, some embodiments can be configured to fuse and stabilize vertebrae in the lumbar spine to alleviate axial back pain and radicular pain. Some embodiments can be configured to improve minimally invasive surgical (MIS) approaches to pedicle screw fusion by reducing the number and size of incisions and the size of the medical instruments inserted therein. Further, some embodiments disclosed herein can improve the efficiency of percutaneous lumbar pedicle screw fusion for the surgeon while minimizing the surgical trauma to the patient's tissue.

For example and without limitation, some embodiments of the systems for stabilizing spinal vertebrae disclosed herein are directed towards, but not limited to, improving minimally invasive (optionally adaptable for use with the percutaneous or endoscopic approach) TLIF and PLIF approaches and backing up the ALIF, DLIF™, and XLIF™ approaches. TLIF approaches can provide several advantages including: (i) stabilization of both the anterior and posterior portions of the spine through one or more posterior incision(s); (ii) the ability to fill with bone graft material a greater volume and diversity of spaces (front disc space with the spacer, amongst the screws and rods on the sides, and in the back of vertebrae) increasing the chances of a successful stabilization through the development and solidification of bone; (iii) the spacer placed within the front disc space maintains the natural interbody disc height to reduce pressure on nerve roots (from bone spurs, thickened, ligaments, etc.); and (iv) enhanced safety because the spinal canal is accessed from one side only and this reduces the risk of pinching, stretching, or otherwise agitating the spinal nerves.

Embodiments of the disclosure provide a system, device and/or method for performing a minimally invasive posterior and/or transforaminal lumbar pedicle screw fusion or stabilization procedure. Hereinafter references to "fusion" implicitly include stabilization which offers somewhat greater motion short of completely fusing the bone. Likewise, hereinafter references to "stabilization" implicitly include fusion. The main situations in which a surgeon can use the disclosed system can include a minimally invasive TLIF procedure with either: (i) a micro-lumbar interbody fusion, MLIF™, or (ii) mini-open TLIF on the symptomatic side to decompress the neural compression, and a pedicle screw fusion through a minimally invasive incision on the contralateral side. Similarly, the system disclosed herein would be used bilaterally in a PLIF approach with the decompression and interbody spacer placement performed bilaterally. Alternatively, the disclosed system is ideal for "backing up" (with a minimal posterior incision) anterior interbody fusions (ALIF) and lateral interbody fusions (XLIF™ and DLIF™). MLIF™ collectively encompasses (i) transforaminal lumbar interbody fusions and stabilizations, (ii) posterior lumbar interbody fusions and stabilizations, (iii) anterior lumbar interbody fusions and stabilizations, and (iv) lateral lumbar interbody fusions and stabilizations through a minimally invasive "micro" approach using the guidance system described herein, and (v) posterolateral instrumented fusions where only pedicle screws are placed for posterolateral fusion without using interbody spacers or implants. Since the lateral fusions such as the XLIF or DLIF are truly minimally invasive, a minimal posterior incision for backing up the lateral interbody spacer with pedicle screw fusion would be very complementary. Lateral interbody fusions are becoming more popular and more spine companies are coming out with their own lateral interbody fusion systems. It will be appreciated that although certain embodiments described herein are directed to minimally invasive procedures through a single skin incision, the systems and methods may also be used in open surgery or mini-open procedures through openings in the skin of a patient as desired by the practicing surgeon.

The lumbar spine has a lordotic curvature such that the lowest levels, L4, L5 and S1, have a posteriorly concave orientation or alignment, while the upper levels, L1-L3, are less lordotic. This curvature sets up a unique situation in which the trajectories through the pedicles (the trajectories to insert the pedicle screws) from L2 to S1 are not parallel. Rather, the trajectories commonly intersect at a point around the level of the skin. This configuration is similar to the spokes of a wheel in which the spokes (trajectories) meet at a common center point (a hub). Given that many patients have such a lordotic configuration of the lumbar spine, it is possible to insert pedicle screws through a single incision centered in the middle of the lumbar curvature. However, if each screw required a separate tower (or tube) (as in conventional tower/tube systems) in order for multiple screws to exist simultaneously, then the sum cross sectional area of the towers/tubes does not permit a single small incision. The towers/tubes interfere with each other and get in the way of one another due to their size. It is also difficult to place the rod through the channels of the towers and into the seats of the pedicle screws when the towers of the pedicle screws are crossed and not aligned in a straight line.

An alternative method is necessary in order to minimize the number and size of incisions. Reducing the number and size of incisions minimizes the tissue trauma needed to place pedicle screws for lumbar stabilization or fusion. An ideal system and procedure would take full advantage of the natural curvature of the lumbar spine in order to provide this reduction. However, the apparatuses and methods of the present application described and claimed herein are not limited to applications in the lumbar vertebrae and may also find use for fusing, stabilizing, or otherwise treating vertebrae in other regions of the spine such as the cervical spine where lordotic curvature is again the typical anatomical alignment.

The number of osteoporotic spinal patients requiring surgical intervention is increasing. Historically this complex group of patients has had complications with bone-screw fixation due to the nature of the bone and types and projection geometries of the screws used, along with their methods of insertion. These complications include implant failure, screw loosening and pullout. Recent research suggests new cortical screws that project in an anteromediolateral direction have advantages over traditional screws projecting in an anteromedial direction. Embodiments of the present disclosure take this research into account and can be used in guiding and placing new cortical screws to project in an anteromediolateral direction in order to overcome many problems of traditional screws in osteoporotic patients. Further, embodiments of the present disclosure can be used to place multiple new cortical screws through a single incision, minimizing trauma to already sensitive osteoporotic patients.

The last steps in pedicle screw fusion can involve rod reduction and final tightening. Rod reduction is typically necessary if there is malalignment in the vertebral bodies such as spondylolisthesis. In this case, the malalignment can be realigned by pulling or pushing on the pedicle screw that is anchored into that vertebrate relative to other screws in other vertebrate. By adjusting the relative position of the screws heads, a preferably bent rod can be lowered into the screw heads and "reduce" the malalignment or spondylolisthesis. In open surgeries, the reduction process is usually performed by rod reduction tools that push the rod into the screw head. In MIS systems, extended threads on the tower or extended tab that extend higher than the screw head can reduce the rod into the screw head by allowing the locking cap to engage with the threads at a higher position thereby capturing the rod at a position higher up or farther away than the final seat of the screw head.

After the rod is reduced and the vertebrate are aligned, the rod can be locked into the screw heads by locking caps. The locking caps are usually tightened to the final torque using a counter-torque instrument. The counter-torque usually is a sleeve that passes over the screw head as well as blades or towers (if present). The counter-torque can have grooves that fit over the screw head and often also the rod in order to provide a counter force when the locking cap is final tightened. The counter-torque can stabilize the screw heads so that any rotation of the screw head during final tightening is minimized.

During the final tightening process, it is also common to provide compression of the screw heads. Compression during final locking is thought to help with the fusion process as any interbody fusion is thought to be more successful under pressure or compression. Compression also helps place pressure upon the interbody spacer and reduces the chance that the spacer will back out, retropulse, or migrate. Compression is also useful to restore lumbar lordosis. Many interbody spacers placed either anteriorly through an ALIF, laterally through an XLIF or DLIF, obliquely through OLIF (oblique lateral interbody fusion), or posteriorly through PLIF or TLIF all can have lordotic profiles. The new expandable cages allow even more significant lordosis. The compression during final tightening can optimize the lordosis through posterior compression during final locking.

Typical pedicle screw system use separate tools for screw insertion, screw alignment, rod insertion, cap insertion, rod reduction, counter-torque, and final tightening. These separate tools all require extra steps at each pedicle screw. Each extra step introduces more irritation of muscle and tissue as well as time. Thus, a system that allows a pedicle screw that is preattached to a tower system that can perform all these tasks without any extra tools is indeed time saving and optimal. Some embodiments disclosed herein describe a system of towers that are removably attached to pedicle screws. In some embodiments:

- Towers can cross paths without interference (in situations with lordosis);
- Towers can be used to align the screw heads without the need for a separate tool to straighten the screw heads;
- Towers can be used to measure the length and curvature of the rod;
- Towers can allow easy rod placement and visualization of the rods even in MIS approach and even in large patients where visualization is difficult;
- Towers can allow and/or facilitate rod reduction, and reduction of spondylolisthesis;
- Towers can allow final tightening under compression or distraction without a separate compression or distraction tool;
- Towers can provide counter-torque during final tightening without a counter-torque tool; and/or
- Towers attached to screws can be placed robotically and allow rod placement, rod reduction, compression, and final tightening with counter-torque all to be performed robotically through a mechanical coupling of parts of the tower system with robotic arms. The robot, navigation system, software can be configured to know the positions of all towers screws, rods and caps at all times.

The intersecting tower system of some embodiments disclosed herein can allow or provide an optimal MIS system where incision size and tissue damage is minimized, surgical steps are optimized, number of tools are minimized, and surgical time is reduced. Previous MIS tower systems are either placed in an awkward configuration where the screw trajectories are crossed due to lumbar lordosis with the towers angled to be parallel to each other. Otherwise, MIS towers are placed though a single incision and the towers are crossed next to each other, making rod insertion, and final tightening very difficult and frustrating. Some embodiments of the present disclosure can avoid these difficulties and can provide an optimized MIS pedicle screw system.

Some embodiments disclosed herein provide a simple method and associated apparatus to place two or more pedicle screws through one small hole. This provides a better cosmetic and functional result with just a single skin incision of small size (approximately 0.5 to 4 cm in length, approximately 0.5 to 3 cm in length, or approximately 1 to 2 cm in length) regardless of the number of screws used. In one embodiment, the single incision is smaller than the sum of the maximum widths of two respective largest elements for each screw that is inserted through the single incision, where an element includes the screw, screw head, rod, locking assembly and associated tools.

Some embodiments disclosed herein are configured to enable a surgeon or other user to insert, position, and manipulate a spinal implant such as a rod and a locking assembly through the same small incision in order to lock the rod within the screws. Certain embodiments provide novel ways to insert a rod into the heads of pedicle screws and ways to lock the rod within the screws through a single small incision. The systems and methods involve in certain embodiments the attachment of guide elements consisting of the following: one or more flexible wires, flexible yet firm extended blades, extended tabs, or towers attached to each pedicle screw head to be used to guide the rod down to the screw. The guide elements are configured and combined so that they can overlap or intersect at or below the skin incision, thereby enabling the use of a small, single skin incision. The screws, rods, and locking assemblies can all be placed through a single small incision and yet still be appropriately interconnected within because of the natural lordotic curvature of the lumbar spine. By attaching at least one guidance element on each side of the screw head, the guidance elements assist to align the screw head. The guidance elements also trap or restrict displacement of the rod, forcing it to fit between them and directly into the screw head.

Compared to U.S. Pat. No. 7,179,261 to Sicvol described above, embodiments of the present disclosure eliminate the need for “cut-outs” where the guide elements intersect. For example, in embodiments utilizing extended tabs or blades, these extended tabs or blades do not have a proximal, distal, or any lumen, and the configuration of guidance elements (extended tabs or blades) for screws at adjacent levels allow the tabs to intersect and overlap completely for any patient with any relative geometries. Thus interference between adjacent guidance elements on adjacent vertebrae is not a problem. Also, in the cut-out tubes taught by the ’261 Patent, a rod or other element would still have to be inserted through the tube at some point. The cut-out tubes require that the rod (or other inserted element) is oriented longitudinally parallel to the long axis of the tube as it is directed into the body until it reaches a section with side wall openings or slots distal to the cut-out section, at which point it may optionally be turned perpendicularly to the long axis and directed out of the side wall through the opening or slot. In embodiments of the present disclosure by using guidance elements such as extended blades or extended tabs (from the screw head), the element that is guided by them and inserted along them (e.g., a rod, a locking assembly etc.) does not have to be inserted through any lumen. When a rod is inserted using the blades, the blades can simply be fed through the outer edges of the rod body, through a retaining element or clasp attached to the rod body, or between the outer edges of the rod body and a retaining element (retention thread). Thus, it is possible for the inserted rod or other elements to be oriented perpendicular to the long axis or oriented in any other manner or at any angle during the entire entry pathway. This provides greater flexibility for avoiding interference between adjacent stabilization system pieces and eliminates the need for a surgeon to identify the cut-out sections before turning the screw/rod perpendicularly and/or reorienting it. Furthermore, since there are no lumens proximally or distally with the extended tabs, blades from adjacent levels may overlap and intersect without the need for cutout therefore allowing all blades to exit a single small minimal incision.

The guidance elements can also be used to guide the locking assemblies down to the screw heads for embodiments in which the locking assembly is not part of the screw head itself (and already down there).

Another embodiment is a hybrid system where each screw is placed through short towers or tubes that do not come to the skin surface. Wires, blade or tab extensions are attached to the top of the towers or tubes so that the screw, rod, locking assembly, and tools used for insertion, adjustment, locking, compression, distraction, and removal are guided by the extensions close to the skin but through individual towers or tubes close to the bone and pedicle screw. This hybrid system offers both the advantages of the wires/extended blades/tabs in which many guidance elements can overlap in a single incision at the skin level and the advantages of a tower or tube system are preserved at the bone level. Some surgeons who are comfortable with the tower system but who want the advantages of the blade/tab system may want to use this hybrid system.

Making some of the guidance elements telescopic allows for more guidance elements to fit through a single incision smoothly, thereby advantageously reducing the need to have a larger incision and/or multiple incisions. After insertion, the various guidance elements may be deployed telescopically as needed. Using telescoping components as part of the upwardly directed extended guidance elements allows a rod for stabilizing vertebrae to be inserted into the body through the telescoping components and through the same singular incision, minimizing invasiveness of the procedure.

All combinations and arrangements of towers, tubes, blades, arms, tabs, wires, and other upwardly directed extended guidance elements, either as described herein or in hybrid systems which combine conventional tower/guidance elements as described in the prior art (such as described in the references incorporated by reference throughout this specification) are contemplated as within the spirit and scope of the present disclosure. As used herein, the term guiding or guidance element is intended to include one or more components extending between a screw and a skin incision, preferably directly or indirectly coupled or detachably connected to a screw head, and includes both conventional towers or tubes such as those made of rigid or semi-rigid materials as described in the patents and publications incorporated by reference throughout this specification, as well as the additional embodiments of guiding or guidance elements as described herein. The most suitable selection and arrangement is for the surgeon to determine in each particular case. For example, in one embodiment, there may be telescoping tubes at one level, wires at the next level, and blades at the next level on one side (of the slot for the rod) with blades attached to wires on the other side (of the slot for the rod). Different variations may be selected for each side (medial, lateral) in order to introduce more components through the same incision. The goal is to provide enough guidance elements to properly guide the stabilization rods, locking assemblies, tools, etc. to the pedicle while minimizing the number of incisions and preventing overcrowding. Eliminating overcrowding permits proper visualization so that the surgeon can work comfortably and efficiently.

In some embodiments, a system is provided for performing spine stabilization through an opening in skin of a patient. In some embodiments, the opening may be a single, minimally invasive skin incision. The system comprises a first screw having a screw head and a first guiding element (also referred to herein as a first extension) comprising a height component detachably connected to the first screw, the first screw being configured for implantation in a first vertebra. The system also comprises a second screw having a screw head and a second guiding element detachably connected to the second screw, the second screw configured for implantation in a second vertebra. The first screw with the first guiding element and the second screw with the second guiding element can be delivered into the first and second vertebra.

Other objectives and advantages of embodiments of the disclosure will be set forth in the description which follows. Implicit modifications of the present disclosure based on the explicit descriptions will be, at least in part, obvious from the description, or may be learned by practice of the disclosure. Such subtle, predictable modifications and adaptations are taken to be within the scope of the present disclosure. Additional advantages of the disclosure may be realized and obtained by means of the instrumentalities and combinations particularly pointed out hereinafter.

Systems, Devices and Methods of FIGS. 1A-1G

Additional embodiments of a system (e.g., system 100) that can be used for stabilizing or treating spinal vertebrae through a skin incision S are disclosed below. In any embodiments disclosed herein, any components, features, or other details of the system 100 can have any of the components, features, or other details of any other system embodiments disclosed herein or be used according to any of the steps of any other method embodiments disclosed herein, including without limitation any of the embodiments of the system 200 or methods of use thereof described above, in any combination with any of the components, features, or details of the system 100 or methods of use disclosed herein. Similarly, any components, features, steps, or other details of any of the other system or method embodiments disclosed herein can have any of the components, features, steps, or other details of any embodiments of the system 100 or methods of use thereof disclosed herein in any combination with any of the components, features, or details of the system.

Some embodiments of the system 100 for stabilizing spinal vertebrae through a skin incision S can include a first screw 102 having a first screw head, a second screw 104 having a second screw head, a third screw 106 having a third screw head, a first tower 112 having a distal portion 112*a* and a proximal portion 112*b*, a second tower 114 having a distal portion 114*a* and a proximal portion 114*b*, and a third tower 116 having a distal portion 116*a* and a proximal portion 116*b*. Note that the first tower, second tower, and third tower can also be referred to herein as a first extension, second extension, and third extension. The first tower 112 can be configured to be removably coupled with the first screw 102 at a distal portion 112*a* of the first tower 112, the second tower 114 can be configured to be removably coupled with the second screw 104 at a distal portion 114*a* of the second tower 114, and third tower 116 can be configured to be removably coupled with the third screw 106 at a distal portion 116*a* of the third tower 116. In some embodiments, each of the first, second, and third screws 102, 106, 104 can be positioned in different vertebra. In some embodiments, each of the first, second, and third screws 102, 106, 104 can be positioned in adjacent vertebra. In any embodiments disclosed herein, any of the extensions can also be referred to as guiding elements, towers, or by other suitable terms understood in the industry. In some embodiments, the third screw may be positioned in a vertebrae between the first and second screws. Additionally, note that, while the embodiments of the system 100 disclosed herein may have included screws as part of the system, any embodiments of the system 100 disclosed herein can exclude the screws such that the embodiments of the system 100 include the towers and/or other components other than the screws.

Some MIS pedicle screw systems use towers mechanically coupled to pedicle screws while other MIS pedicle screw systems use extended tabs or blades that are created in a single piece of metal. In the extended tabs case the blades are manufactured as part of the screw from one single piece of metal. There is usually a scored transition between the top of the screw and the extended blade. The scored transition allows the blade to snap off at the end of the fusion after the rod has been final locked in place. From a manufacturing perspective, extended tabs or blades are more expensive because of the extra metal needed to manufacture the blade or tab that is eventually broken off and wasted.

In any of the embodiments disclosed herein, the first, second, and third towers can be configured to be removably coupled with the screw heads and otherwise configured to be reuseable. This can save a significant cost as compared with disposable blade designs that, once the blade has been separated from the screw head, is typically discarded and not reused. From a surgical perspective, towers are more firm an rigid and can be used to provide rigidity to as to provide counter-torque during final tightening of the locking cap onto the rod in the screw head. Extended blades usually do not have the same strength as a counter-torque device. The towers of any of the embodiments disclosed herein, with the rigidity that they provide, can therefore help prevent the walls of the pedicle screw from splaying during final tightening of the locking cap.

The towers of some embodiments disclosed herein can provide a more complete enclosure than the blades or tabs can, due to the additional wall portions of the towers that extend between the sides of the towers. In some embodiments, as shown in the figures, the wall portions that extend between the two side wall portions to provide additional strength and stiffness can be integrally formed with the side wall portions, or can be separately formed and coupled (removably or nonremovably) with the side wall portions to provide additional rigidity to the towers.

In some embodiments, at least a portion of the distal portions of any embodiments of the first and/or second towers 112, 114 can be enclosed about at least 320° (or at least approximately 320°) of the circumference or cross-section of the first and/or second towers 112, 114, or from 270° (or approximately 270°) to 330° (or approximately 330°, or at least 330°), or from 290° (or approximately 290°) to 320° (or approximately 320°), or enclosed about any value or range of value within the foregoing ranges. In some embodiments, at least a portion of the distal portions of any embodiments of the first and/or second towers 112, 114 can be completely enclosed, with the exception of the channel extending lengthwise along at least the distal portion of the first and/or second towers 112, 114 sized and configured to permit a passage of the rod or connecting element toward the screws. Additionally, for example and without limitation, at least a portion of the distal portion of any embodiments of the third tower 116 can be enclosed about at least 270° (or at least approximately 270°) of the circumference or cross-section of the third tower 116, or from 240° (or approximately 240°) to 320° (or approximately 320°), or from 270° (or approximately 270°) to 300° (or approximately 300°), or enclosed about any value or range of value within the foregoing ranges. In some embodiments, at least a portion of the distal portion of any embodiments of the third tower 116 can be completely enclosed, with the exception of a channel on each side of the distal portion **116*b* of the third tower 116 extending lengthwise along at least the distal portion of the third tower 116** sized and configured to permit a passage of the rod or connecting element toward the screws.

In some embodiments, at least a portion of the distal portions of any embodiments of the first and/or second towers 112, 114 can be enclosed about at least 80% (or at least approximately 80%) of the circumference or cross-section of the first and/or second towers 112, 114, or from 70% (or approximately 70%) to 90% (or approximately 90%, or more than 90%—e.g., 95% or 100%), or from 75% (or approximately 75%) to 85% (or approximately 85%), or enclosed about any value or range of value within the foregoing ranges. Additionally, for example and without limitation, at least a portion of the distal portion of any embodiments of the third tower 116 can be enclosed about at least 75% (or at least approximately 75%) of the circumference or cross-section of the third tower 116, or from 60% (or approximately 60%) to 80% (or approximately 80%), or from 65% (or approximately 65%) to 75% (or approximately 75%), or enclosed about any value or range of value within the foregoing ranges.

The additional wall portions of the towers disclosed herein are configured to prevent more muscle and tissue creep or invagination into the space within the tower or between the blades. For an MIS procedure in a large patient with excessive tissue, adipose tissue and muscle, a tower will protect the inside of the tower from tissue interference, whereas blades can allow tissue to creep in from both openings between the blades. In some embodiments, placement of the rod is then easier within a tower than using blades and there is a lower risk that patient tissue will be inadvertently severed or injured during rod placement. Placement of the rod using only blades often results in the rod getting "caught up" in the muscle that creeps into the opening between the blades.

In some embodiments, the first tower 112 can have a slight bend between the distal portion **112*a* and the proximal portion 112*b* thereof. For example and without limitation, the distal portion 112*a* can be angled relative to the proximal portion 112*b* so that a longitudinal centerline of the proximal portion 112*b* has an angle that is 20° or approximately 20° relative to a longitudinal centerline of the distal portion 112*a* of the first tower 112, or so that the longitudinal centerline of the proximal portion 112*b* has an angle that is from 0° or approximately 0° to 40° or approximately 40°, or from 10° or approximately 10° to 30° or approximately 30° relative to the longitudinal centerline of the distal portion 112*a*** of the first tower, or of any value or range of values within any of the foregoing ranges.

In some embodiments, the second tower 114 can have a bend between the distal portion **114*a* and the proximal portion 114*b* thereof. The bend in the third tower 114 may be greater than the bend in the first tower 112. For example and without limitation, the distal portion 114*a* can be angled relative to the proximal portion 114*b* so that a longitudinal centerline of the proximal portion 114*b* has an angle that is 85° or approximately 85° relative to a longitudinal centerline of the distal portion 114*a* of the second tower 114, or that is 90° or approximately 90° relative to a longitudinal centerline of the distal portion 116*a* of the second tower 114, or so that the longitudinal centerline of the proximal portion 114*b* has an angle that is from 70° or approximately 70° to 110° or approximately 110°, or from 80° or approximately 80° to 100° or approximately 100° relative to the longitudinal centerline of the distal portion 116*a* of the first tower 112, or of any value or range of values within any of the foregoing ranges. In some embodiments, the bend between the distal and proximal portions of any of the towers can optionally be adjustable using an adjustable coupling such as a locking hinge. In any embodiments, the third tower 116 can be generally straight along a length thereof, as shown, or can have a bend between the distal portion 116*a* and the proximal portion 116*b*** thereof.

Any embodiments of the system 100 disclosed herein can be configured such that the first screw 102, the second screw 104, and the third screw 106 can be implanted through the same skin incision S. Further, in any embodiments, a distal portion **114*a* of the third tower 116 can be positioned between the distal portions 112*a*, 114*a* of the first and second towers 112, 114 in an operable state of the system 100**.

The first tower 112, the second tower 114, and the third tower 116 can each have a length extending from a proximal end to a distal end. The proximal ends of the first tower 112, the second tower 114, and/or the third tower 116 can face a physician. In some examples, the proximal ends of the first tower 112, the second tower 114, and/or the third tower 116 can be configured to be manipulated by a physician. For example, one or more of the proximal ends of the first tower 112, the second tower 114, and/or the third tower 116 can form a handle. The distal ends of the first tower 112, the second tower 114, and/or the third tower 116 can face a patient. In some examples, the distal ends of the first tower 112, the second tower 114, and/or the third tower 116 can be configured to engage the patient. For example, the distal ends of the first tower 112, the second tower 114, and/or the third tower 116 can include the first screw 102, the second screw 104, and the third screw 106, respectively.

In some embodiments, two or more of the first tower 112, the second tower 114, and the third tower 116 can have a proximal portion extending away from the corresponding distal portion at a variety of angles. For example, in some examples, the first tower 112 can have a proximal portion **112*b* extending away from the distal portion 112*a* of the first tower 112 at a first angle. Additionally and/or alternatively, in some examples, the second tower 114 can have a proximal portion 114*b* extending away from the distal portion 114*a*** of the second tower at a second angle. Accordingly, two or more proximal portions can extend away from the corresponding distal portion to provide two or more separate handles extending away from the respective distal portions that a surgeon can grasp and manipulate.

Each of the first tower 112, the second tower 114, and the third tower 116 can arranged along a respective plane. For example, an axial or longitudinal axis of the proximal portions of the towers and an axial or longitudinal centerline C of the respective distal portions can be coplanar regardless of the bends and/or angles between the proximal portions and the distal portions. In some examples, the first tower 112 can have a proximal portion 112*b* extending away from the distal portion 112*a* of the first tower 112 at a first angle along a first plane. Additionally and/or alternatively, in some examples, the second tower 114 can have a proximal portion 114*b* extending away from the distal portion 114*a* of the second tower at a second angle along a second plane. Furthermore, the third tower 116 can have an axial or longitudinal centerline C extending from the distal portion 116*a* to the proximal portion 116*b* along a third plane. In some examples, the first tower 112, the second tower 114, and the third tower 116 can be coplanar in an operative state. For example, as shown in FIGS. 1A-1G, the towers can be coplanar in the operative state. Accordingly, the first plane, the second plane, and the third plane can be coplanar in the operative state. In some examples, the first tower 112, the second tower 114, and the third tower 116 can be coplanar along the direction of the patient's spine as shown in FIG. 4C.

In some embodiments, the first tower 112 can removably couple with the first screw 102 such that, when the first tower 112 is coupled with the first screw 102, the axial or longitudinal centerline C of the distal portion 112*a* of the first tower 112 is approximately collinear with an axial or longitudinal centerline C of the first screw 102. The second tower 114 can removably couple with the second screw 104 such that, when the second tower 114 is coupled with the second screw 104, an axial centerline C of the distal portion 114*a* of the second tower 114 is approximately collinear with an axial centerline C of the second screw 104. The third tower 116 can removably couple with the third screw 106 such that, when the third tower 116 is coupled with the third screw 106, an axial centerline C of the distal portion 116*a* of the third tower 116 is approximately collinear with an axial centerline C of the third screw 106. In any embodiments, the first tower 112 can be shorter than the second tower 114 or the third tower 116, longer than the second tower 114 or the third tower 116, or have approximately the same length as the second tower 114 or the third tower 116, and the second tower 114 can be shorter than the third tower 116, longer than the third tower 116, or have approximately the same length as the third tower 116.

In some embodiments, the angle between the proximal portion 112*b* and distal portion 112*a* of the first tower 112 can be adjustable, an angle between the proximal portion 114*b* and distal portion 114*a* of the second tower 114 can be adjustable, and/or the angle between the proximal portion 116*b* and distal portion 116*a* of the third tower 116 can be adjustable. A common mechanism for adjustability is a gear or ratchet mechanism. In this way, the proximal portion of any of the extensions can be angled away from the centerline of the distal portion of the respective screw. By adjusting the angle, there may be more room to place the rod and locking caps. Also, by adjusting the angle, it may be easier for a surgeon to grip both proximal portions of the towers in order to squeeze the two or three proximal portions of the extensions in order to compress the heads of screws when locking the caps onto the connecting element or rod connecting the screw heads. In another embodiment, proximal portions 112*b*, 114*b*, and/or 116*b* can be detachable from the distal portions 112*a*, 114*a*, and/or 116*a*. In this manner, proximal portions with different angles in relation to centerline of the respective distal portions can be switched as needed and reconnected to the distal portions of the extensions.

Figure 1B:
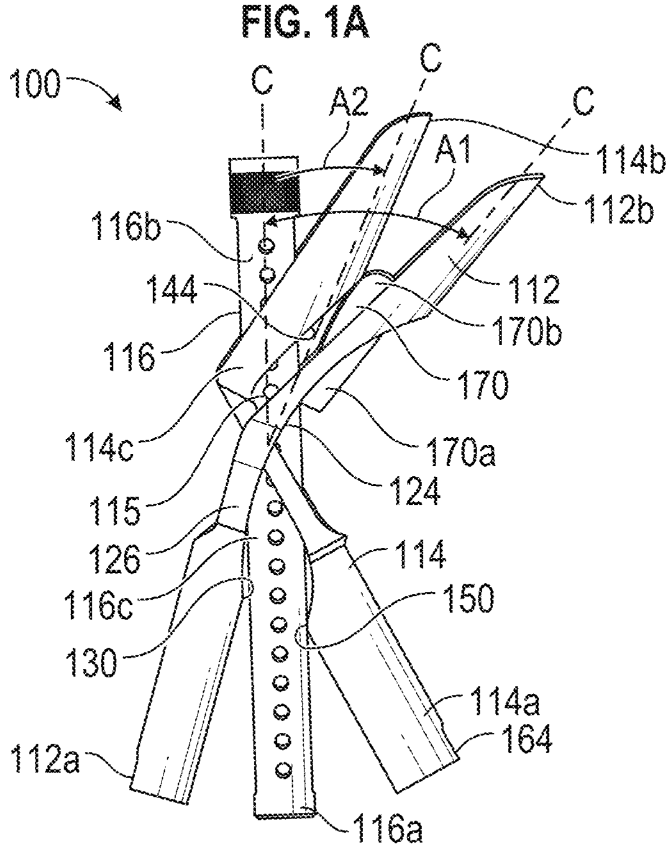
Figure 1C:
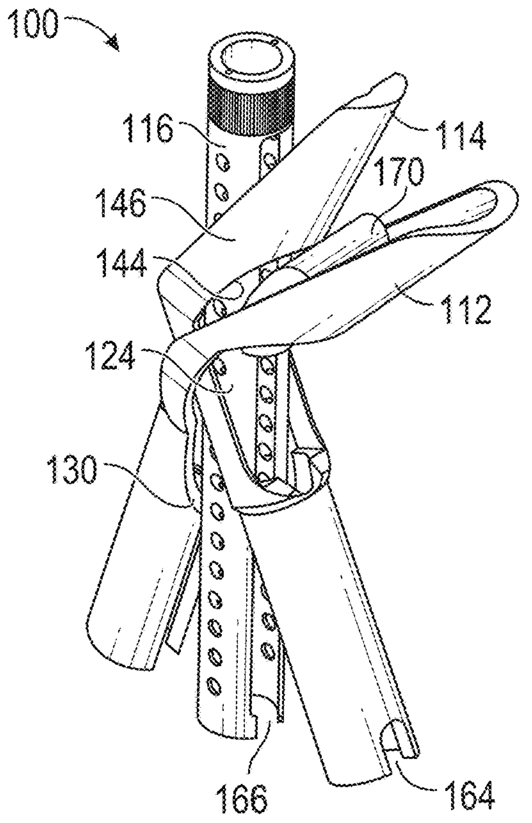
Figure 1D:
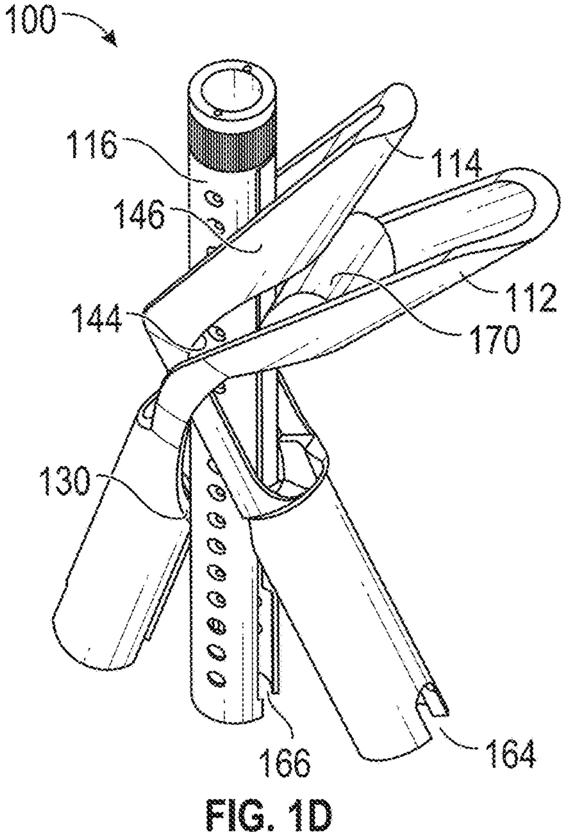
Figure 1G:
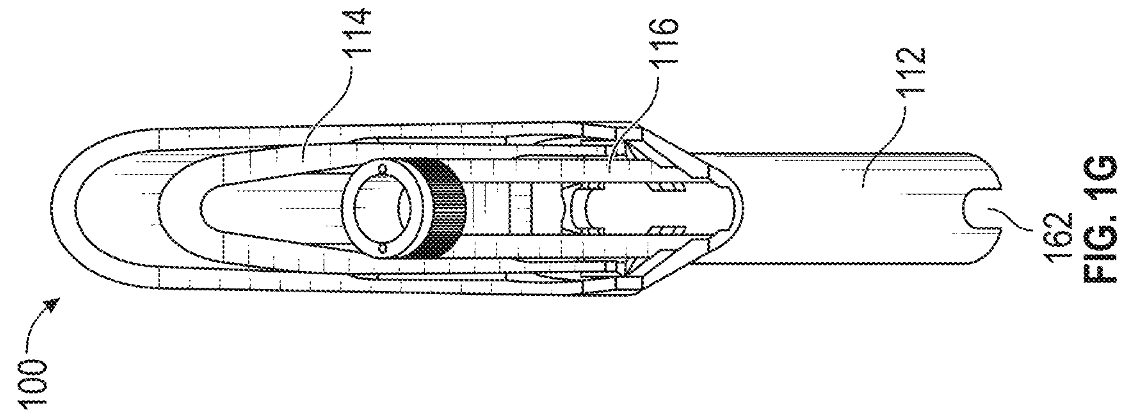
Figure 1F:
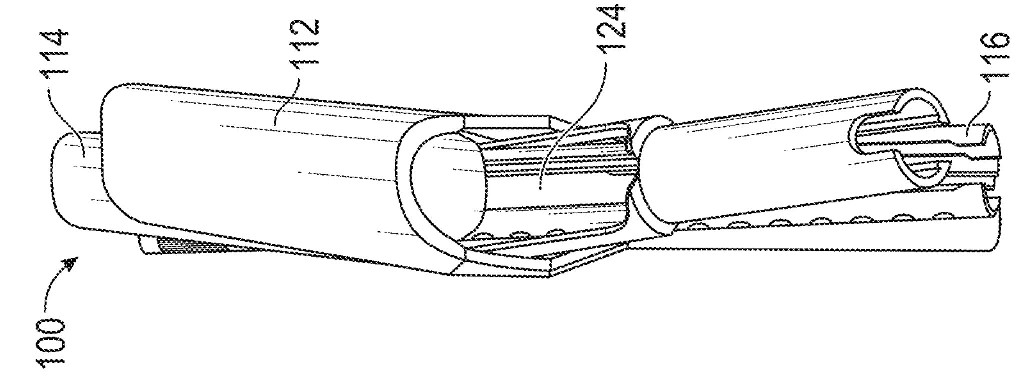
Figure 1E:
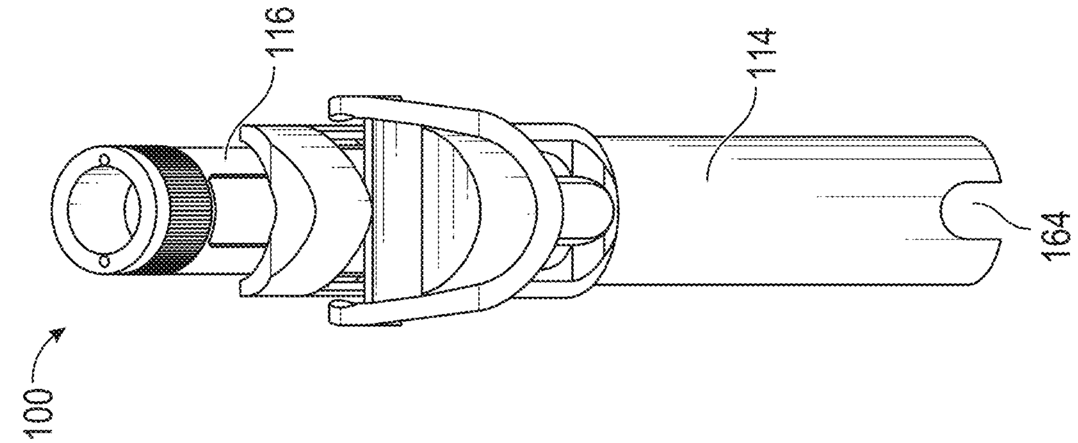

As mentioned, in some embodiments, the proximal portion 112*b* of the first tower 112 can extend at an angle away from the axial centerline C of the distal portion 112*a* of the first tower 112 such that an axial centerline of the proximal portion 112*b* of the first tower 112 is not approximately collinear with an axial centerline of the distal portion 112*a* of the first tower 112. Further, the first tower 112 can be configured such that, in an operable state, an axial centerline of the proximal portion 112*b* of the first tower 112 can extend at an angle away from the axial centerline C of the proximal portion of the third tower 116 so that the axial centerline of proximal portion 112*b* of the first tower 112 forms an acute angle A1 relative to the axial centerline of the proximal portion of the third tower 116, as shown in FIG. 1B. In some embodiments, the angle A1 can be 50° (or approximately 50°), or from 40° (or approximately 40°) or less to 70° (or approximately 70°) or more. The second tower 114 can be configured such that, in an operable state, an axial centerline of the proximal portion 114*b* of the second tower 114 can extend at an angle away from the axial centerline C of the proximal portion of the third tower 116 so that the axial centerline of proximal portion 114*b* of the second tower 114 forms an acute angle A2 relative to the axial centerline of the proximal portion of the third tower 116 in an operable state, as shown in FIG. 1B. In some embodiments, the angle A2 can be 50° (or approximately 50°), or from 40° (or approximately 40°) or less to 70° (or approximately 70°) or more.

In some embodiments, the first tower 112 can be angled such that, in an operable state, the proximal portion 112*b* of the first tower 112 can extend away from the proximal portion 116*b* of the third tower 116 in a first direction, and the second tower 114 can be angled such that, in an operable state, the proximal portion 114*b* of the second tower 114 can also extend away from the proximal portion of the third tower 116 in the same direction or approximately the same direction as the proximal portion 112*b* of the first tower—e.g., in the first direction. In some embodiments, the axial centerlines of the proximal portions 112*b*, 114*b* of the first and second towers 112, 116 can be within the same plane (e.g., a first plane) when the proximal portions 112*b*, 114*b* of the first and second towers 112, 114 extend away from the proximal portion of the third tower 116 in the same direction. The first plane that contains the axial centerlines of the proximal portions 112*b*, 114*b* of the first and second towers 112, 114 can also intersect with the axial centerline of the third tower 116, in some embodiments.

In some embodiments, the first tower 112 can be sized and configured such that, in an operable state, the proximal portion 112*b* of the first tower 112 can extend away from the skin incision S toward the surgeon. In some embodiments, the first, second, and third towers 112, 114, and 116 can be sized and configured such that the level of the patient's skin in an operable state of the system 100 will be at or adjacent to the bend 152 (e.g., just below the bend 152) formed in the second tower 114. In some embodiments, the distal portion 112*a* of the first tower 112 and the distal portion 114*a* of the second tower 114 can extend away from the first screw 102 and the second screw 104 to a height just below the skin incision S, or to a height level with the skin of a patient, when the first and second screws 102, 104 are fully implanted in a first vertebra and a second vertebra, respectively.

In some embodiments, the first tower 112 can be sized such that only the proximal portion 112*b* of the first tower 112 is outside of the skin incision S when the first screw 102 is implanted in a first vertebra, and the second tower 114 can be sized such that only the proximal portion 114*b* of the second tower 114 is outside of the skin incision S when the second screw 104 is implanted in a second vertebra. In any embodiments, the third tower 116 can be sized to extend completely through the skin incision S when the third screw 106 is implanted in a third vertebra. In some embodiments, the third vertebra is positioned between the first and second vertebrae.

The proximal portion 112*b* of the first tower 112 and the proximal portion 114*b* of the second tower 114 can be configured to be grasped by a surgeon to enable a surgeon to exert a rotational force on the first tower 112 about at least the axial centerline C of the distal portion 112*a* of the first tower 112 about at least the axial centerline C of the distal portion 112*a* of the first tower 112 and/or a torque force on the first tower 112 so as to cause the first tower 112 to rotate about an axis that is perpendicular to an axial centerline C of the distal portion 112*a* of the first tower 112. The proximal portion 114*b* of the second tower 114 and the proximal portion 114*b* of the second tower 116 can be configured to be grasped by a surgeon to enable a surgeon to exert a rotational force on the second tower 114 about at least the axial centerline C of the distal portion 114*a* of the second tower 114 about at least the axial centerline C of the distal portion 114*a* of the second tower 114 and/or a torque force on the second tower 114 so as to cause the second tower 114 to rotate about an axis that is perpendicular to an axial centerline C of the distal portion 114*a* of the second tower 114.

The proximal portion 112*b* of the first tower 112 can have a length that is approximately the same as a length of the distal portion 112*a* of the first tower 112, or can have a length that is at least 80% or less of a length of the distal portion 112*a* of the first tower 112. In some embodiments, the proximal portion 112*b* of the first tower 112 can be removably coupled with the distal portion 112*a* of the first tower 112. In other embodiments, the proximal portion 112*b* of the first tower 112 can be non-removably coupled with the distal portion 112*a* of the first tower 112. For example and without limitation, the proximal portion 112*b* of the first tower 112 can be integrally formed with the body portion of the first tower 112. In any embodiments, the second and third towers 114, 116 can be similarly configured.

In some embodiments, at least the distal portion 112*a*, the proximal portion 112*b* of the first tower 112, and/or the third tower 116 can have a tubular or half-tubular shape. The first tower 112 can have a cutout 124 formed through a wall portion 126 of the first tower 112, the cutout 124 being configured to receive a portion of an outside surface 116*c* of the third tower 116 therein in an operable state, as shown in the figures. In some embodiments, the cutout 124 of the first tower 112 can be large enough to also receive a portion of an outside surface 114*c* of the second tower 114 therein in an operable state, as shown in the figures. In some embodiments, the cutout 124 can extend at least through a proximal end 112*c* of the distal portion 112*a* of the first tower 112. The cutout 124 can extend entirely through the first tower 112 and be sized and configured such that, in an operable state, the screw coupled with the second tower 214 and at least the distal portion 114*b* of the second tower 114 can pass entirely through the cutout 124 in the first tower 112 and the screw coupled with the third tower 116 and the distal portion 116*b* of the third tower 116 can pass entirely through the cutout 124.

In some embodiments, the cutout 124 can extend entirely through the first tower 112 such that, in an operable state, the third tower 116 can pass entirely through the cutout 124 and such that the wall portion 126 of the first tower 112 completely and continuously surrounds the outside surface 116*c* of a portion of the third tower 116 and the outside surface 114*c* of a portion of the second tower 114. Some embodiments of the cutout 124 can have a distal edge 130. In some embodiments, the distal edge 130 can be lower to allow for a wider range of rotation or movement of the first tower 112 relative to the second tower 114. In some embodiments, the cutout 124 can extend distally to be near to or adjacent to the distal end of the first tower. Some embodiments of the cutout 124 can have an elongated or ovular shape.

In some embodiments, at least the distal portion 114*a* and the proximal portion 114*b* of the second tower 114 can have a tubular or half-tubular shape. The second tower 114 can have a cutout 144 formed through a wall portion 146 of the second tower 114, the cutout 144 being configured to receive a portion of an outside surface 116*c* of the third tower 116 therein in an operable state, as shown in the figures. In some embodiments, the cutout 144 can extend at least through a proximal end 114*b* of the distal portion 114*a* of the second tower 114. The cutout 144 can extend entirely through the second tower 114 such that, in an operable state, the third tower 116 and the screw coupled with the third tower 116 can pass entirely through the cutout 144 in the second tower 114.

In some embodiments, the cutout 144 can be configured such that, in an operable state, the third tower 116 can pass entirely through the cutout 144 and such that the wall portion 146 of the second tower 114 completely and continuously surrounds the outside surface 116*c* of a portion of the third tower 116. Further, some embodiments of the cutout 144 can have a distal edge 150. In some embodiments, the distal edge 150 can be lower to allow for a wider range of rotation or movement of the second tower 114 relative to the third tower 116. In some embodiments, the cutout 144 can extend distally to be near to or adjacent to the distal end of the tower (e.g., the second tower 114). Some embodiments of the cutout 144 can have an elongated or ovular shape.

In some embodiments, at least the distal portion 112*a* of the first tower 112, the distal portion 114*a* of the second tower 114, and/or the distal portion 116*a* of the third tower 116 can have an adjustable length. Further, some embodiments of the first tower 112, the second tower 114, and the third tower 116 can be generally cylindrically shaped. Other embodiments can have any other desired cross-sectional shape, including a generally square shape, a triangular cross-sectional shape, on ovular cross-sectional shape, a polygonal cross-sectional shape, or any combination of the foregoing.

The proximal portion 112*b* of the first tower 112 and/or the proximal portion 114*b* of the second tower 114 can have a cross-sectional profile that can have a curved shape. Further, the proximal portion 112*b* of the first tower 112 and/or the proximal portion 114*b* of the second tower 114 can have a cross-sectional profile that can have a semi-circular tubular shape. In some embodiments, the proximal portion 112*b* of the first tower 112 and/or the proximal portion 114*b* of the second tower 114 can have a cross-sectional profile that is approximately the same as one-half of the distal portion 112*a* of the first tower 112 and one-half of the distal portion 114*a* of the second tower 114. In some embodiments, the proximal portion 112*b* of the first tower 112 and/or the proximal portion 114*b* of the second tower 114 can have a planar shape.

Any of the embodiments of the system 100 disclosed herein can have a rigid connecting element (not shown), similar to any of the other embodiments of the connecting elements disclosed herein, that can be implanted using any desired shape and configuration of a connecting element implantation device, or implanted using any other devices or methods disclosed herein or other desired devices or methods. A first receiving element coupled with the head of the first screw 102, a second receiving element coupled with the head of the second screw 104, and a third receiving element coupled with the head of the third screw 106 can secure the connecting element to the screws 102, 104, 106. The first, second, and third receiving elements can be configured to operably receive the connecting element that, in an operable state, can extend between the first, second, and third receiving elements when the first screw 102, the second screw 104, and the third screw 106 are implanted in a first vertebra, a second vertebra, and a third vertebra, respectively.

In some embodiments, the first tower 112 can have at least one window or slot 162 extending through a side of the body portion thereof, the at least one slot 162 configured to receive a connecting element 151 or configured to permit a passage of a connecting element 151 therethrough. Further, the second tower 114 can have at least one slot or window 164 extending through a side of the body portion of the second tower 114, the at least one slot 164 of the second tower 114 configured to receive the connecting element 151 that is configured to extend between the first screw 102 and the second screw 104 in an operable state. The third tower 116 can have at least one slot or window 166 extending through a side of the body portion of the third tower 116, the at least one slot 166 of the third tower 116 configured to receive the connecting element 151 that is configured to extend between the first screw 102 and the second screw 104 in an operable state. Lengthwise slots or channels can be formed in at least the distal portions of each of the first, second, and third towers to permit the connecting element to pass distally toward the screws.

In some embodiments of the system 100, the first tower 112 can have an insert or projection 170 formed thereon or coupled therewith. The projection 170 can have a distal portion 170*a* that, in some embodiments, in an operable state, contacts the outside surface 116*c* of the third tower 116 to provide a point or a region of contact between the proximal portion 112*b* of the first tower 112 and the proximal portion 116*b* of the third tower 114. In some embodiments of this configuration, as the proximal portion 112*b* of the first tower 112 is squeezed relative to or otherwise rotated or moved toward the proximal portion 116*b* of the third tower 116, the distal portion 170*a* of the projection 170 can contact the outside surface 116*c* of the third tower 116 and the distal portion 112*a* of the first tower 112 can be moved toward the distal portion 116*a* of the third tower 116 to cause a compressive force to be exerted on a first vertebra that the first tower 112 is coupled with relative to a third, adjacent vertebra that the third tower 116 is coupled with. In other embodiments, the projection 170 can be configured to rotate or otherwise move so that the point or region of contact and rotation between the first and third towers 112, 116 is only at the distal edge 130 of the opening. In some embodiments of this configuration, as the proximal portion 112*b* of the first tower 112 is moved away from the proximal portion 116*b* of the third tower 116, the distal portion 112*a* of the first tower 112 can be moved away from the distal portion 116*a* of the third tower 114 to cause a traction force to be exerted on a first vertebra that the first tower 112 is coupled with relative to a third, adjacent vertebra that the third tower 116 is coupled with.

In some embodiments, the projection 170 can be removably inserted into an interior space of the proximal portion 112*b* of the first tower 112 and positioned between the proximal portion 112*b* of the first tower 112 and the proximal portion 114*b* of the second tower 114, when needed or desired, to provide a fulcrum between the first and second towers 112, 114 during compression. In other embodiments, the projection 170 can be nonremovably coupled with the proximal portion 112*b* of the first tower 112 or integrally formed with the proximal portion 112*b* of the first tower 112, or nonremovably coupled with an outside surface of the proximal portion 114*b* of the second tower 114 or integrally formed with the proximal portion 114*b* of the second tower 114 so as to be between the proximal portion 114*b* of the second tower 114 and the proximal portion 112*b* of the first tower 112.

In some embodiments, the projection 170 can be configured to contact the outside surface 114*c* of the second tower 114, for example, in a proximal portion 114*b* of the second tower 114, to provide a point or a region of contact and rotation, or a fulcrum, between the proximal portion 112*b* of the first tower 112 and the proximal portion 114*b* of the second tower 114. In some embodiments of this configuration, as the proximal portion 112*b* of the first tower 112 is squeezed relative to or otherwise rotated or moved toward the proximal portion 114*b* of the second tower 114, a proximal portion 170*b* of the projection 170 can contact the outside surface 114*c* of the proximal portion 114*b* of the second tower 114 to provide the point or a region of contact and rotation, or a fulcrum, between the proximal portion 112*b* of the first tower 112 and the proximal portion 114*b* of the second tower 116 to cause a compressive force to be exerted on a first vertebra that the first tower 112 is coupled with relative to a second vertebra that the second tower 114 is coupled with. In other embodiments, one or more rings, shafts, pins, pegs, and/or other mechanical connectors can be used to create the point or region of rotation, or fulcrum, between the first, second, and/or third towers 112, 114, 116. For example and without limitation, with reference to FIG. 1B, a peg or a pair of pegs or pins advanced into the opening 115 passing through the third tower 116 that extends radially outwardly away from the outside surface 116*c* of the third tower 116 could be used to provide a pivot point or fulcrum between the first tower 112 and the second tower 114. The peg(s) or pin(s) that can extend through the openings 115 can be used in lieu of the projection 170 to provide the fulcrum between the first and second towers 112, 114. In some embodiments of this configuration, as the proximal portion 112*b* of the first tower 112 is moved away from the proximal portion 114*b* of the second tower 114, the system 100 can be configured to cause the distal portion 112*a* of the first tower 112 to move away from the distal portion 114*a* of the second tower 114 to thereby cause a traction force to be exerted on a first vertebra that the first tower 112 is coupled with relative to a second vertebra that second third tower 114 is coupled with.

In some embodiments, the first, second, and third towers 112, 114, 116 can be configured to be selectively removable from the first, second, and third screws 102, 104, 106. For example and without limitation, some embodiments of the first, second, and third towers 112, 114, 116 can have one or more creases, fracture lines, or lines of weakness (for example, two creases, fracture lines, or lines of weakness) along a length of a wall portion of any or all of the first, second, and third towers 112, 114, 116. In some embodiments, a tool or other device can be used to fracture the first, second, and third towers 112, 114, 116 along the one or more creases, fracture lines, or lines of weakness to remove the first, second, and third towers 112, 114, 116 from the first, second, and third screws 102, 104, 106. In some embodiments, the one or more creases, fracture lines, or lines of weakness can be circumferentially arranged and positioned at or adjacent to a top surface of the screws that the towers are attached to so that the towers can break along the one or more creases, fracture lines, or lines of weakness at or adjacent to the screws and be removed.

In some embodiments, the first, second, and third towers 112, 114, 116 can have distal end portions having circumferential, helical, and/or discrete/intermittent projections, tabs, lip(s), flanges, grooves, channels, detents, or other mechanically locking features that engage with complementary locking features of the screw heads to cause the first, second, and third towers 112, 114, 116 to be coupled with the screw heads when the first, second, and third towers 112, 114, 116 are intact, but which can each be decoupled from the complementary locking features of the screw heads when the first, second, and/or third towers 112, 114, 116 are fractured or split apart. As another example, a third wall or connecting wall connecting two sides of any of the first, second, and/or third towers 112, 114, 116 can have an angled or "V" shaped profile wherein a fracture line or line of weakness extends along the apex or angle of the angled or "V" shaped profile such that, when the two sides of the first, second, and third towers 112, 114, 116 are squeezed toward one another, such force from the squeezing can cause a fracture along the fracture line or line of weakness in the connecting portion, thereby allowing the first and second sides of the tower to separate so that tower can be removed from the screw head. In some embodiments, a slider ring can be slid down the tower to cause the two sides of the tower to be squeezed toward one another. In some embodiments, the first, second, and third towers 112, 114, 116 can have tabs that extend from the first, second, and third screw heads that can be broken off from the screw heads after implantation. In some embodiments, the first, second, and/or third towers can be removably coupled with the first, second, and/or third screws by rotating the first, second, and/or third towers into engagement with the first, second, and/or third screws, and removed in the opposite manner.

In other embodiments, the extensions can be removably coupled with the screws so that the entire extension can be removed from the screw and the patient intact and be reused in subsequent procedures. For example and without limitation, ball and detent removable coupling mechanisms can be used to removably couple the first, second, and third towers 112, 114, 116 with the first, second, and third screw heads. Other conventional or desired coupling mechanisms can be used to removably couple the first, second, and third towers 112, 114, 116 with the first, second, and third screw heads. In other embodiments, a plurality of wires can be used to removably couple the first, second, and third towers 112, 114, 116 with the first, second, and third screw heads.

Some embodiments of methods for treating a spinal defect include implanting a first screw 102 that is coupled with a first tower 112 through the incision into a first vertebra, advancing a second tower 114 that is coupled with a second screw 104 through the cutout 124 formed in the first tower 112 and implanting the second screw 104 into a second vertebra, and advancing a third tower 116 that is coupled with a third screw 106 through the cutout 144 formed in the second tower 114 and implanting the third screw 106 into a third vertebra. In some embodiments, the third vertebra can be between the first and second vertebrae.

The surgeon or medical practitioner can move a proximal portion 112*b* of the first tower 112 toward a proximal portion 114*b* of the second tower 114 to cause the distal portion 112*a* of the first tower 112 to move toward the distal portion 114*a* of the second tower 114, thereby causing a compressive force to be applied between the first, second, and third vertebrae. In some embodiments, the method can further include coupling a rigid connector or rod with the first screw 102, the second screw 104, and the third screw 106 to generally fix a position of the first screw 102 relative to the second screw 104 and the third screw 106. Thereafter, the first, second, and third towers 112, 114, 116 can be removed from the first, second, and third screws 102, 104, 106.

Any embodiments of the system 100 disclosed herein can be configured for use in performing L4, L5 and S1 surgical procedures, as well as cortical screw trajectory procedures. Additionally, any embodiments of the system 100 disclosed herein can be configured to enable compression, traction, and/or counter-torque all with one device, and the extensions can be configured to allow a tower, rod insertion, and rod reducer (using extended tabs with threads) with one device.

Certain aspects of the systems, devices, components and/or methods described above or as illustrated with respect to FIGS. 1A-1G are also encompassed by the following numbered embodiments. These numbered embodiments are considered to be directed to systems, devices, components and/or methods that include but are not limited to the embodiments of FIGS. 1A-1G, and thus these numbered embodiments may encompass other embodiments as described throughout this specification. Additionally, note that, while the embodiments of the system disclosed below may be described as including screws, any of the following embodiments may exclude any and all screws such that the embodiments only include the first tower, the second tower, and the third tower, plus any other components other than the screws (e.g., connecting element).

1. A system for stabilizing spinal vertebrae through a skin incision, comprising:
   - a first screw having a first screw head, a second screw having a second screw head, and a third screw having a third screw head;
   - a first tower having a distal portion and a proximal portion, the first tower being configured to be removably coupled with the first screw at a distal end of the first tower;
   - a second tower having a distal portion and a proximal portion, the second tower configured to be removably coupled with the second screw at a distal end of the second tower; and
   - a third tower having a distal portion and a proximal portion, the third tower being configured to be removably coupled with the third screw at a distal end of the third tower;
   - wherein:
     - the first tower is configured to removably couple with the first screw such that, when the first tower is coupled with the first screw, an axial centerline of the distal portion of the first tower is approximately collinear with an axial centerline of the first screw;
     - the second tower is configured to removably couple with the second screw such that, when the second tower is coupled with the second screw, an axial centerline of the distal portion of the second tower is approximately collinear with an axial centerline of the second screw;

the third tower is configured to removably couple with the third screw such that, when the third tower is coupled with the third screw, an axial centerline of the distal portion of the third tower is approximately collinear with an axial centerline of the third screw;

the proximal portion of the first tower extends at an acute, nonzero angle away from the axial centerline of the distal portion of the first tower; and the proximal portion of the second tower extends at an acute, nonzero angle away from the axial centerline of the distal portion of the second tower.

2. The system of Embodiment 1, wherein the proximal portion of the first tower is configured such that, in an operable state of the system, the proximal portion of the first tower also extends at an acute, nonzero angle away from the axial centerline of the proximal portion of the third tower so that the proximal portion of the first tower forms an acute angle relative to the proximal portion of the third tower.
3. The system of any one of the previous Embodiments, wherein the first tower is sized and configured such that, in an operable state, the proximal portion of the first tower extends away from a skin incision toward a surgeon.
4. The system of any one of the previous Embodiments, wherein the distal portion of the first tower extends away from the first screw to a height just below the skin incision, or to a height level with the skin of a patient, when the first screw is fully implanted in a first vertebra.
5. The system of any one of the previous Embodiments, wherein the proximal portion of the first tower is configured to be grasped by a surgeon to enable a surgeon to exert a rotational force on the first tower about at least the axial centerline of the distal portion of the first tower and/or a torque force on the first tower so as to cause the first tower to rotate about an axis that is perpendicular to an axial centerline of the distal portion of the first tower.
6. The system of any one of the previous Embodiments, wherein the proximal portion of the second tower is configured to be grasped by a surgeon to enable a surgeon to exert a rotational force on the second tower about at least the axial centerline of the distal portion of the second tower and/or a torque force on the second tower so as to create a compressive force on a second vertebra that the second screw is coupled with relative to a first vertebra that the first screw is coupled with.
7. The system of any one of the previous Embodiments, wherein the first tower is sized such that only the proximal portion of the first tower is outside of a skin incision when the first screw is implanted in a first vertebra.
8. The system of any one of the previous Embodiments, wherein the second tower is sized such that only the proximal portion of the second tower is outside of a skin incision when the second screw is implanted in a second vertebra.
9. The system of any one of the previous Embodiments, wherein the third tower is sized to extend completely through a skin incision when the third screw is implanted in a third vertebra.
10. The system of any one of the previous Embodiments, wherein the system is configured such that the first, second, and third screws are implanted through the same skin incision.
11. The system of any one of the previous Embodiments, wherein the proximal portion of the first tower has a length that is approximately the same as a length of the distal portion of the first tower.
12. The system of any one of the previous Embodiments, wherein the proximal portion of the first tower has a length that is at least 80% of a length of the distal portion of the first tower.
13. The system of any one of the previous Embodiments, wherein the proximal portion of the first tower is removably coupled with the distal portion of the first tower and the proximal portion of the second tower is removably coupled with the distal portion of the second tower.
14. The system of any one of the previous Embodiments, wherein the proximal portion of the first tower is non-removably coupled with the distal portion of the first tower and the proximal portion of the second tower is non-removably coupled with the distal portion of the second tower.
15. The system of any one of the previous Embodiments, wherein the proximal portion of the first tower is integrally formed with the body portion of the first tower.
16. The system of any one of the previous Embodiments, wherein at least the proximal portions of the first tower and the third towers have a tubular shape.
17. The system of any one of the previous Embodiments, wherein the first tower has a cutout formed through a wall portion of the first tower, the cutout being configured to receive at least the second tower and the second tower therein in an operable state.
18. The system of Embodiment 17, wherein the cutout extends at least through a proximal end of the distal portion of the first tower.
19. The system of Embodiment 17, wherein the cutout extends entirely through the first tower such that, in an operable state, the third tower can pass entirely through the cutout.
20. The system of Embodiment 17, wherein the cutout extends entirely through the first tower such that, in an operable state, the third tower can pass entirely through the cutout and such that the wall portion of the first tower surrounds an outside surface of a portion of the third tower.
21. The system of any one of Embodiments 17-20, wherein the cutout is shaped such that a distal edge of the cutout is configured to contact an outside surface of the second tower in an operable state so that the third tower can be rotated about the distal edge of the cutout relative to the first tower.
22. The system of any one of Embodiments 17-21, wherein the cutout has an ovular or elongated shape.
23. The system of any one of Embodiments 17-22, wherein the cutout is adjacent to a proximal end of the distal portion of the first tower and a distal end of the proximal portion of the first tower.
24. The system of any one of the previous Embodiments, wherein the second tower has a cutout formed through a wall portion of the second tower, the cutout being configured to allow the third tower to pass through the cutout of the second tower in an operable state.

25. The system of Embodiment 24, wherein the cutout extends entirely through the second tower such that, in an operable state, the third tower can pass entirely through the cutout.
26. The system of any one of Embodiments 24-25, wherein the cutout has an ovular or elongated shape.
27. The system of any one of Embodiments 24-22, wherein the cutout is adjacent to a proximal end of the distal portion of the second tower and a distal end of the proximal portion of the second tower.
28. The system of any one of the previous Embodiments, wherein the proximal portion of the first tower and/or the second tower is open along one side thereof and not fully enclosed.
29. The system of any one of the previous Embodiments, wherein, in an operable state, an axial centerline of both the distal portion of the second tower and the proximal portion of the second tower extend at a nonzero angle away from the axial centerline of the third tower in a same direction.
30. The system of any one of the previous Embodiments, wherein, in an operable state, an axial centerline of both the proximal portion of the first tower and the proximal portion of the second tower extend at a nonzero angle away from the axial centerline of the third tower in a same direction.
31. The system of any one of the previous Embodiments, wherein at least the distal portion of the first tower and the distal portion of the second tower have an adjustable length.
32. The system of any one of the previous Embodiments, wherein at least the distal portion of the first tower, the distal portion of the third tower, and the distal portion of the second tower are generally cylindrically shaped.
33. The system of any one of the previous Embodiments, wherein the proximal portion of the first tower and the proximal portion of the second tower have a cross-sectional profile having a curved shape.
34. The system of any one of the previous Embodiments, wherein the proximal portion of the first tower and the proximal portion of the second tower have a cross-sectional profile having a semi-circular tubular shape.
35. The system of any one of the previous Embodiments, wherein the proximal portion of the first tower and the proximal portion of the second tower have a planar shape.
36. The system of any one of the previous Embodiments, further comprising: a rigid connecting element; a first receiving element coupled with the first screw head; a second receiving element coupled with the second screw head; and a third receiving element coupled with the third screw head; wherein the first, second, and third receiving elements are configured to operably receive the connecting element that, in an operable state, extends between the first, second, and third receiving elements when the first, second, and third screws are implanted in a first, second, and third vertebra, respectively.
37. The system of any one of the previous Embodiments, wherein the first tower has at least one window extending through a side of the body portion thereof, the at least one window configured to receive a connecting element that is configured to extend between the first, second, and third screws in an operable state.
38. The system of any one of the previous Embodiments, wherein the second tower has at least one window extending through a side of the body portion thereof, the at least one window of the second tower configured to receive a connecting element that is configured to extend between the first, second, and third screws in an operable state.
39. The system of any one of the previous Embodiments, wherein the third tower has at least one window extending through a side of the body portion thereof, the at least one window of the third tower configured to receive a connecting element that is configured to extend between the first, second, and third screws in an operable state.
40. The system of any one of the previous Embodiments, wherein the first tower is shorter than the third tower at least in an operable state.
41. The system of any one of the previous Embodiments, wherein the first tower has a projection which provides a fulcrum for rotation of the first tower relative to the second tower.
42. The system of any one of the previous Embodiments, wherein the first, second, and third towers are releasably mechanically coupled with the first, second, and third screws, respectively.
43. The system of any one of the previous Embodiments, comprising two or more of the first towers and/or two or more of the second towers, wherein each of the two or more of the first towers define a different angle between the proximal portion and the distal portion of the first towers and each of the two or more of the second towers define a different angle between the proximal portion and the distal portion of the second towers.
44. A method of stabilizing spinal vertebrae, comprising:
    implanting a first screw that is coupled with a first tower through an incision into a first vertebra;
    advancing a second tower that is coupled with a second screw through a cutout formed in the first tower and implanting the second screw into a second vertebra;
    advancing a third tower that is coupled with a third screw through a cutout formed in the second tower and implanting the third screw into a third vertebra; and
    moving a proximal portion of the first tower toward a proximal portion of the second tower to cause a compressive force on at least the second vertebra relative to the first vertebra.
45. The method of Embodiment 42, further comprising coupling a rigid connector with the first screw, the second screw, and the third screw to generally fix a position of the first screw relative to the second screw and the third screw.

Systems, Devices and Methods of FIGS. 2A-2G

Additional embodiments of a system 200 that can be used for stabilizing or treating spinal vertebrae through a skin incision S are disclosed below. In any embodiments disclosed herein, any components, features, or other details of the system 200 can have any of the components, features, or other details of any other system embodiments disclosed herein or be used according to any of the steps of any other method embodiments disclosed herein, including without limitation the embodiments of the system 100 or methods of use thereof described herein, in any combination with any of the components, features, or details of the system 200 or methods of use disclosed herein. Similarly, any components, features, steps, or other details of any of the other system or method embodiments disclosed herein can have any of the components, features, steps, or other details of any embodiments of the system 200 or methods of use thereof disclosed herein in any combination with any of the components, features, or details of the system.

Some embodiments of the system 200 can be configured and/or optimized for use in robotic surgical procedures. For example and without limitation, in some embodiments, the proximal portions of the towers can be configured and optimized for grasping and locating by end effectors or robotic arms of a surgical robot. An advantage of some embodiments of the system 200 and other systems disclosed herein as compared to conventional spinal surgical systems is that two or more, or three or more towers of some embodiments of the system 200 can be advanced and manipulated through a single incision in the patient's back. Another advantage of some embodiments of the system 200 and other systems disclosed herein as compared to conventional spinal surgical systems is that the two or more or three or more towers of some embodiments of the system can be constrained by each other or otherwise configured to limit a range of movement of the towers relative to one another. This can assist in the ability to locate and/or control the towers of the system, particularly by a surgical robot. This can also make it easier to advance the connecting element (also referred to herein as a connecting rod) through the two or more towers or three or more towers because the two or more towers will be better aligned.

Some embodiments of the system 200 can be configured such that any of the towers attached to screws can be placed robotically and allow rod placement, rod reduction, compression, and/or final tightening with counter-torque all to be performed robotically through a mechanical coupling of parts of the tower system with robotic arms. The robot, navigation system, and/or software can be configured to identify or determine the positions of all towers screws, rods and caps at any desired time. In some embodiments, the proximal portions of the towers of any embodiments disclosed herein can be configured to be compatible with graspers, coupling mechanisms, and/or end effectors of surgical robots. For example and without limitation, as disclosed herein, the proximal portions of some embodiments of the towers disclosed herein can have a flat profile that can more easily and controllably be grasped by graspers, coupling mechanisms, and/or end effectors of surgical robots.

In any embodiments, the first, second, and third towers coupled with the screws can extend outside the body through the incision, and the proximal ends thereof can provide "handles" to allow the surgeon to know the position and orientation of the three screw heads constantly. This arrangement can also permit a robotic system to determine the orientation and position of all screw heads so that a robotic system would be able to lower the rod or connecting element directly into the screw heads, including with rotating the connecting element from vertical to horizontal into the seat of the heads of the screws. Any of the towers or other components can have additional features added thereto or otherwise be configured to integrate into a robotic system. Thereafter, the towers can be removed and withdrawn from the body, manually or robotically.

Some embodiments of the system 200 for stabilizing spinal vertebrae through a skin incision S can include a first screw 202, a second screw 204, a third screw 206, a first tower 212 having a distal portion **212*a* and a proximal portion 212*b*, a second tower 214 having a distal portion 214*a* and a proximal portion 214*b*, and a third tower 216 having a distal portion 216*a* and a proximal portion 216*b*. The first tower, second tower, and third tower can also be referred to herein as a first extension, second extension, and third extension, or guiding elements, or by other suitable terms understood in the industry. The first tower 212 can be configured to be removably coupled with the first screw 202 at a distal portion 212*a* of the first tower 212, the second tower 214 can be configured to be removably coupled with the second screw 204 at a distal portion 214*a* of the second tower 214, and third tower 216 can be configured to be removably coupled with the third screw 206 at a distal portion 216*a* of the third tower 216. In some embodiments, each of the first, second, and third screws 202, 204, 206 can be positioned in different vertebra. In some embodiments, each of the first, second, and third screws 202, 204, 206 can be positioned in adjacent vertebra. In some embodiments, the third screw 206 can be positioned in a vertebra between the first and second screws 202, 204, respectively. Additionally, note that, while the embodiments of the system 200 disclosed herein may have included screws as part of the system, any embodiments of the system 200 disclosed herein can exclude the screws such that the embodiments of the system 200** include the towers and/or other components other than the screws.

In any of the embodiments disclosed herein, the first, second, and third towers can be configured to be removably coupled with the screw heads and otherwise configured to be reuseable. This can save a significant cost as compared with disposable blade designs that, once the blade has been separated from the screw head, is typically discarded and not reused. From a surgical perspective, towers are more firm and rigid and can be used to provide rigidity to as to provide counter-torque during final tightening of the locking cap onto the rod in the screw head. Extended blades usually do not have the same strength as a counter-torque device. The towers of any of the embodiments disclosed herein, with the rigidity that they provide, can therefore help prevent the walls of the pedicle screw from splaying during final tightening of the locking cap.

The towers of some embodiments disclosed herein can provide a more complete enclosure than the blades or tabs can, due to the additional wall portions of the towers that extend between the sides of the towers. In some embodiments, as shown in the figures, the wall portions that extend between the two side wall portions to provide additional strength and stiffness can be integrally formed with the side wall portions, or can be separately formed and coupled (removably or nonremovably) with the side wall portions to provide additional rigidity to the towers.

In some embodiments, at least a portion of the distal portions of any embodiments of the first and/or second towers 212, 214 can be enclosed about at least 320° (or at least approximately 320°) of the circumference or cross-section of the first and/or second towers 212, 214, or from 180° (or approximately 180° or less) to 330° (or approximately 330°, or at least 330°), or from 210° (or approximately 210°) to 320° (or approximately 320°), or enclosed about any value or range of value within the foregoing ranges. In some embodiments, at least a portion of the distal portions of any embodiments of the first and/or second towers 212, 214 can be completely enclosed, with the optional exception of the channel extending lengthwise along at least the distal portion of the first and/or second towers 212, 214 sized and configured to permit a passage of the rod or connecting element toward the screws. Additionally, for example and without limitation, at least a portion of the distal portion of any embodiments of the third tower 216 can be enclosed about at least 270° (or at least approximately 270°) of the circumference or cross-section of the third tower 216, or from 240° (or approximately 240°) to 320° (or approximately 320°), or from 270° (or approximately 270°) to 300° (or approximately 300°), or enclosed about any value or range of value within the foregoing ranges. In some embodiments, at least a portion of the distal portion of any embodiments of the third tower 216 can be completely enclosed, with the exception of a channel on each side of the distal portion 216*b* of the third tower 216 extending lengthwise along at least the distal portion of the third tower 216 sized and configured to permit a passage of the rod or connecting element toward the screws.

In some embodiments, at least a portion of the distal portions of any embodiments of the first and/or second towers 212, 214 can be enclosed about at least 80% (or at least approximately 80%) of the circumference or cross-section of the first and/or second towers 212, 214, or from 70% (or approximately 70%) to 90% (or approximately 90%, or more than 90%—e.g., 95% or 100%), or from 75% (or approximately 75%) to 85% (or approximately 85%), or enclosed about any value or range of value within the foregoing ranges. Additionally, for example and without limitation, at least a portion of the distal portion of any embodiments of the third tower 216 can be enclosed about at least 50% (or at least approximately 50%) of the circumference or cross-section of the third tower 216, or from 60% (or approximately 60%) to 80% (or approximately 80%), or from 65% (or approximately 65%) to 75% (or approximately 75%), or enclosed about any value or range of value within the foregoing ranges.

Figure 2B:
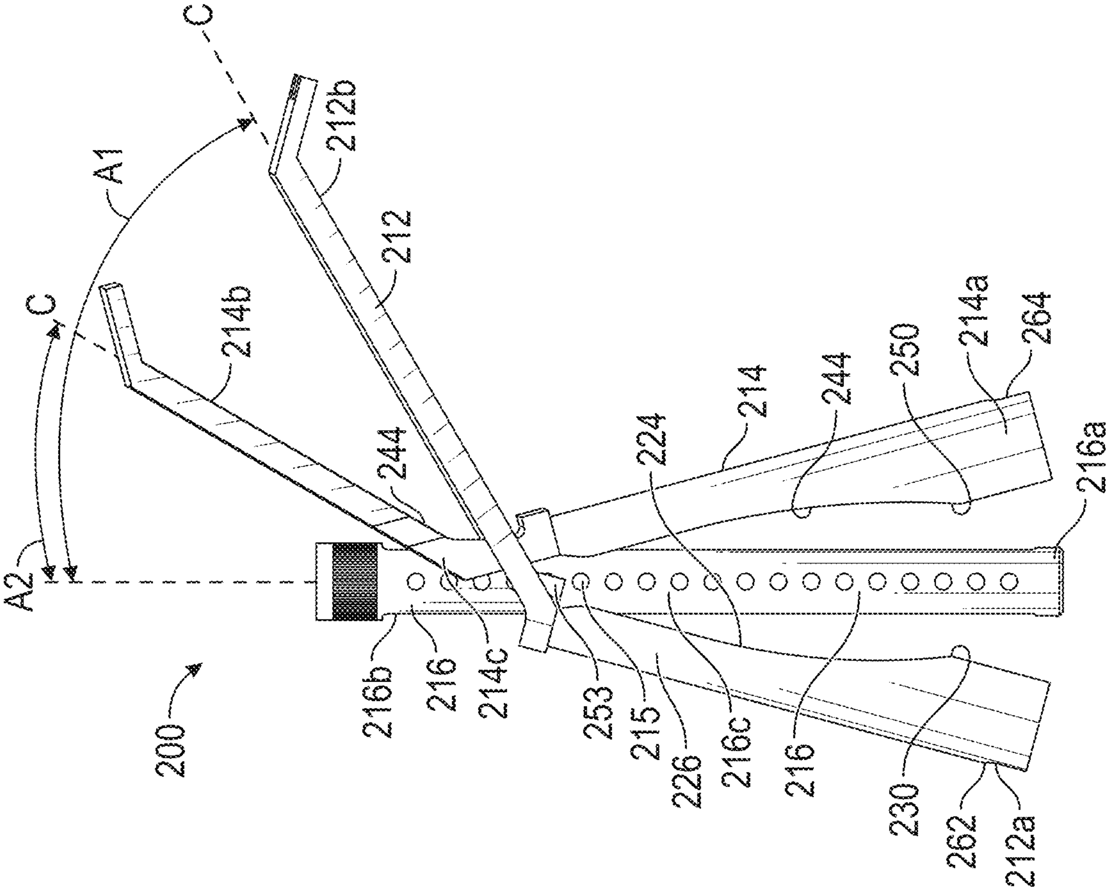
FIGS. 2A-2G illustrate another embodiment of a system for stabilizing spinal vertebrae comprising spinal screws.
Figure 2A:
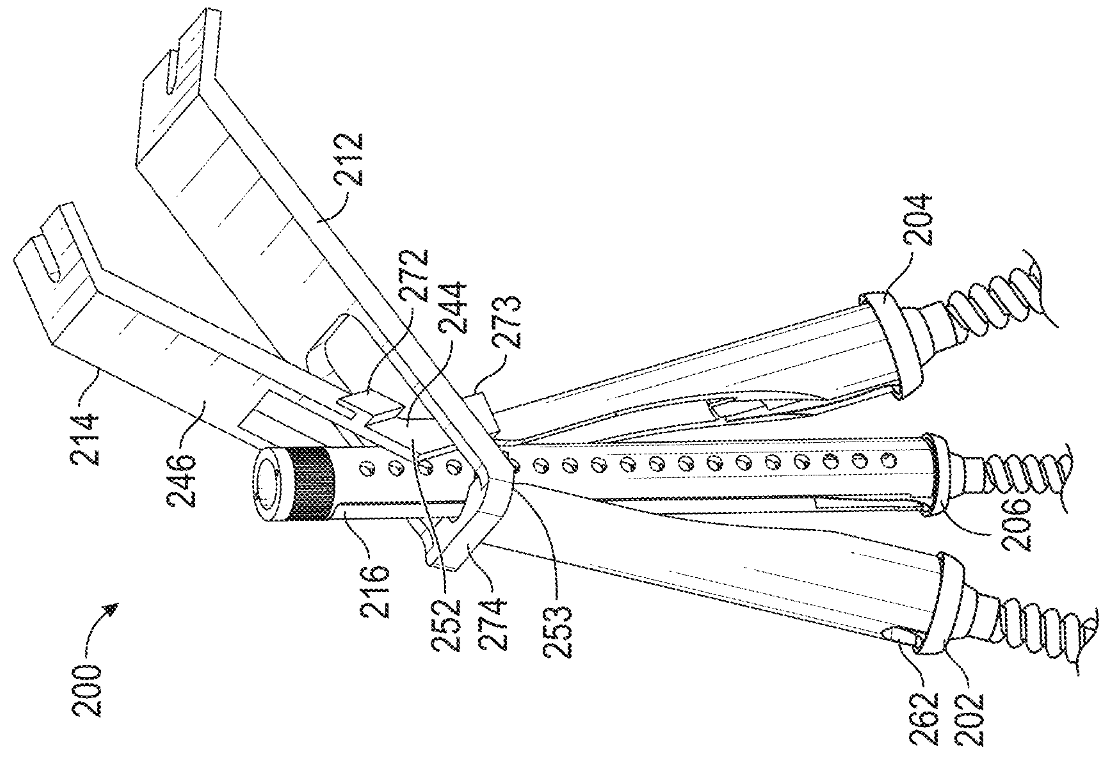
Figure 2D:
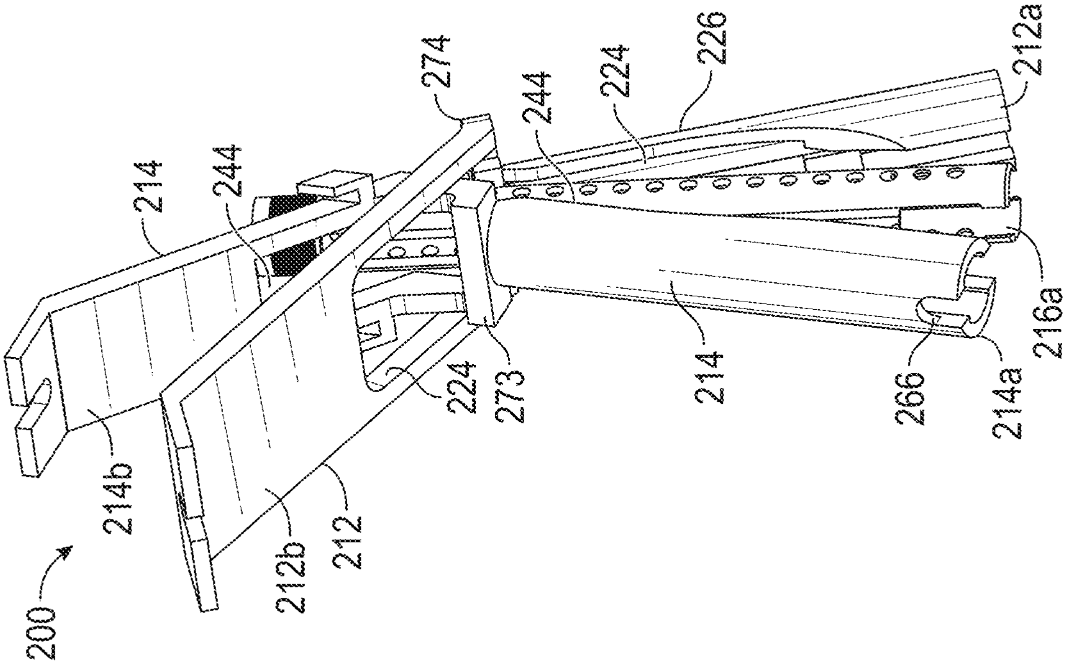
Figure 2C:
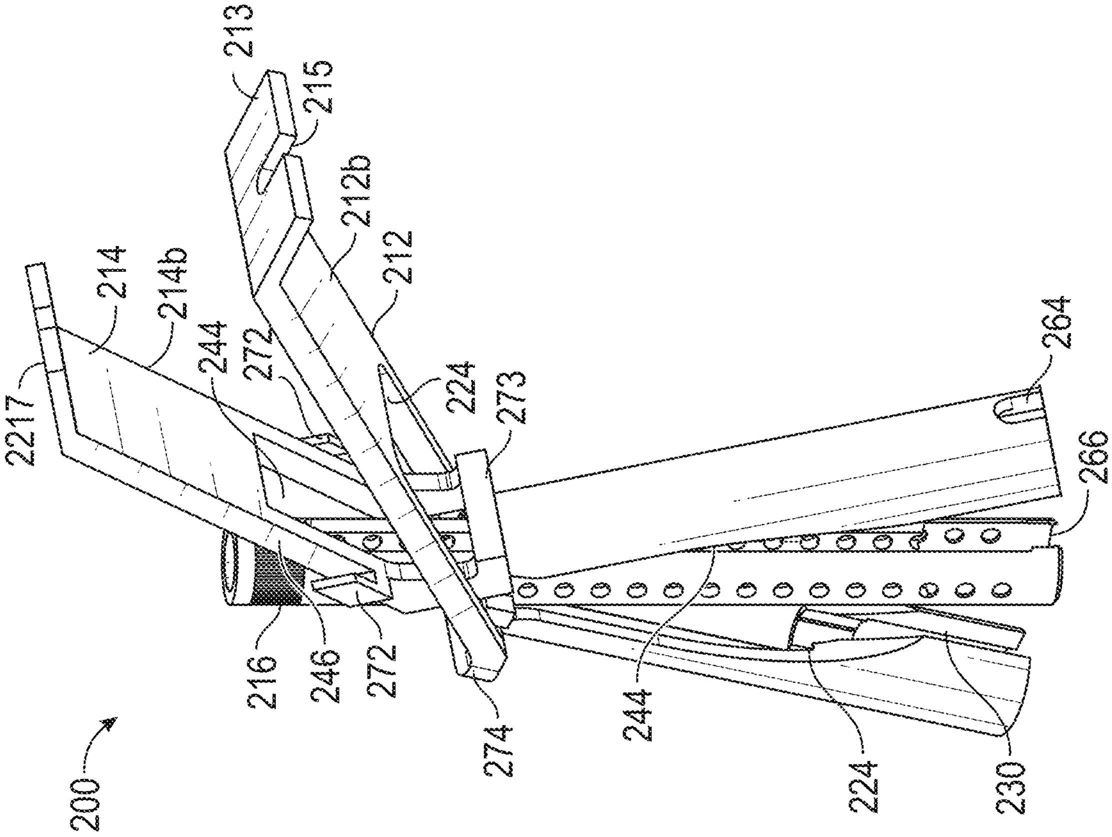
Figure 2E:
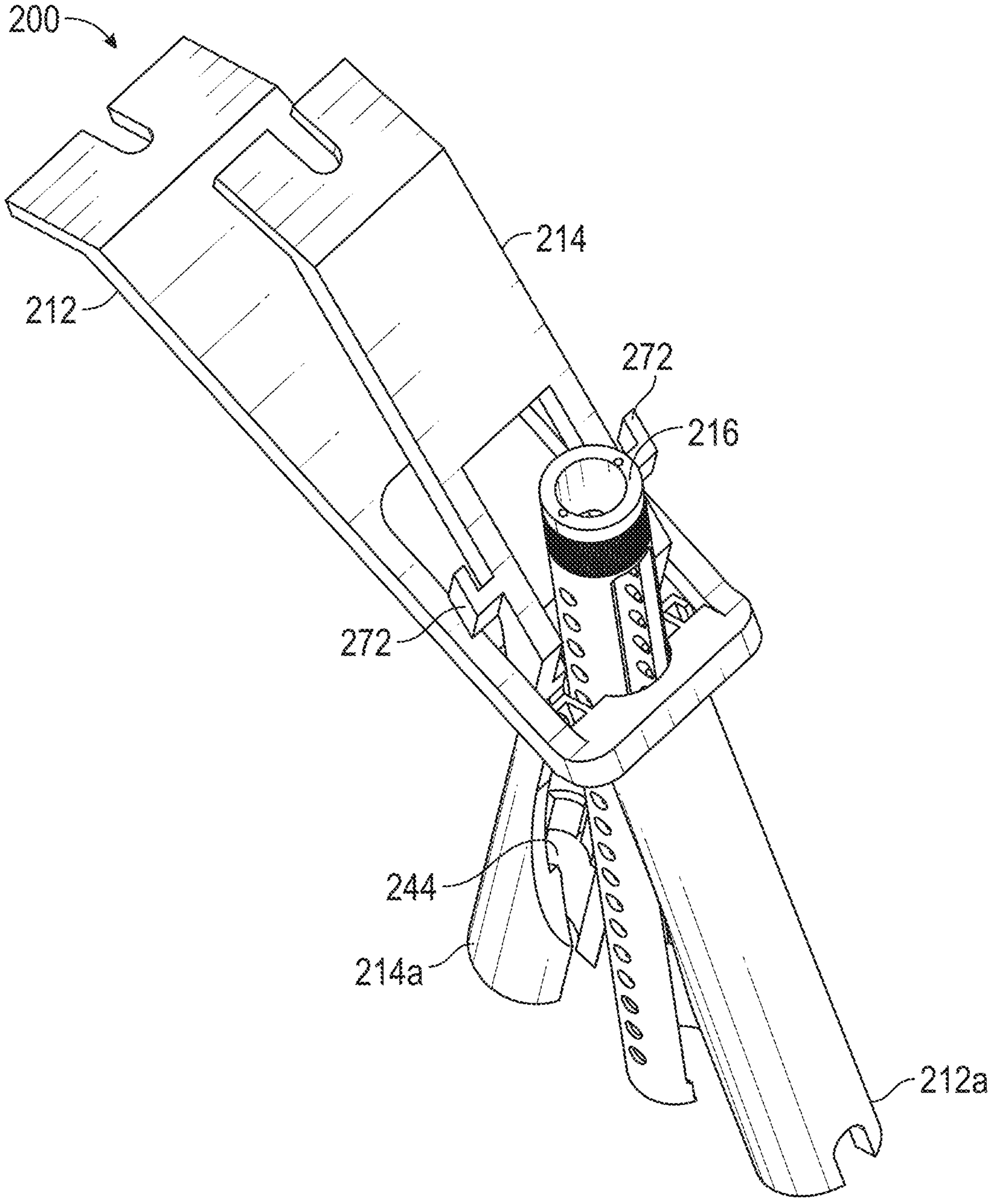

In some embodiments, with reference to FIG. 2B, the first tower 212 can have a bend between the distal portion 212*a* and the proximal portion 212*b* thereof. For example and without limitation, the distal portion 212*a* can be angled relative to the proximal portion 212*b* so that a longitudinal centerline C of the proximal portion 212*b* has an angle that is 45° or approximately 45° relative to a longitudinal centerline C of the distal portion 212*a* of the first tower 212, or so that the longitudinal centerline of the proximal portion 212*b* has an angle that is from 30° or approximately 30° to 60° or approximately 60°, or from 40° or approximately 40° to 50° or approximately 50° relative to the longitudinal centerline of the distal portion 212*a* of the first tower, or of any value or range of values within any of the foregoing ranges. In any embodiments, the third tower 216 can be generally straight along a length thereof, as shown, or can have a bend between the distal portion 216*a* and the proximal portion 216*b* thereof within any of the ranges mentioned above for the first tower 212.

In some embodiments, the second tower 214 can have a bend between the distal portion 214*a* and the proximal portion 214*b* thereof. The bend in the second tower 214 can be less than, can be greater than, or can be the same as the bend in the first tower 212. For example and without limitation, the distal portion 214*a* can be angled relative to the proximal portion 214*b* so that a longitudinal centerline C of the proximal portion 214*b* has an angle that is 45° or approximately 45° relative to a longitudinal centerline C of the distal portion 214*a* of the second tower 214, or that is 50° or approximately 50° relative to a longitudinal centerline C of the distal portion 214*a* of the second tower 214, or so that the longitudinal centerline C of the proximal portion 214*b* has an angle that is from 30° or approximately 30° to 60° or approximately 60°, or from 40° or approximately 40° to 50° or approximately 50° relative to the longitudinal centerline of the distal portion 216*a* of the first tower 212, or of any value or range of values within any of the foregoing ranges. In any embodiments, the third tower 216 can be generally straight along a length thereof, as shown, or can have a bend between the distal portion 216*a* and the proximal portion 216*b* thereof within any of the ranges mentioned above for the first tower 212.

Any embodiments of the system 200 disclosed herein can be configured such that the first screw 202, the second screw 204, and the third screw 206 can be implanted through the same skin incision S. Further, in any embodiments, a distal portion 214*a* of the third tower 216 can be positioned between the distal portions 212*a*, 214*a* of the first and second towers 212, 214 in an operable state of the system 200.

In some embodiments, the first tower 212 can have a two or more proximal portions 212*b* extending away from the distal portion 212*a* of the first tower 212 at a variety of angles. For example and without limitation, the two or more proximal portions 212*b* extending away from the distal portion 212*a* of the first tower 212 can provide two or more separate handles extending away from the distal portion 212*a* that a surgeon can grasp and manipulate. In some embodiments, the first tower 212 can removably couple with the first screw 2202 such that, when the first tower 212 is coupled with the first screw 202, an axial or longitudinal centerline C of the distal portion 212*a* of the first tower 212 is approximately collinear with an axial or longitudinal centerline C of the first screw 202. The second tower 214 can removably couple with the second screw 204 such that, when the second tower 214 is coupled with the second screw 204, an axial centerline C of the distal portion 214*a* of the second tower 214 is approximately collinear with an axial centerline C of the second screw 204. The third tower 216 can removably couple with the third screw 206 such that, when the third tower 216 is coupled with the third screw 206, an axial centerline C of the distal portion 216*a* of the third tower 216 is approximately collinear with an axial centerline C of the third screw 206. In any embodiments, the first tower 212 can be shorter than the second tower 214 or the third tower 216, longer than the second tower 214 or the third tower 216, or have approximately the same length as the second tower 214 or the third tower 216, and the second tower 214 can be shorter than the third tower 216, longer than the third tower 216, or have approximately the same length as the third tower 216.

In some embodiments, the angle between the proximal portion 212*b* and distal portion 212*a* of the first tower 212 can be adjustable, an angle between the proximal portion 214*b* and distal portion 214*a* of the second tower 214 can be adjustable, and/or the angle between the proximal portion 216*b* and distal portion 216*a* of the third tower 216 can be adjustable. A common mechanism for adjustability is a gear or ratchet mechanism. In this way, the proximal portion of any of the extensions can be angled away from the centerline of the distal portion of the respective screw. By adjusting the angle, there may be more room to place the rod and locking caps. Also, by adjusting the angle, it may be easier for a surgeon to grip both proximal portions of the towers in order to squeeze the two or three proximal portions of the extensions in order to compress the heads of screws when locking the caps onto the connecting element or rod connecting the screw heads. In another embodiment, proximal portions 212*b*, 214*b*, and/or 216*b* can be detachable from the distal portions 212*a*, 214*a*, and/or 216*a*. In this manner, proximal portions with different angles in relation to centerline of the respective distal portions can be switched as needed and reconnected to the distal portions of the extensions.

As mentioned, in some embodiments, the proximal portion 212*b* of the first tower 212 can extend at an angle away from the axial centerline C of the distal portion 212*a* of the first tower 212 such that an axial centerline of the proximal portion 212*b* of the first tower 212 is not approximately collinear with an axial centerline of the distal portion 212*a* of the first tower 212. Further, the first tower 212 can be configured such that, in an operable state, an axial centerline of the proximal portion 212*b* of the first tower 212 can extend at an angle away from the axial centerline C of the proximal portion of the third tower 216 so that the axial centerline of proximal portion 212*b* of the first tower 212 forms an acute angle A1 relative to the axial centerline of the proximal portion of the third tower 216, as shown in FIG. 2B. In some embodiments, the angle A1 can be 60° (or approximately 60°), or from 40° (or approximately 40°) or less to 80° (or approximately 80°) or more, or of any value or range of values within any of the foregoing ranges. The second tower 214 can be configured such that, in an operable state, an axial centerline of the proximal portion 214*b* of the second tower 214 can extend at an angle away from the axial centerline C of the proximal portion of the third tower 216 so that the axial centerline of proximal portion 214*b* of the second tower 214 forms an acute angle A2 relative to the axial centerline of the proximal portion of the third tower 216 in an operable state, as shown in FIG. 2B. In some embodiments, the angle A2 can be 30° (or approximately 30°), or from 15° (or approximately 15°) or less to 45° (or approximately 45°) or more.

In some embodiments, the first tower 212 can be angled such that, in an operable state, the proximal portion 212*b* of the first tower 212 can extend away from the proximal portion 216*b* of the third tower 216 in a first direction, and the second tower 214 can be angled such that, in an operable state, the proximal portion 214*b* of the second tower 214 can also extend away from the proximal portion of the third tower 216 in the same direction or approximately the same direction as the proximal portion 212*b* of the first tower—e.g., in the first direction. In some embodiments, the axial centerlines of the proximal portions 212*b*, 214*b* of the first and second towers 212, 214 can be within the same plane (e.g., a first plane) or approximately the same plane when the proximal portions 212*b*, 214*b* of the first and second towers 212, 214 extend away from the proximal portion of the third tower 216 in the same direction. The first plane that contains the axial centerlines of the proximal portions 212*b*, 214*b* of the first and second towers 212, 214 can also intersect with the axial centerline of the third tower 216, in some embodiments.

In some embodiments, the first tower 212 can be sized and configured such that, in an operable state, the proximal portion 212*b* of the first tower 212 can extend away from the skin incision S toward the surgeon. In some embodiments, the first, second, and third towers 212, 214, and 216 can be sized and configured such that the level of the patient's skin in an operable state of the system 200 will be at or adjacent to the bend 252 (e.g., just below the bend 252) formed in the second tower 214 or at or adjacent to the bend 253 (e.g., just below the bend 253) formed in the first tower 212. In some embodiments, the distal portion 212*a* of the first tower 212 and/or the distal portion 214*a* of the second tower 214 can extend away from the first screw 202 and the second screw 204 to a height just below the skin incision S (for example and without limitation, wherein a distance from the skin surface to the proximal most end of the distal portion of the first or third tower is less than or equal to 10% or approximately 10%, is less than or equal to 15% or approximately 15%, or is less than or equal to 20% or approximately 20% of a length of the distal portion of the first or third tower), or to a height level with the skin of a patient, or to a height just above the skin incision S (for example and without limitation, wherein a distance from the skin surface to the proximal most end of the distal portion of the first or third tower is less than or equal to 10% or approximately 10%, is less than or equal to 15% or approximately 15%, or is less than or equal to 20% or approximately 20%, of a length of the distal portion of the first or third tower), when the first and second screws 202, 204 are fully implanted in a first vertebra and a second vertebra, respectively.

In some embodiments, the first tower 212, the second tower 214, and/or the third tower 216 can intersect at a height just below the skin incision S. For example and without limitation, the first tower 212, the second tower 214, and/or the third tower 216 can intersect at an intersection point or points such that a distance from the skin surface to the point of intersection of the first tower 212 and the second tower 214, the first tower 212 and the third tower 216, the second tower 214 and the third tower 216, and/or the first tower 212, the second tower 214, and the third tower 216 is less than or equal to 10% of the length of the distal portion of the first tower or the second tower, wherein the point of intersection is at the skin surface, or optionally below the skin surface, or optionally above the skin surface for the intersection of the first tower 212 and the second tower 214, the first tower 212 and the third tower 216, the second tower 214 and the third tower 216, and/or the first tower 212, the second tower 214, and the third tower 216.

In some embodiments, the first tower 212 can be sized such that only the proximal portion 212*b* of the first tower 212 is outside of the skin incision S when the first screw 202 is implanted in a first vertebra, and the second tower 214 can be sized such that only the proximal portion 214*b* of the second tower 214 is outside of the skin incision S when the second screw 204 is implanted in a second vertebra. In any embodiments, the third tower 216 can be sized to extend completely through the skin incision S when the third screw 206 is implanted in a third vertebra.

The proximal portion 212*b* of the first tower 212 and the proximal portion 214*b* of the second tower 214 can be configured to be grasped by a surgeon to enable a surgeon to exert a rotational force on the first tower 212 about at least the axial centerline C of the distal portion 212*a* of the first tower 212 about at least the axial centerline C of the distal portion 212*a* of the first tower 212 and/or a torque force on the first tower 212 so as to cause the first tower 212 to rotate about an axis that is perpendicular to an axial centerline C of the distal portion 212*a* of the first tower 212. The proximal portion 214*b* of the second tower 214 and the proximal portion 214*b* of the second tower 214 can be configured to be grasped by a surgeon to enable a surgeon to exert a rotational force on the second tower 214 about at least the axial centerline C of the distal portion 214*a* of the second tower 214 about at least the axial centerline C of the distal portion 214*a* of the second tower 214 and/or a torque force on the second tower 214 so as to cause the second tower 214 to rotate about an axis that is perpendicular to an axial centerline C of the distal portion 214*a* of the second tower 214.

The proximal portion 212*b* of the first tower 212 can have a length that is approximately the same as a length of the distal portion 212*a* of the first tower 212, or can have a length that is at least 80% or less or 120% or less of a length of the distal portion 212*a* of the first tower 212. In some embodiments, the proximal portion 212*b* of the first tower 212 can be removably coupled with the distal portion 212*a* of the first tower 212. In other embodiments, the proximal portion 212*b* of the first tower 212 can be non-removably coupled with the distal portion 212*a* of the first tower 212. For example and without limitation, the proximal portion 212*b* of the first tower 212 can be integrally formed with the body portion of the first tower 212. In any embodiments, the second and third towers 214, 216 can be similarly configured.

In some embodiments, at least the proximal portion 212*b* of the first tower 212 and/or the second tower 214 can have a flat or rectangular shape—for example and without limitation, a solid rectangular shape wherein a width of the proximal portion can be significantly greater than a thickness of the proximal portion. In some embodiments, the width of the proximal portion of the first and/or third towers can be 6 times or approximately 6 times greater or more than a thickness of the proximal portion, or from 4 times or approximately 4 times greater to 8 times or approximately 8 times greater than a thickness of the proximal portion of the first and/or third towers, or of any values or from and to any values within the foregoing range. The first tower 212 can have a cutout 224 formed through a wall portion 226 of the distal portion 212*a* first tower 212 and through the proximal portion 212*b* of the first tower 212. The cutout 224 being configured to receive a portion of or permit the passage therethrough of an outside surface 216*c* of the third tower 216 therein in an operable state, as shown in the figures. In some embodiments, the cutout 224 of the first tower 212 can be large enough to also receive a portion of an outside surface 214*c* of the second tower 214 therein in an operable state, as shown in the figures. In some embodiments, the cutout 224 can extend at least through a proximal end 212*c* of the distal portion 212*a* of the first tower 212. The cutout 224 can extend entirely through the first tower 212 and be sized and configured such that, in an operable state, the third tower 216 and the screw coupled with the third tower 216 can pass entirely through the cutout 224 in the first tower 212 and the screw coupled with the second tower 214 and at least the distal portion 214*b* of the second tower 214 can pass entirely through the cutout 224.

In some embodiments, the proximal portion 212*b* of the first tower 212 can have an angled portion 213 at a proximal most end of the proximal portion 212*b*. The angled portion can be angled relative to the adjacent portion of the proximal portion 212*b*. The angled portion can be angled at an angle of 45° or approximately 45° relative to the adjacent portion of the proximal portion 212*b*, or from 35° or approximately 35° to 55° or approximately 55° relative to the adjacent portion of the proximal portion 212*b*. The angled portion 213 can have a slot or opening 215 formed therein. In some embodiments, the proximal portion 212*b* of the first tower 212 can have a cross-sectional shape, profile, and/or size that is the same as or similar to handle portion of METRX RETRACTOR TUBES. The second tower 214 can be similarly configured.

In some embodiments, the cutout 224 can extend entirely through the first tower 212 such that, in an operable state, the third tower 216 can pass entirely through the cutout 224 and such that the wall portion 226 of the first tower 212 completely and continuously surrounds the outside surface 216*c* of a portion of the third tower 216 and the outside surface 214*c* of a portion of the second tower 214. Some embodiments of the cutout 224 can have a distal edge 230. In some embodiments, the distal edge 230 can be lower to allow for a wider range of rotation or movement of the first tower 212 relative to the third tower 216. In some embodiments, the cutout 224 can extend distally to be near to or adjacent to the distal end of the first tower. Some embodiments of the cutout 224 can have an elongated or ovular shape.

In some embodiments, at least the distal portion 214*a* of the second tower 214 can have a tubular or half-tubular shape. The second tower 214 can have a cutout 244 formed through a wall portion 246 of the distal portion 214*a* of the second tower 214 and through the proximal portion 214*b* of the second tower 214, the cutout 244 being configured to receive a portion of an outside surface 216*c* of the third tower 216 therein and/or to permit a user to advance the third tower 216 therethrough in an operable state, as shown in the figures. In some embodiments, the cutout 244 can extend at least through a proximal end 214*b* of the distal portion 214*a* of the second tower 214. The cutout 244 can extend entirely through the second tower 214 such that, in an operable state, the third tower 216 and the screw coupled with the third tower 216 can pass entirely through the cutout 244 in the second tower 214.

In some embodiments, the cutout 244 can be configured such that, in an operable state, the third tower 216 can pass entirely through the cutout 244 and such that the wall portion 246 of the second tower 214 completely and continuously surrounds the outside surface 216*c* of a portion of the third tower 216. In some embodiments, as shown, the cutout 244 can be configured such that, in an operable state, the outside surface 216*c* of the third tower 216 is only partially surrounded by the wall portion 246 of the second tower 214. For example and without limitation, the second tower 214 can form an approximately U shape at the proximal end 214*b* of the distal portion 214*a* of the second tower 214. Further, some embodiments of the cutout 244 can have a distal edge 250. In some embodiments, the distal edge 250 can be lower to allow for a wider range of rotation or movement of the second tower 214 relative to the third tower 216. In some embodiments, the cutout 244 can extend distally to be near to or adjacent to the distal end of the tower (e.g., the second tower 214). Some embodiments of the cutout 244 can have an elongated or ovular shape.

In some embodiments, at least the distal portion 212*a* of the first tower 212, the distal portion 214*a* of the second tower 214, and/or the distal portion 216*a* of the third tower 216 can have an adjustable length. Further, some embodiments of the distal portion of the first tower 212, the second tower 214, and/or the third tower 216 can be generally cylindrically shaped. Other embodiments can have any other desired cross-sectional shape, including a generally square shape, a triangular cross-sectional shape, on ovular cross-sectional shape, a polygonal cross-sectional shape, or any combination of the foregoing.

The proximal portion 212*b* of the first tower 212 and/or the proximal portion 214*b* of the second tower 214 can have a cross-sectional profile that can have a curved shape. In some embodiments, the proximal portion 212*b* of the first tower 212 and/or the proximal portion 214*b* of the third tower 214 can have a planar shape.

Any of the embodiments of the system 200 disclosed herein can include a rigid connecting element (not shown), similar to any of the other embodiments of the connecting elements disclosed herein, that can be implanted using any desired shape and configuration of a connecting element implantation device, or implanted using any other devices or methods disclosed herein or other desired devices or methods. For example and without limitation, any embodiments of the system disclosed herein (including embodiments of the system 200) can be configured to implant the connecting element using the same or similar components of the MEDTRONIC SEXTANT II PERCUTANEOUS ROD SYSTEM, adapted for use with the embodiments disclosed herein. Any embodiments of the system disclosed herein (including embodiments of the system 200) can be configured to implant the connecting element using a rotating implantation component that is configured to rotate about an axis outside of the body and to deliver the connection element in the desired location with respect to the towers and screws.

In some embodiments, a first receiving element coupled with the head of the first screw 202, a second receiving element coupled with the head of the second screw 204, and a third receiving element coupled with the head of the third screw 206 can secure the connecting element to the screws 202, 204, 206. The first, second, and third receiving elements can be configured to operably receive the connecting element that, in an operable state, can extend between the first, second, and third receiving elements when the first screw 202, the second screw 204, and the third screw 206 are implanted in a first vertebra, a second vertebra, and a third vertebra, respectively.

In some embodiments, the first tower 212 can have at least one window or slot 262 extending through a side of the body portion thereof, the at least one window or slot 262 configured to receive a connecting element 251 or configured to permit a passage of a connecting element 251 therethrough. Further, the second tower 214 can have at least one window or slot 264 extending through a side of the body portion of the second tower 214, the at least one window or slot 264 of the second tower 214 configured to receive the connecting element 251 that is configured to extend between the first screw 202 and the second screw 204 in an operable state. The third tower 216 can have at least one window or slot 266 extending through a side of the body portion of the third tower 216, the at least one window or slot 266 of the third tower 216 configured to receive the connecting element 251 that is configured to extend between the first screw 202 and the second screw 204 in an operable state. Lengthwise slots or channels can be formed in at least the distal portions of each of the first, second, and third towers to permit the connecting element to pass distally toward the screws.

In some embodiments of the system 200, though not shown, the first tower 212 can optionally have an insert or projection 270 formed thereon or coupled therewith or positioned adjacent thereto. The projection 270 can have a distal portion 270*a* that, in some embodiments, in an operable state, contacts the outside surface 214*c* of the third tower 216 to provide a point or a region of contact between the proximal portion 212*a* of the first tower 212 and the proximal portion 216*b* of the third tower 216. In some embodiments of this configuration, as the proximal portion 212*b* of the first tower 212 is squeezed relative to or otherwise rotated or moved toward the proximal portion 216*b* of the third tower 216, the distal portion 270*a* of the projection 270 can contact the outside surface 216*c* of the third tower 216 and the distal portion 212*a* of the first tower 212 can be moved toward the distal portion 216*a* of the third tower 216 to cause a compressive force to be exerted on a first vertebra that the first tower 212 is coupled with relative to a third, adjacent vertebra that the third tower 216 is coupled with. In other embodiments, the projection 270 can be configured to rotate or otherwise move so that the point or region of contact and rotation between the first and third towers 212, 216 is only at the distal edge 230 of the cutout 224. In some embodiments of this configuration, as the proximal portion 212*b* of the first tower 212 is moved away from the proximal portion 216*b* of the third tower 216, the distal portion 212*a* of the first tower 212 can be moved away from the distal portion 216*a* of the third tower 216 to cause a traction force to be exerted on a first vertebra that the first tower 212 is coupled with relative to a third, adjacent vertebra that the third tower 216 is coupled with.

In some embodiments, the projection 270 can be removably or nonremovably positioned between the proximal portion 212*b* of the first tower 212 and the proximal portion 214*b* of the second tower 214, when needed or desired, to provide a fulcrum between the first and second towers 212, 214 during compression. In other embodiments, the projection 270 can be nonremovably coupled with the proximal portion 212*b* of the first tower 212 or integrally formed with the proximal portion 212*b* of the first tower 212, or nonremovably coupled with an outside surface of the proximal portion 214*b* of the second tower 214 or integrally formed with the proximal portion 214*b* of the second tower 214 so as to be between the proximal portion 214*b* of the second tower 214 and the proximal portion 212*b* of the first tower 212.

In some embodiments, the projection 270 can be configured to contact the outside surface 214*c* of the second tower 214, for example, in a proximal portion 214*b* of the second tower 214, to provide a point or a region of contact and rotation, or a fulcrum, between the proximal portion 212*a* of the first tower 212 and the proximal portion 214*b* of the second tower 214. In some embodiments of this configuration, as the proximal portion 212*b* of the first tower 212 is squeezed relative to or otherwise rotated or moved toward the proximal portion 214*b* of the second tower 214, a proximal portion 270*b* of the projection 270 can contact the outside surface 216*c* of the proximal portion 214*b* of the second tower 214 to provide the point or a region of contact and rotation, or a fulcrum, between the proximal portion 212*a* of the first tower 212 and the proximal portion 214*b* of the second tower 214 to cause a compressive force to be exerted on a first vertebra that the first tower 212 is coupled with relative to a second vertebra that the second tower 214 is coupled with. In other embodiments, one or more rings, shafts, pins, pegs, and/or other mechanical connectors can be used to create the point or region of rotation, or fulcrum, between the first, second, and/or third towers 212, 214, 216. For example and without limitation, with reference to FIG. 2B, a peg or a pair of pegs or pins advanced into the opening 215 passing through the third tower 216 that extends radially outwardly away from the outside surface 216*c* of the third tower 216 could be used to provide a pivot point or fulcrum between the first tower 212 and the second tower 214. The peg(s) or pin(s) that can extend through the openings 215 can be used in lieu of the projection 270 to provide the fulcrum between the first and second towers 212, 214. In some embodiments of this configuration, as the proximal portion 212*b* of the first tower 212 is moved away from the proximal portion 214*b* of the second tower 214, the system 200 can be configured to cause the distal portion 212*a* of the first tower 212 to move away from the distal portion 214*a* of the second tower 214 to thereby cause a traction force to be exerted on a first vertebra that the first tower 212 is coupled with relative to a second vertebra that the second tower 214 is coupled with.

In some embodiments, the second tower 214 can have one or more hooks 272 (two being included in the illustrated embodiment) positioned at the sides of the proximal portion of the second tower 214. The hooks 272 can extend laterally away from the sides of the proximal portion of the second tower 214. In some embodiments, the hooks 272 can be used to constrain one or more wires during a procedure. The hooks 272 can also be used to create a pivot point or fulcrum against which a top surface of the proximal portion 212*b* of the first tower 212 can contact and about which the first tower 212 can pivot or rotate.

Additionally, the first tower 212 can have a reinforcing element 274 at or adjacent to a proximal end of the distal portion 212*a* of the first tower 212. The reinforcing element 274 can extend laterally across the first tower 212 and can increase the stiffness of the first tower 212 in bending and/or in torsion. Similarly, in some embodiments, the second tower 214 can have a reinforcing element 273 at or adjacent to a proximal end of the distal portion 214*a* of the second tower 214. The reinforcing element 273 of the second tower 214 can extend laterally across the second tower 214 and can increase the stiffness of the second tower 214 in bending and/or in torsion.

Figure 2G:
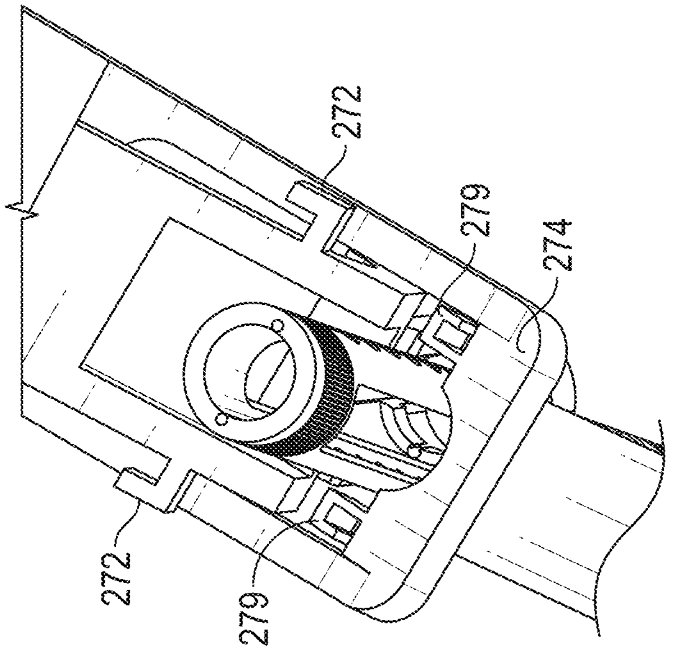

In some embodiments, with reference to FIG. 2G, the second tower 214 can have one or more hooks 279 (two being included in the illustrated embodiment) coupled with the reinforcing element 274. In some embodiments, the hooks 279 coupled with the reinforcing element 274 can be used to constrain one or more wires during a procedure.

Figure 2F:
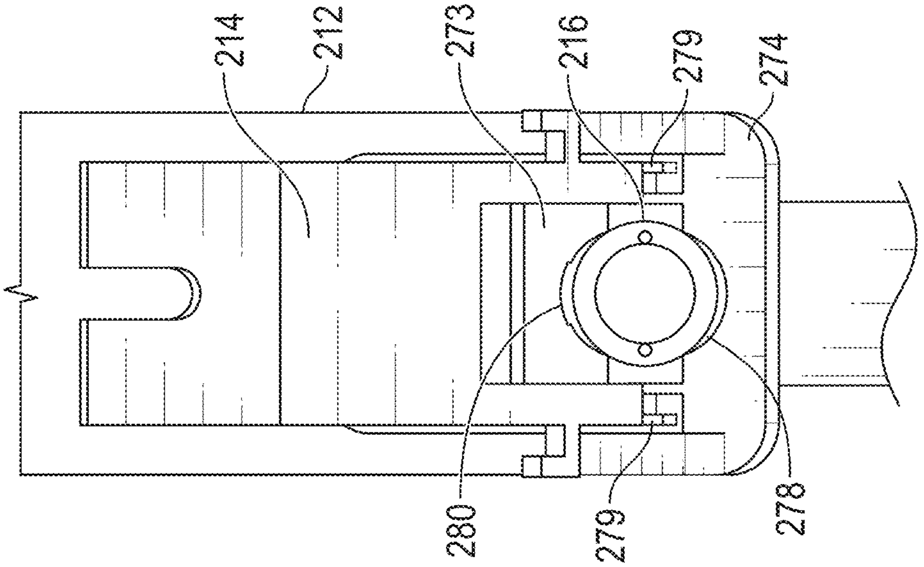

With reference to FIGS. 2F and 2G, some embodiments of the reinforcing element 274 of the first tower 212 can have a cutout 278 (that can optionally be circular) formed therein that can receive a portion of an outside surface of the third tower 216 therein. The cutout 278 can be used to partially constrain the first tower 212 with respect to the third tower 216, particularly when the first tower 212 is moved to force the cutout 278 into contact with the outside surface of the third tower 216. In some embodiments, the radius of the cutout 278 can be less than a radius of the outside surface of the third tower 216. In other embodiments, the cutout 278 can have a V shape.

Additionally, some embodiments of the reinforcing element 273 of the second tower 216 can have a cutout 280 (that can optionally be circular) formed therein that can receive a portion of an outside surface of the third tower 216 therein. The cutout 280 can be used to partially constrain the second tower 214 with respect to the third tower 216, particularly when the second tower 214 is moved to force the cutout 280 into contact with the outside surface of the third tower 216. In some embodiments, the radius of the cutout 280 can be less than a radius of the outside surface of the third tower 216. In other embodiments, the cutout 280 can have a V shape.

In some embodiments, the first, second, and third towers 212, 214, 216 can be configured to be selectively removable from the first, second, and third screws 202, 204, 206. For example and without limitation, some embodiments of the first, second, and third towers 212, 214, 216 can have one or more creases, fracture lines, or lines of weakness (for example, two creases, fracture lines, or lines of weakness) along a length of a wall portion of any or all of the first, second, and third towers 212, 214, 216. In some embodiments, a tool or other device can be used to fracture the first, second, and third towers 212, 214, 216 along the one or more creases, fracture lines, or lines of weakness to remove the first, second, and third towers 212, 214, 216 from the first, second, and third screws 202, 204, 206. In some embodiments, the one or more creases, fracture lines, or lines of weakness can be circumferentially arranged and positioned at or adjacent to a top surface of the screws that the towers are attached to so that the towers can break along the one or more creases, fracture lines, or lines of weakness at or adjacent to the screws and be removed.

In some embodiments, the first, second, and third towers 212, 214, 216 can have distal end portions having circumferential, helical, and/or discrete/intermittent projections, tabs, lip(s), flanges, grooves, channels, detents, or other mechanically locking features that engage with complementary locking features of the screw heads to cause the first, second, and third towers 212, 214, 216 to be coupled with the screw heads when the first, second, and third towers 212, 214, 216 are intact, but which can each be decoupled from the complementary locking features of the screw heads when the first, second, and/or third towers 212, 214, 216 are fractured or split apart. As another example, a third wall or connecting wall connecting two sides of any of the first, second, and/or third towers 212, 214, 216 can have an angled or "V" shaped profile wherein a fracture line or line of weakness extends along the apex or angle of the angled or "V" shaped profile such that, when the two sides of the first, second, and third towers 212, 214, 216 are squeezed toward one another, such force from the squeezing can cause a fracture along the fracture line or line of weakness in the connecting portion, thereby allowing the first and second sides of the tower to separate so that tower can be removed from the screw head. In some embodiments, a slider ring can be slid down the tower to cause the two sides of the tower to be squeezed toward one another. In some embodiments, the first, second, and third towers 212, 214, 216 can have tabs that extend from the first, second, and third screw heads that can be broken off from the screw heads after implantation. In some embodiments, the first, second, and/or third towers can be removably coupled with the first, second, and/or third screws by rotating the first, second, and/or third towers into engagement with the first, second, and/or third screws, and removed in the opposite manner.

In other embodiments, the extensions can be removably coupled with the screws so that the entire extension can be removed from the screw and the patient intact and be reused in subsequent procedures. For example and without limitation, ball and detent removable coupling mechanisms can be used to removably couple the first, second, and third towers 212, 214, 216 with the first, second, and third screw heads. Other conventional or desired coupling mechanisms can be used to removably couple the first, second, and third towers 212, 214, 216 with the first, second, and third screw heads. In other embodiments, a plurality of wires can be used to removably couple the first, second, and third towers 212, 214, 216 with the first, second, and third screw heads.

Some embodiments of methods for treating a spinal defect include implanting a first screw 202 that is coupled with a first tower 212 through the incision into a first vertebra, advancing a second tower 214 that is coupled with a second screw 204 through the cutout 224 formed in the first tower 212 and implanting the second screw 204 into a second vertebra, and advancing a third tower 216 that is coupled with a third screw 206 through the cutout 244 formed in the second tower 214 and implanting the third screw 206 into a third vertebra. In some embodiments, the third vertebra can be between the first and second vertebrae.

The surgeon or medical practitioner can move a proximal portion 212*b* of the first tower 212 toward a proximal portion 214*b* of the second tower 214 to cause the distal portion 212*a* of the first tower 212 to move toward the distal portion 214*a* of the second tower 214, thereby causing a compressive force to be applied between the first, second, and third vertebrae. In some embodiments, the method can further include coupling a rigid connector or rod with the first screw 202, the second screw 204, and the third screw 206 to generally fix a position of the first screw 202 relative to the second screw 204 and the third screw 206. Thereafter, the first, second, and third towers 212, 214, 216 can be removed from the first, second, and third screws 202, 204, 206.

Any embodiments of the system 200 disclosed herein can be configured for use in performing L4, L5 and S1 surgical procedures, as well as cortical screw trajectory procedures. Additionally, any embodiments of the system 200 disclosed herein can be configured to enable compression, traction, and/or counter-torque all with one device, and the extensions can be configured to allow a tower, rod insertion, and rod reducer (using extended tabs with threads) with one device.

In any system embodiments disclosed herein, including without limitation the embodiments of the system 100, 200, any of the towers (also referred to herein as extensions) can have an open channel or opening along the length of at least a portion of the tower. The open channel or opening can, in some embodiments, reduce the torsional or bending stiffness of the tower during an implantation procedure—for example and without limitation, when counter-torque forces applied to the tower. Additional components and devices, such as the embodiments of the covers that are disclosed below, can be used to selectively reinforce or close at least a portion of the channel or opening to selectively increase a rigidity or stiffness of the tower. For example and without limitation, in some embodiments, a cover can be slid longitudinally over the channel or opening to selectively close the channel or opening or selectively increase a stiffness of the tower. The cover can have grooves or channels that can be used to guide the cover to be in contact with the tower at the desired location and also connect the cover to the tower to increase the stiffness of the tower at the location of the channel or opening. In some embodiments, the cover can be coupled with the tower after the rod or connecting element has been advanced or at least been partially advanced through the tower and/or screw heads. As mentioned, the closing of the open channel can, in some embodiments, aid in stabilizing the tower to aid final tightening of the locking cap and using the towers as a counter torque mechanism.

Systems, Devices and Methods of FIGS. 3A-30

Additional embodiments of a system 300 that can be used for stabilizing or treating spinal vertebrae through a skin incision S are disclosed below. In any embodiments disclosed herein, any components, features, or other details of the system 300 can have any of the components, features, or other details of any other system embodiments disclosed herein or be used according to any of the steps of any other method embodiments disclosed herein, including without limitation the embodiments of the system 100 or 200 or methods of use thereof described herein, in any combination with any of the components, features, or details of the systems 100 or 200 or methods of use disclosed herein. Similarly, any components, features, steps, or other details of any of the other system or method embodiments disclosed herein can have any of the components, features, steps, or other details of any embodiments of the system 100 or 200 or methods of use thereof disclosed herein in any combination with any of the components, features, or details of the system.

Some embodiments of the system 300 for stabilizing spinal vertebrae through a skin incision S can include two or more screws and a corresponding number of towers. In some embodiments, the system 300 may include the same or substantially similar tower configuration as in systems 100, 200. The system 300 can include a first screw 302, a second screw 304, a first tower 312 having a distal portion 312*a*, a proximal portion 312*b*, and an opening or a cutout 324 formed through a wall portion 326 of the proximal portion of the first tower 312 or at least the proximal portion of the first tower 312. The system 300 can also have a second tower 314 having a distal portion 314*a*, a proximal portion 314*b*, and an opening or a cutout 344 formed through a wall portion 346 of the proximal portion 314*b* or through a wall portion 346 of at least the proximal portion 314*b* of the second tower. In some embodiments, the first tower 312 can have an opening or window 362 (also referred to herein as a slot) in a distal portion of the first tower and the second tower 314 can have an opening or window 364 (also referred to herein as a slot) in the distal portion 314*a* of the second tower 314.

In some embodiments, the first screw 302 may be the same or similar to the first screws 102, 202. In some embodiments, the second screw 304 may be the same or similar to the second screws 104, 204. The first tower 312 may be the same or similar to the first towers 112, 212 in some embodiments such that the distal portion 312*a*, window or slot 362, the proximal portion 312*b*, the cutout 344, and the wall portion 346 may correspond to the distal portions 112*a*, 212*a*, the window or slot 162, 262, the proximal portions 112*b*, 212*b*, the cutouts 124, 224, and the wall portions 126, 226, respectively. The second tower 314 may be the same or similar to the second towers 114, 214 in some embodiments such that the distal portion 314*a*, the window or slot 164, 264, the proximal portion 314*b*, the cutout 344, and the wall portion 346 may correspond to the distal portions 114*a*, 214*a*, the proximal portions 114*b*, 214*b*, the cutouts 144, 244, and the wall portions 146, 246, respectively.

Additionally, the first tower 312 can include an opening 323 that permits access to the inside of the distal portion of the first tower 312. A longitudinal axis A2-A2 can extend through a longitudinal centerline of the distal portion of the first tower 312. Similarly, a longitudinal axis A4-A4 can extend through a longitudinal centerline of the distal portion of the second tower 314. The first screw 302 may be coupled with the first tower 312 and configured to engage into a first vertebra, the second tower 314 may be coupled with the second screw 304 and advanced through the cutout 324 formed in the first tower 312 and the second screw 304 may be implanted into a second vertebra. In any embodiments, the system 300 can include a third tower that is generally straight along an entire length thereof and/or can have any of the shapes, features, or otherwise of any of the towers (also referred to as extensions) described above.

The first and second screws 302, 304 may be the same or similar to the first and third screws 102, 202, 104, 204 described above. The first and second screws 302, 304 may have different lengths, the same lengths, different shapes, or the same shape. The first and second screws 302, 304 may have a first screw head and a second screw head, respectively. In some embodiments, the screws may have different lengths and may have different shapes thereby advantageously accommodating non-linear connection elements and/or rods.

In some embodiments, as in any embodiments of the towers disclosed herein, the distal portions 312*a*, 314*a* of any of the first tower 312 and/or second tower 314 can be completely enclosed (e.g., can have a tubular wall that is without void or gap around the entire circumference of the distal portion of the tower) or substantially completely enclosed (e.g., having a circumference that is 80% or more enclosed along at least a portion of the length of the distal portion of the tower, or that is 85% or more enclosed along at least a portion of the length of the distal portion of the tower, or that is 90% or more enclosed along at least a portion of the length of the distal portion of the tower). Complete enclosure may advantageously provide additional structural support and torsional rigidity to the tower for torquing operations (e.g., during application of counter-torque forces) and other operations. The distal portions 312*a*, 314*a* of the first tower 312 and/or second tower 314 can have a longitudinal length. The longitudinal length of the first tower 312 may be coaxially aligned along a first axis A2-A2. The longitudinal length of the second tower 314 may be coaxially aligned along a second axis A4-A4. In some embodiments, the first tower 312 and the second tower 314 can have different longitudinal lengths. Different longitudinal lengths may advantageously allow the intersection of the towers to be at or near the level of the skin in an operative state.

In some embodiments, the bend between the distal and proximal portions of any of the towers can optionally be adjustable using an adjustable coupling such as a locking hinge.

The first tower 312 can be configured to support a rod insertion device described in greater detail below. In some embodiments, the first tower 312 can be configured to support a rod insertion device above the distal portion of the first tower 312 (e.g., at or above the bend 352 of the first tower 312). The opening 323 of the first tower 312 may be coaxial with the distal portion 312*a* of the first tower 312. In some embodiments, the opening 323 may share the same cross-section as the interior of the distal portion 312*a* of the first tower 312. In some embodiments, the second tower 314 can also be configured to support the rod insertion device.

Figure 3A:
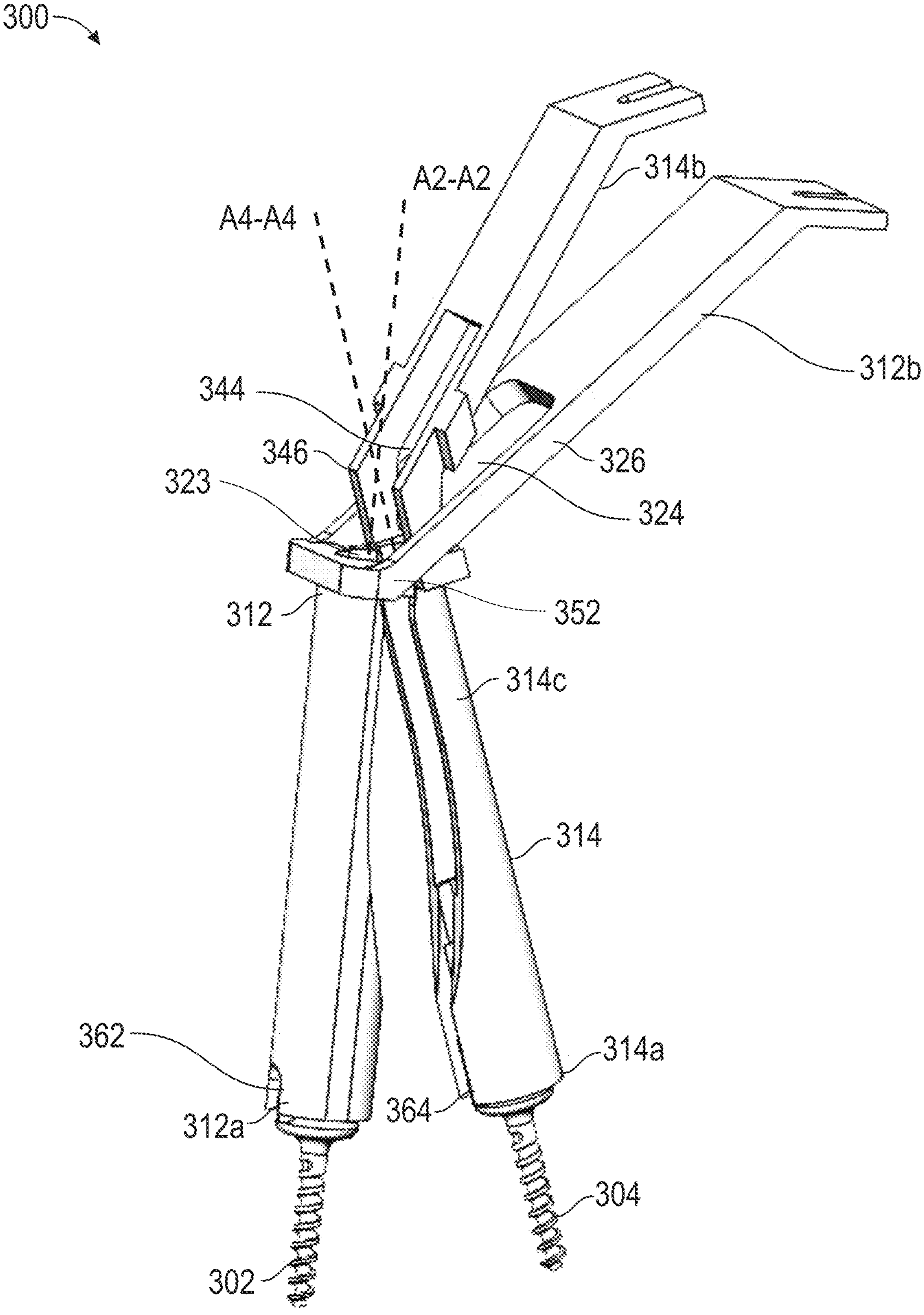
FIGS. 3A-3P illustrate another embodiment of a system for stabilizing spinal vertebrae comprising spinal screws.
Figure 3B:
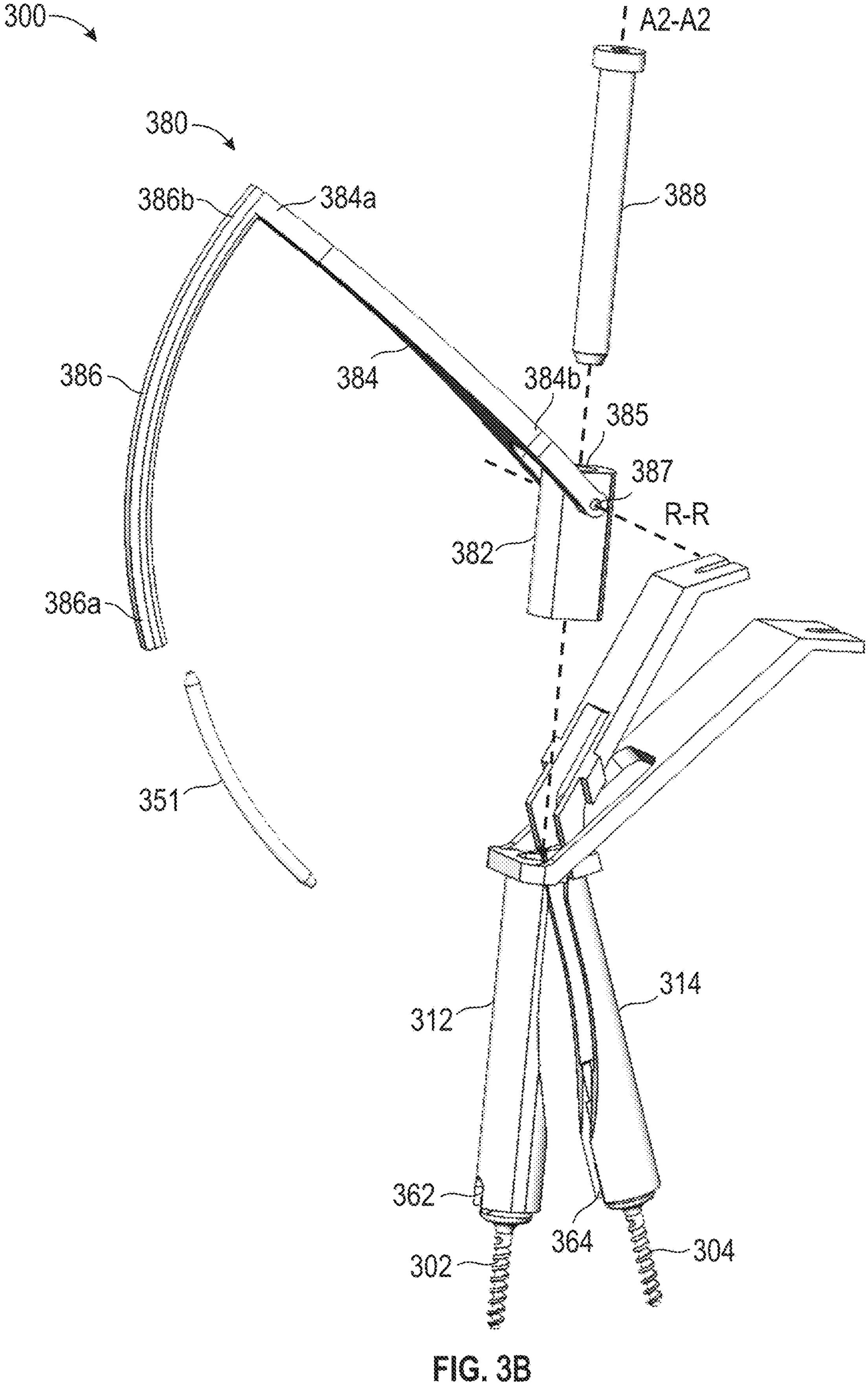

As shown in FIG. 3B, the system 300 may further include a connecting element 351 (also referred to herein as a connecting rod or just a rod) and a rod insertion device 380 that can include an insertable support pin 388. Some embodiments of the rod insertion device 380 can further include a body portion 382, a radial member 384 (also referred to herein as a rotating arm), and an arc member 386. The radial member 384 may further include a distal portion 384*a* and a proximal portion 384*b*. The arc member 386 may further include a proximal portion 386*a* and a distal portion 386*b*. In some examples, the rod insertion device 380 can be made from metal. For example, the one or more of the components of the rod insertion device 380 can be made from titanium (Ti) alloy, stainless steel, cobalt chrome, and/or molybdenum rhenium.

Some embodiments of the connecting element 351 may be the same as the connecting element 151, 251 described above. The connecting element 351 can be configured to extend between the first screw 302 and the second screw 304 in an operable state. In some embodiments, the connecting element 351 has a curvature along the longitudinal length of the connecting element 351. In some embodiments, the curvature of the connecting element 351 may be the same as the curvature of the arc member 386 of the rod insertion device 380 as described in greater detail below. The connecting element 351 may be also referred to as a rod, a support rod, and/or a spinal correction rod. The connecting element 351 can be configured to resist bending. For example, the connecting element 351 can be configured to resist torsion, flexion, and displacement along the length of the connecting element 351. In some examples, the connecting element 351 can be made of metal. For example, the connecting element 351 can be made of cobalt chromium, titanium alloy, and/or stainless steel. As shown in FIG. 3B, the connecting element 351 can include tapered ends. In some examples, the connecting element 351 can have different ends.

The body portion 382 may be configured to have a length in a longitudinal direction thereof that is shorter than, similar to, or longer than an effective length of the proximal portion 312*b* of the first tower 312 and/or the proximal portion 314*b* of the second tower 314. In some embodiments, the body portion 382 can increase the effective length of the distal portions 312*a*, 314*a* of the first tower 312 and/or the second tower 314 when coupled to the first tower 312 and/or second tower 314. The body portion 382 can have an opening or lumen 385 extending through a central portion of the body portion 382 in the longitudinal direction of the body portion 382. In some embodiments, the opening 385 can be threaded. In some embodiments, the opening 385 can be unthreaded (e.g., can have a smooth, continuous wall) and can have a constant diameter along the length of the lumen.

The body portion 382 can define a longitudinal length. In some embodiments, the longitudinal length of the body portion 382 can be adjustable so as to enable a user to adjust a position of the insertion rod relative to the screw heads. The body portion 382 may further include a hinge point or axis of rotation positioned along a rotational axis (defined by axis R-R as shown in FIG. 3B). The rotational axis R-R may be orthogonal to a longitudinal axis of the body portion 382.

For example and without limitation, the body portion 382 can include an opening (also referred to herein as a transverse opening) extending through the body portion 382 in a direction that is transverse to the longitudinal direction of the body portion 382. A shaft or pin 387 can extend through the transverse opening in the body portion to couple the radial member 384 to the body portion 382. In some embodiments, the body portion 382 can have a plurality of transverse openings extending through the body portion 382 at a range of different positions along the length of the body portion 382. In some embodiments, each of the plurality of transverse openings extending through the body portion 382 can be configured to receive the shaft or pin therein to permit a user to adjust a height of the radial member 384 relative to the screw head coupled with a tower by selecting a different transverse opening (e.g., higher or lower relative to an end surface of the body portion 382.

In some embodiments, the body portion 382 may have one of many possible longitudinal lengths. As described above, the first tower 312 and the second tower 314 may have different longitudinal lengths. The range of different lengths of the body portion 382 may be similar to the range of different longitudinal lengths of the first tower 312 and/or the second tower 314.

The radial member 384 may be configured as a lever arm for rotating the arc member 386. As described above, the radial member 384 may further include a distal portion 384*a* and a proximal portion 384*b*. The radial member 384 may include a longitudinal length extending between the distal portion 384*a* and the proximal portion 384*b*. In some embodiments, the proximal portion 384*b* can be configured to rotate relative to the body portion 382 and, in some embodiments, can include features or components to permit the radial member 384 to rotate relative to the body portion 382. For example and without limitation, the proximal portion 384*b* can include an opening configured to receive a shaft (such as shaft or pin 387) that the radial member 384 can rotate about. In some embodiments, the proximal portion 384*b* of the radial member 384 can include two prongs. The two prongs may further include a hinge point. In some embodiments, the hinge point is positioned along the rotational axis R-R. In some embodiments, the radial member 384 may be configured to rotate about the rotational axis R-R. The rotational axis R-R may be orthogonal to the longitudinal length of the radial member 384. In the operative state, the radial member 384 can extend along a common plane with the first tower 312, the second tower 314, and the third tower 316. Additionally, in the operative state, the radial member 384 can be configured to rotate about a rotational axis longitudinally displaced from the distal portions of the towers. For example, the body portion 382 can proximally displace the rotational axis R-R from the proximal end of the distal portions of the towers. In some embodiments, the rotational axis R-R can be longitudinally positioned between the proximal end of the proximal portion and the distal end of the proximal portion of the towers and aligned with the axial or longitudinal axis of the distal portion of the towers.

In some embodiments, the radial member 384 may have a fixed longitudinal length. Alternatively, in some embodiments, the radial member 384 may be adjustable so as to have an adjustable longitudinal length. In some embodiments, the radial member 384 can include telescoping members to permit the user to adjust a length of the radial member 384. For example and without limitation, the distal portion 384*a* may be configured to at least partially retract into and/or extend from the proximal portion 384*b*. Additionally and/or alternatively, the proximal portion 384*b* may be configured to at least partially retract into and/or extend from the distal portion 384*a*. In some embodiments, the longitudinal length of the radial member 384 may depend on the longitudinal length of the first tower 312 and/or the second tower 314 and the longitudinal length of the body portion 382. In some embodiments, the longer tower may need a radial member 384 with a longer longitudinal length to guide the connecting element 351 along an arcuate approach path to the window or slot 362, 364 of the first tower 312 and the second tower 314, respectively. In some embodiments, a locking or securing element (such as one or more set screws, one or more pins, or other fasteners) can be used to selectively secure the radial member 384 in the desired length.

As shown in FIG. 3B, the arc member 386 can be a curved member extending from the distal end of the radial member 384. The arc member 386 can extend in a tangential direction relative to the radial member 384. In some embodiments, the arc member 386 can have a length and curvature corresponding to at least a portion of a circumference based on the longitudinal length of the radial member 384. In some embodiments, the curvature of the arc member 386 can increase (i.e., to a larger radius) as the longitudinal length of the radial member 384 increases. In some embodiments, the curvature of the arc member 386 may be constant along the length of the arc member 386.

The arc member 386 can be hollow. In some examples, a lumen can extend at least partially through the length of the arc member 386. For example, a lumen can extend proximally from the distal end of the arc member 386 at least partially along the length of the arc member 386. The lumen may have an outer dimension exceeding the outer dimension of the connecting element 351. Accordingly, the connecting element 351 can be configured to be at least partially inserted within the lumen of the arc member 386. Inserting the connecting element 351 within the arc member 386 can secure the connecting element during insertion of the connecting element 351 as described herein.

The distal portion 386*a* of the arc member 386 may further include an engagement surface configured to engage with the connecting element 351, a trocar tip, or other devices, tools or bits. In some embodiments, the distal portion 386*a* further includes a lumen extending through the center of the arc member 386. The lumen can be configured to receive the connecting element 351. The dimensions of the lumen may be larger than the outer dimensions of the connecting element 351. In some embodiments, the lumen of the arc member 386 may be marginally larger than the outer dimensions of the connecting element 351 such that the connecting element 351 may be inserted within the lumen of the arc member 386 and secured in place via friction between the lumen and the connecting element 351.

The rod insertion device 380 may be assembled by aligning the proximal portion 384*b* of the radial member 384 with the hinge point of the body portion 382 such that the radial member 384 is configured to rotate about the rotational axis R-R. The proximal portion 386*b* of the arc member 386 may extend from the distal portion 384*a* of the radial member 384. In some embodiments, the proximal portion 386*b* arc member 386 extends tangentially from the distal portion 384*a* of the radial member 384. The longitudinal length of the radial member 384 may define a radius of a circumference defining a rotational path along which the arc member 386 may traverse as the radial member 384 rotates about the rotational axis R-R. Accordingly, in some embodiments, as the radial member 384 rotates about the rotational axis R-R, the arc member 386 traverses along an arcuate path. In some embodiments, the arcuate path may be a circumferential path defined at least in part by the longitudinal length of the radial member 384. In some embodiments, the circumferential path can follow at least a segment of a path 2*x* times the longitudinal length of the radial member 384.

In some embodiments, the rod insertion device 380 can be selectively securable or selectively dockable with the first tower 312 and/or the second tower 314 such that the rod insertion device 380 is not permanently fixed to the towers. Instead, the body portion 382 of the rod insertion device 380 can, in some embodiments, have an interface that is configured to couple with the top of the first tower 312 and/or the second tower 314. The rod insertion device 380 can be configured to rotate the arc member 386 so that the tip of the arc member 386 will rotate into the seat of at least the first and second screw heads.

The insertable support pin 388 may be an elongated device configured to be inserted within the lumen of the body portion 382 and secure the rod insertion device 380 to the first tower 312 and/or second tower 314. The insertable support pin 388 can have a longitudinal length exceeding the longitudinal length of the body portion 382. In some embodiments, the longitudinal length of the insertable support pin 388 may be sufficiently long to pass through the body portion 382 and engage with a distal portion 312*a* of the first tower 312 and/or the distal portion 314*a* of the second tower 314.

The insertable support pin 388 can have an outer dimension that is smaller (e.g., without limitation, slightly smaller) than the lumen of the body portion 382 and the opening 323. The support pin 388 can be configured to secure the body portion 382 to at least one of the first tower 312 and/or second tower 314. In some embodiments, the insertable support pin 388 can be threaded. The insertable support pin 388 can have threading corresponding to an internal threading of the body portion 382 and/or the distal portion 312*a*, 314*a* of the first tower 312 and/or second tower 314. In some embodiments, the insertable support pin 388 is not threaded and includes a constant outer diameter having a smooth, continuous surface along the longitudinal length of the insertable support pin 388. For example and without limitation, the insertable support pin 388 can be cylindrical having an outer diameter smaller than the diameter of the lumen of the body portion 382 and/or the distal portion 312*a*, 314*a* of the first tower 312 and/or second tower 314.

The insertable support pin 388 can further define an opening (also referred to herein as a lumen) extending through the longitudinal length of the insertable support pin. The lumen of the insertable support pin 388 may be sized to permit at least a distal portion of a tool configured to engage with the first screw 302 and/or second screw 304 to advance therethrough. In some embodiments, the insertable support pin 388 may include a tapered distal end and a flange at a proximal end. The tapered end may be configured to be inserted into the body portion 382. In some examples, the insertable support pin 388 may be fixedly incorporated into the body portion 382. In such embodiments, the support pin 388 may extend from the distal end of the body portion 382.

The rod insertion device 380 may be configured to engage with and be supported by the first tower 312 and/or second tower 314 and to rotatably insert the connecting element 351 within the windows or slots 362, 364 of the first tower 312 and the second tower 314, respectively. The connecting element 351 may then be secured to the first screw 302, the second screw 304, and/or the third screw.

As shown in FIG. 3B, the body portion 382 can be configured to selectively couple to the first tower 312. The body portion 382 and insertable support pin 388 may be aligned with the first longitudinal axis A2-A2 of the first tower 312 and advanced towards the distal portion 312*a* of the first tower 312. Alternatively, the body portion 382 and insertable support pin 388 may be aligned with another longitudinal axis corresponding to another tower.

Figure 3C:
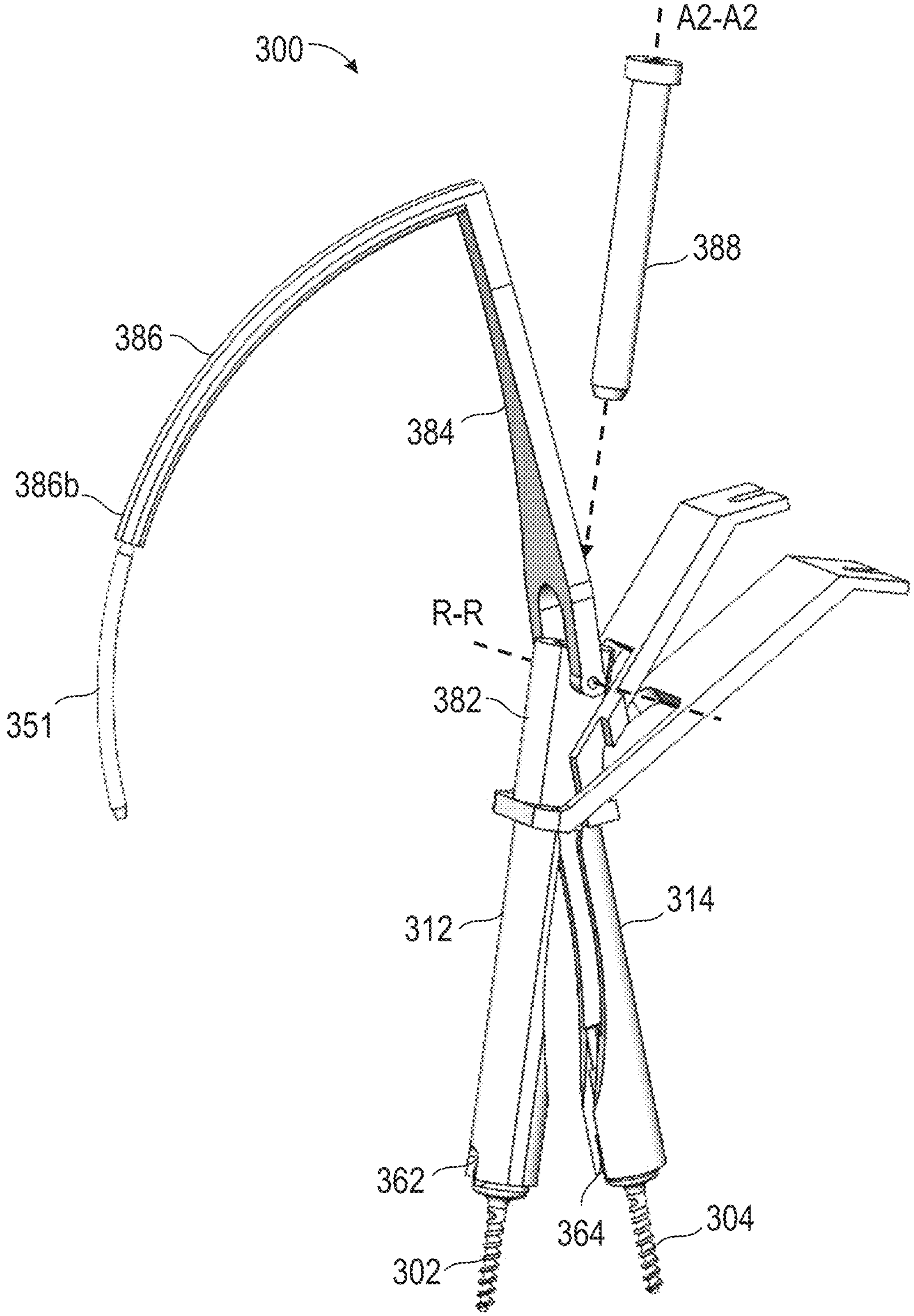

As shown in FIG. 3C, the connecting element 351 can be removably coupled with and supported by the distal portion 386*b* of the arc member 386. The insertable support pin 388 can then be inserted within the lumen of the body portion 382 and the opening of the first tower 312. The insertable support pin 388 may provide additional structural support to the body portion 382.

Figure 3D:
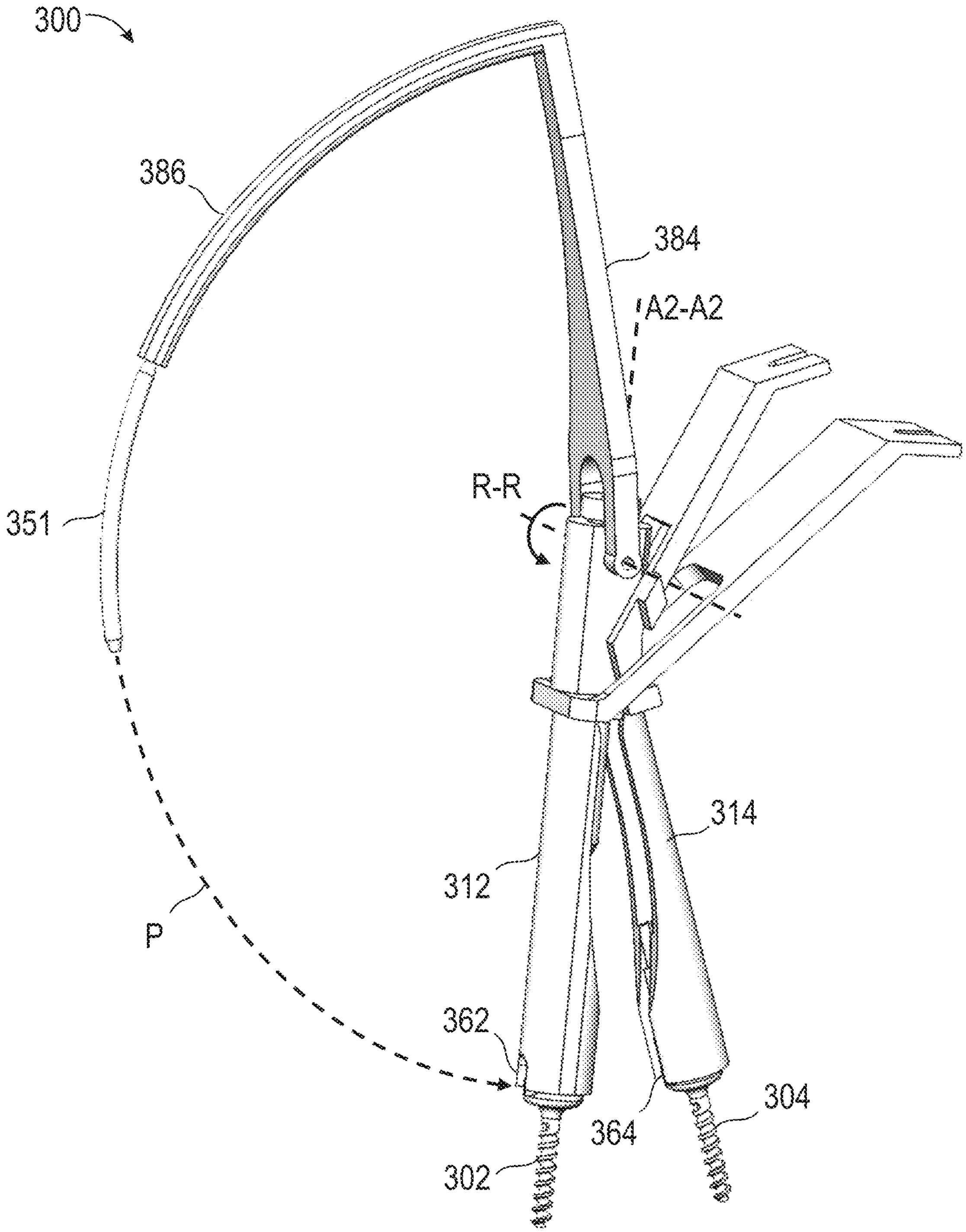

As shown in FIG. 3D, the rod insertion device 380 can be configured to rotate about the rotational axis R-R. The rotation of the rod insertion device 380 about the rotational axis R-R advances the connection element 351 about an arcuate path P toward the windows or slots 362, 364 of the first tower 312 and the second tower 314, respectively. In some embodiments, the arcuate path P may be a circumferential path. In some embodiments, the arcuate path P may be the circumferential path described above. In some embodiments, the rod insertion device 380 may be configured to advance a connection element 351 along the arcuate path P so that a tip of the connection element 351 advances into a seat of at least the first or second screw 302, 304 to of the corresponding first tower or the second tower 314 to which the rod insertion device 380 is coupled.

Figure 3E:
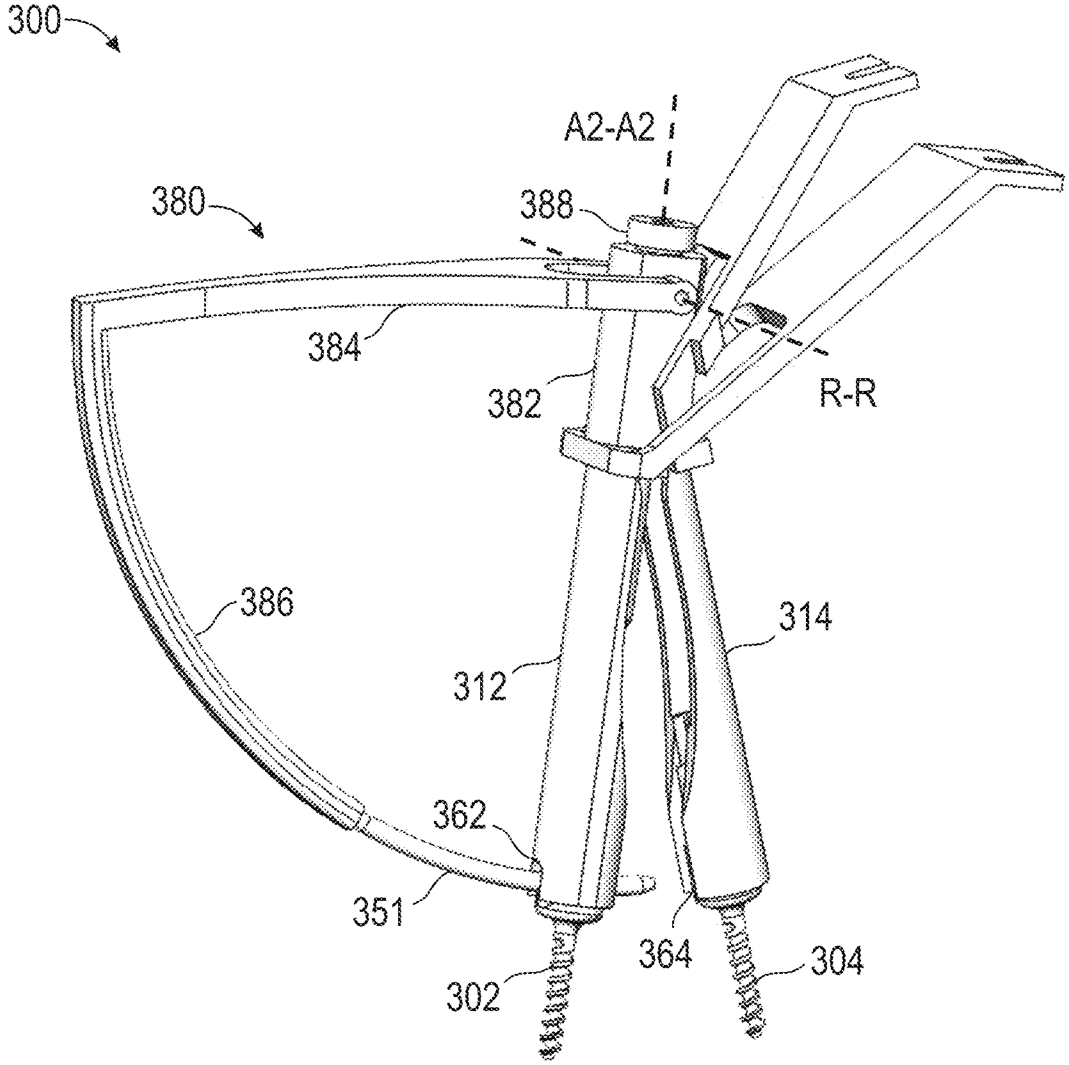
Figure 3F:
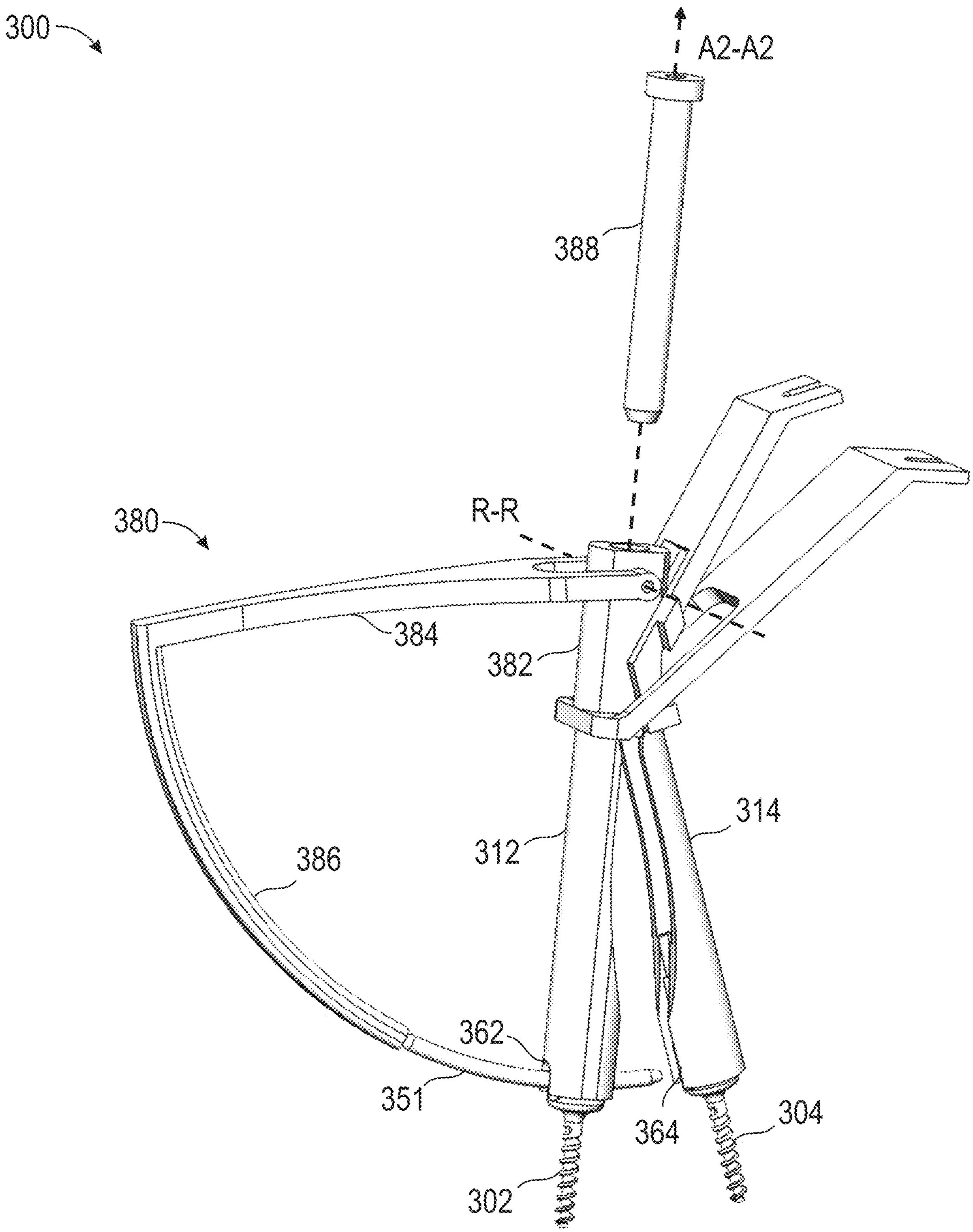
Figure 3G:
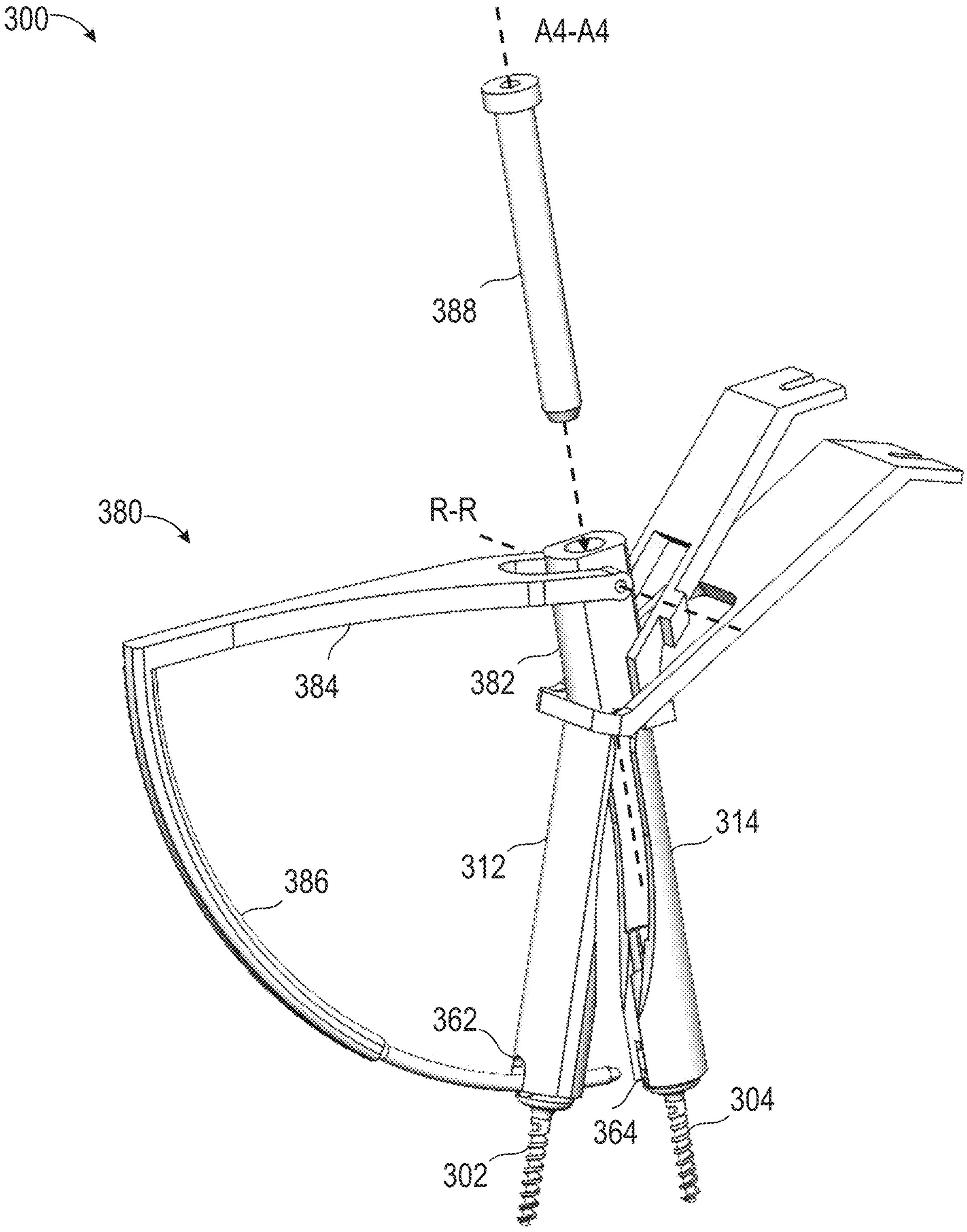

FIGS. 3E-3G illustrate an embodiment of sequential steps for inserting the connection element 351 within the first tower 312 and preparing for the insertion of the connection element 351 within the second tower 314. In some embodiments, the rod insertion device 380 may be coupled with the tower which will receive the connection element 351. For example and without limitation, the rod insertion device 380 may couple to the first tower 312 to pass the connection element 351 through the window or slot 362 and couple to the second tower 314 to pass the connection element 651 through the window slot 364. In some embodiments, the rod insertion device 380 may be removed from the first tower 312 after the tip of the connection element 351 passes through the window or slot 362 of the first tower and coupled to the second tower 314 for passing the tip of the connection element 351 through the window or slot 364 of the second tower 314. Inserting the connection element 351 one at a time may advantageously allow more adjustability of the position of the connection element 351 relative to the heads of the screws when the connection element is not perfectly aligned with the screw heads. For example and without limitation, coupling the rod insertion device 380 to the first tower 312 may permit the user to insert the connection element 351 within the window or slot 362 of the first tower 312 while coupling the rod insertion device 380 to the second tower 314 may insert the connection element 351 within a window or slot 364 of the second tower 314. Alternatively, any embodiments disclosed herein can be configured such that the rod insertion device 380 only needs to be coupled with one of the two or more towers to permit a user to insert the connection element 351 into two or more of the screw heads, or three of the screw heads.

As shown in FIG. 3E, the rotation of the rod insertion device 380 advances the connection element 351 through the first window or slot 362 of the first tower 312. In some embodiments, the rod insertion device 380 may continue to rotate about the rotational axis R-R to insert the connection element 351 into the window or slot 364 of the second tower 314.

As shown in FIG. 3F, the insertable support pin 388 can be removed from body portion 382 and tower to permit the rod insertion device 380 to be removed or decoupled from the tower. In some embodiments, the body portion 382 is then uncoupled from the first tower 312 after the connection element 351 has been rotated into the seat of the first screw 302. Removing the insertable support pin 388 permits the body portion 382 to be removed from the first tower 312.

As shown in FIG. 3G, the body portion 382 and the insertable support pin 388 can optionally then be aligned with the second axis A4-A4 corresponding to the longitudinal axis of the second tower 314. The body portion 382 is then optionally coupled to the second tower 314. As mentioned, any embodiments of the rod insertion device disclosed herein can be configured to permit a user to advance the connection element (also referred to as a rod or connecting rod) into two or three or more of the screw heads while the rod insertion device is coupled with only one of the towers.

Figure 3H:
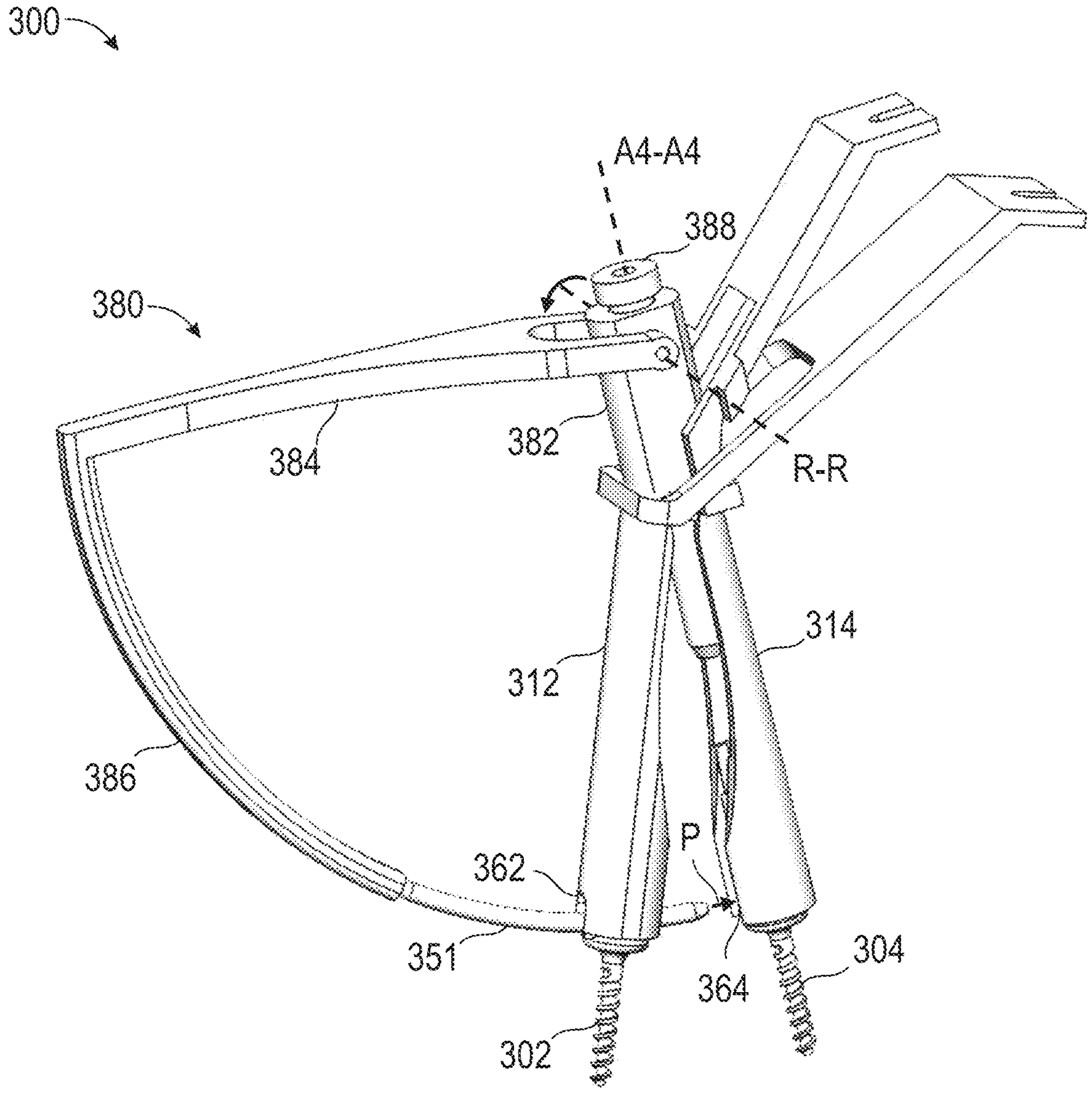
Figure 3I:
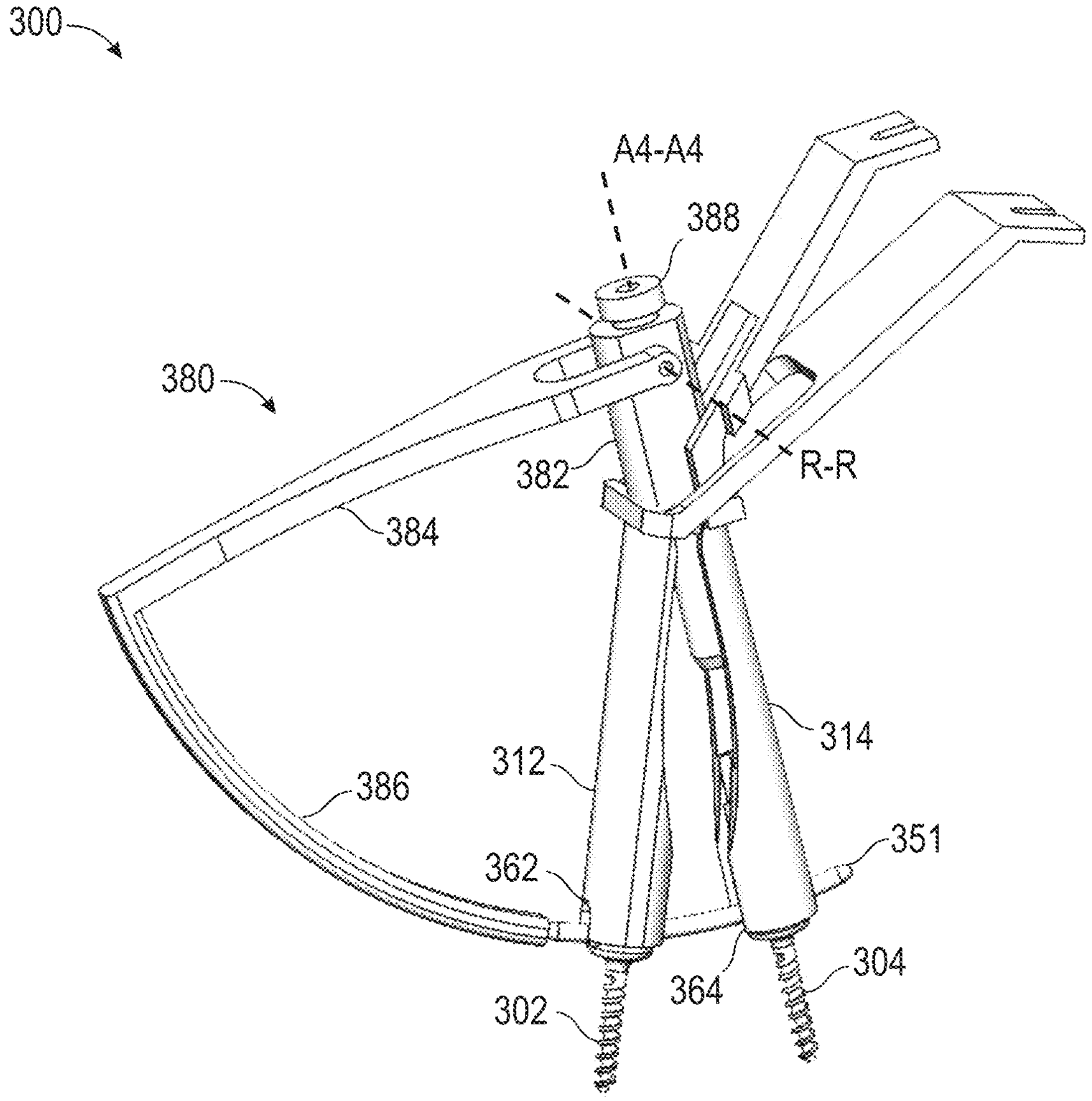

As shown in FIG. 3H, the rod insertion device 380 can be coupled to the second tower 314 and further rotated about the rotational axis R-R to insert the connection element 351 within the window or slot 364 of the second tower 314. The further rotation of the radial member 384 about the rotational axis R-R can advance the connection element 351 further about a circumferential path P toward the window or slot 364 of the second tower 314. FIG. 3I shows the tip of the connection element 351 extending through the window or slot 364 of the second tower 314.

FIGS. 3J-30 illustrate an embodiment of securing the connection element 351 to the first tower 312 and the second tower 314, respectively. After the connecting element 351 is inserted through the windows or slots 362, 364 of the first tower 312 and the second towers 314, respectively, and into engagement with at least the first and second screw heads, the connecting element 351 can secured in place via insert screws.

Figure 3J:
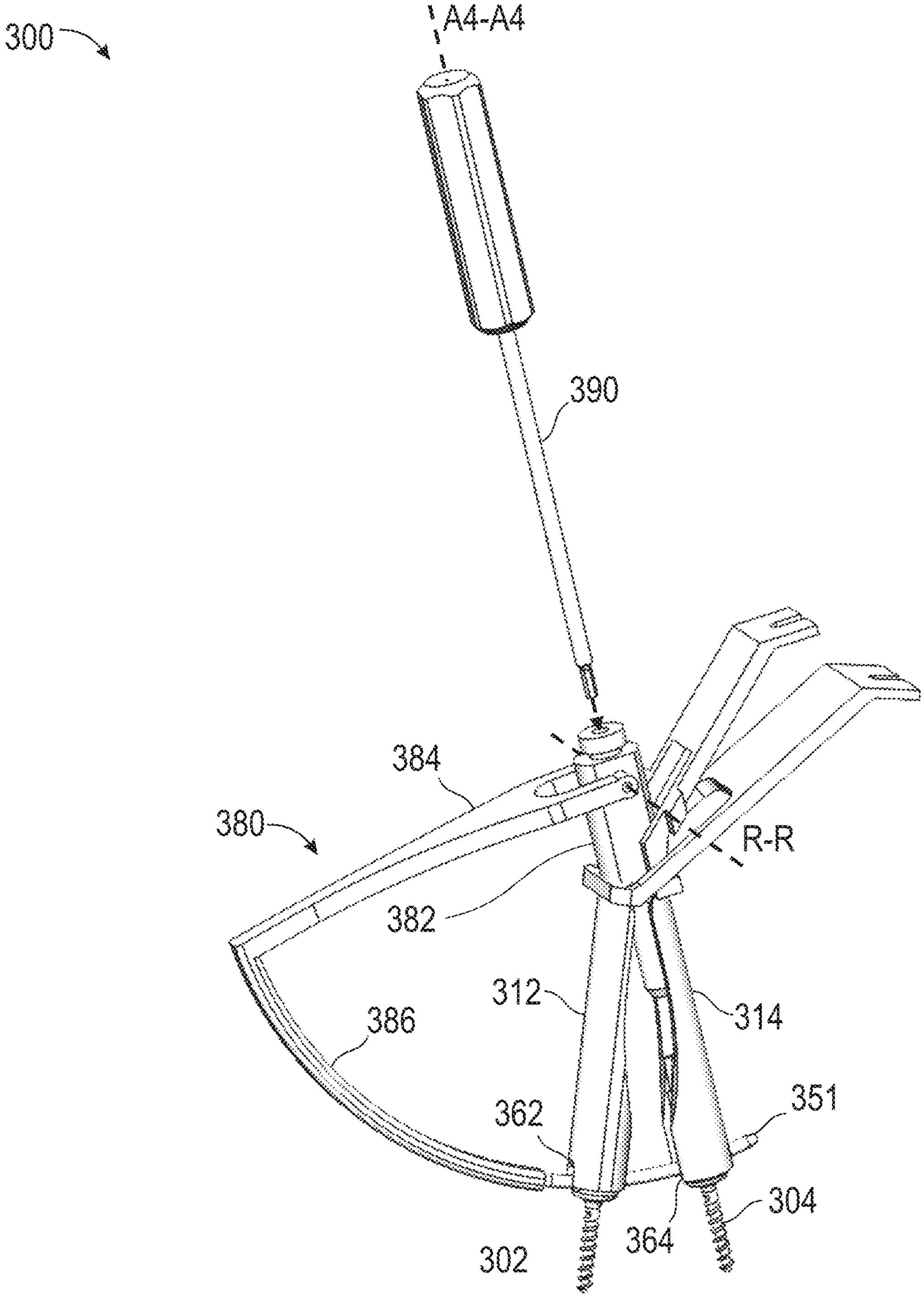

As shown in FIG. 3J, the rod insertion device 380 can be configured such that a tool 390 can be advanced through the insertable support pin 388, the body portion 382, and the tower (which can be, without limitation, the first tower 312 or the second tower 314) along the corresponding axis A2-A2, A4-A4. In some embodiments, an insert screw can be advanced through the rod insertion device 380. In some embodiments, the insert screw may be placed through the rod insertion device 380 using a guide and the tool 390. In some embodiments, the tool 390 may be a screwdriver. In some embodiments, the guide and the tool 390 could be separate instruments. In some embodiments, the guide and the tool 390 may be a unified tool. The insert screws may be inserted and locked into the screw heads of at least the first and/or second screws 302, 304 to secure the connection element 351 to the screw heads of at least the first and second screws. In some embodiments, the extended tabs may be reduction screws. This reduction may, in some embodiments, be important for spondylolisthesis.

Figure 3K:
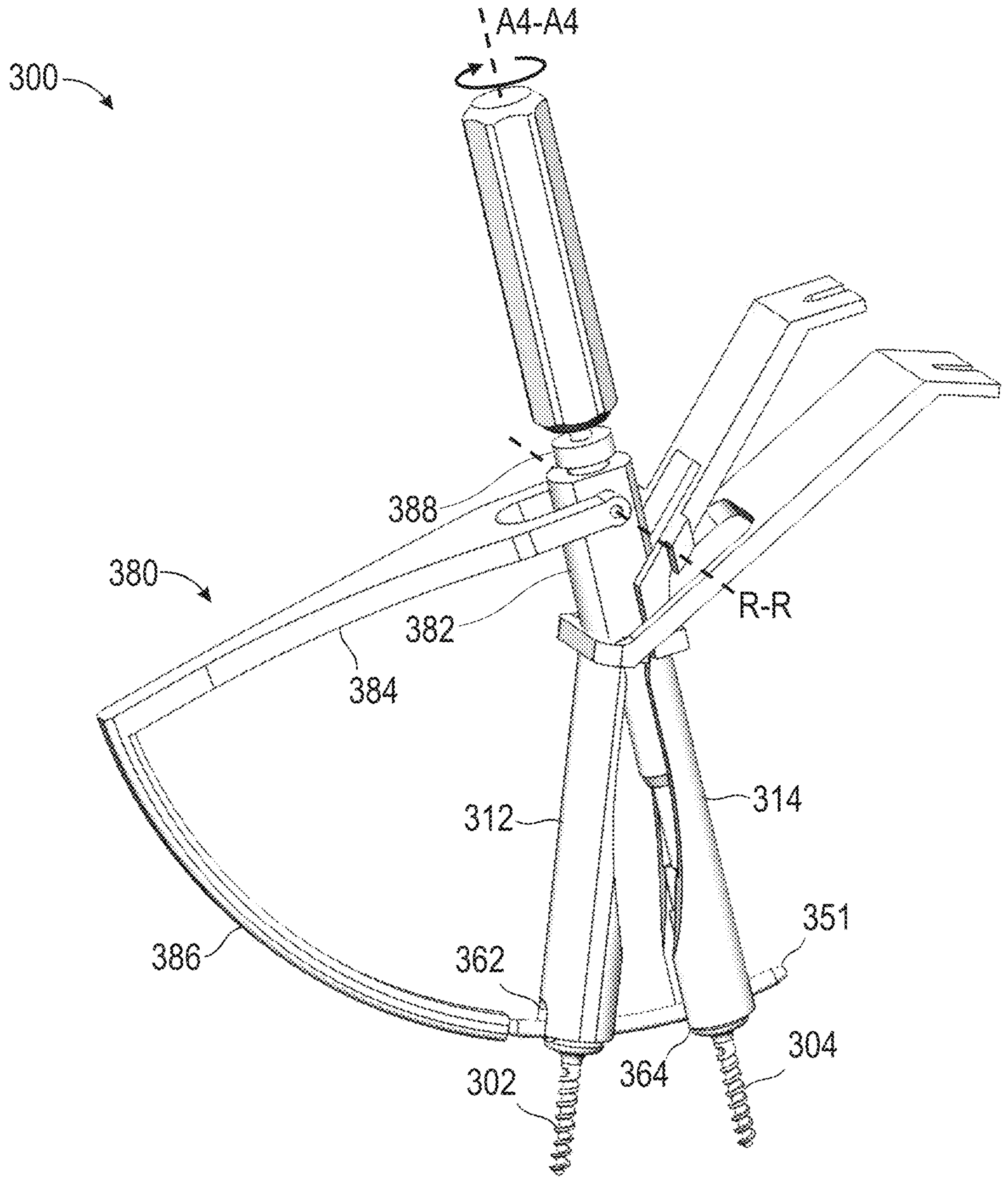

As shown in FIG. 3K, the tool 390 is actuated by rotating the tool 390 about the second axis A4-A4. Rotating the tool 390 may rotate an insert screw positioned at the distal end of the tool 390 between the screw head of the second screw 304 and the tip of the tool 390. In some embodiments, the rotation of the tool 390 may rotatably insert the insert screw within the screw head of the second screw 304 thereby securing the connection element 351 within the second screw 304. For example and without limitation, the insert screw may engage with threads of the screw head of the second screw 304 to secure the connection element 351 between the insert screw and the screw head of the second screw 304. After securing the connection element 351 between the insert screw and the screw head, the connection element 351 can be removed from the arc member 386 by reversely actuating the arc member 386. For example, the clamping force exerted on the connection element 351 can overcome a friction fit within the arc member 386.

Figure 3L:
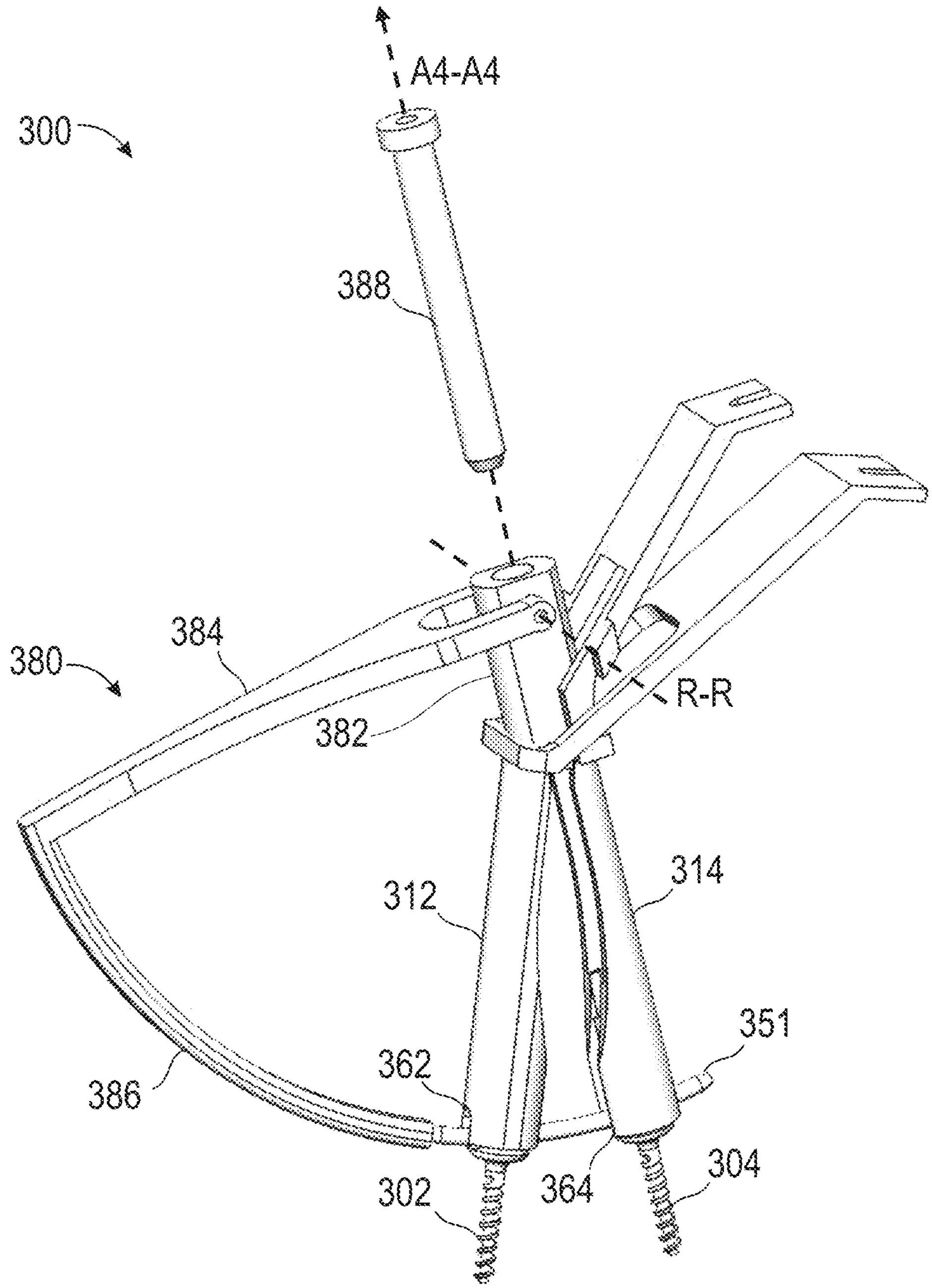

As shown in FIG. 3L, the tool 390 and insertable securing pin 388 may be removed from the second tower 314. The rod insertion device 380 may then be coupled to the first tower 312 to secure the connection element 351 to the first screw 302.

Figure 3M:
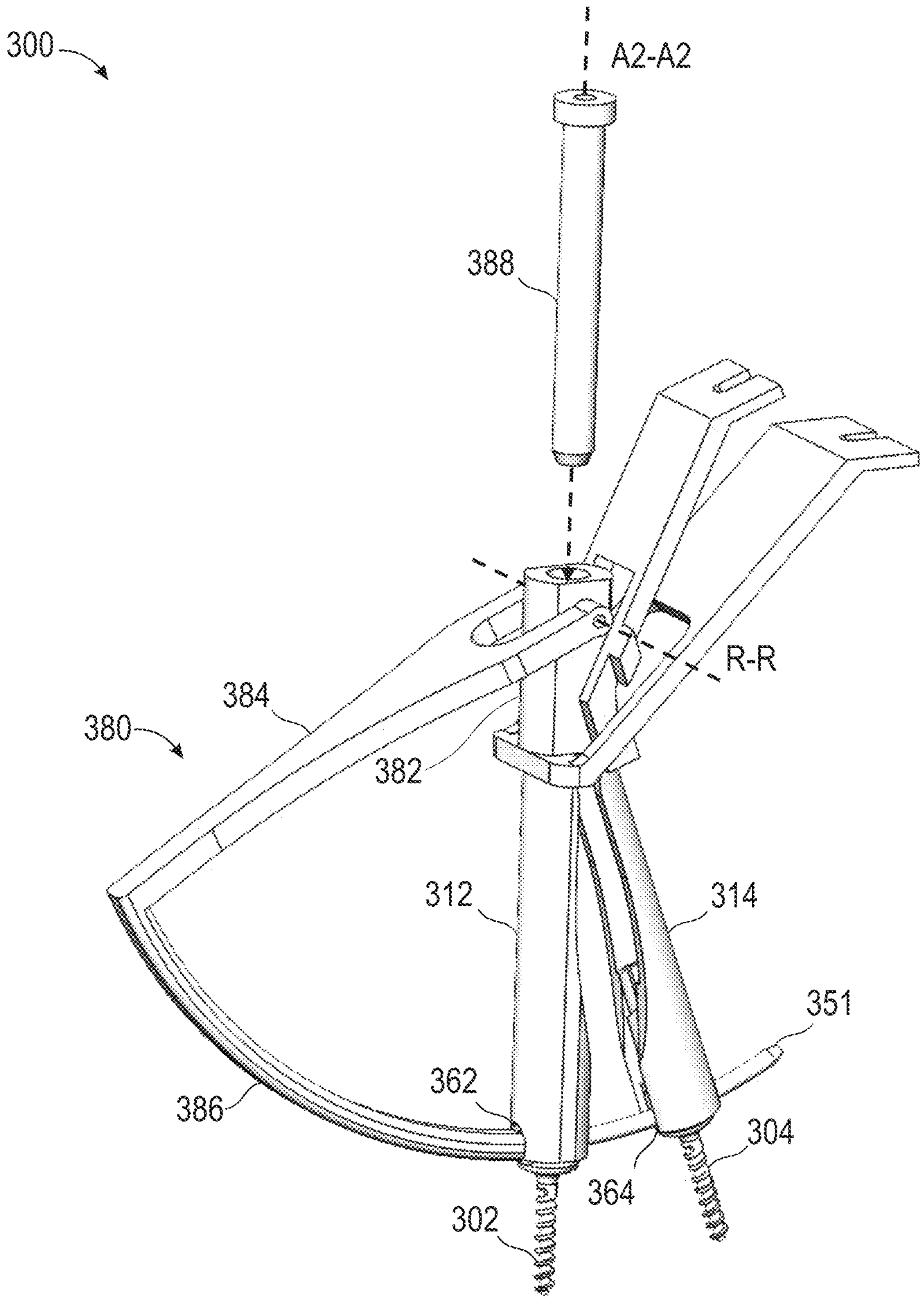

As shown in FIG. 3M, the rod insertion device 380 can then be engaged with the first tower 312, if needed or desired, by coupling the body portion 382 to the first tower 312. The insertable securing pin 388 can then be inserted within the lumen of the body portion 382 to secure the rod insertion device 380 to the first tower 312. Accordingly, the rod insertion tool 388 can be configured to be removably coupled to only one of the first tower 312 or the second tower 314 at a time.

Figure 3N:
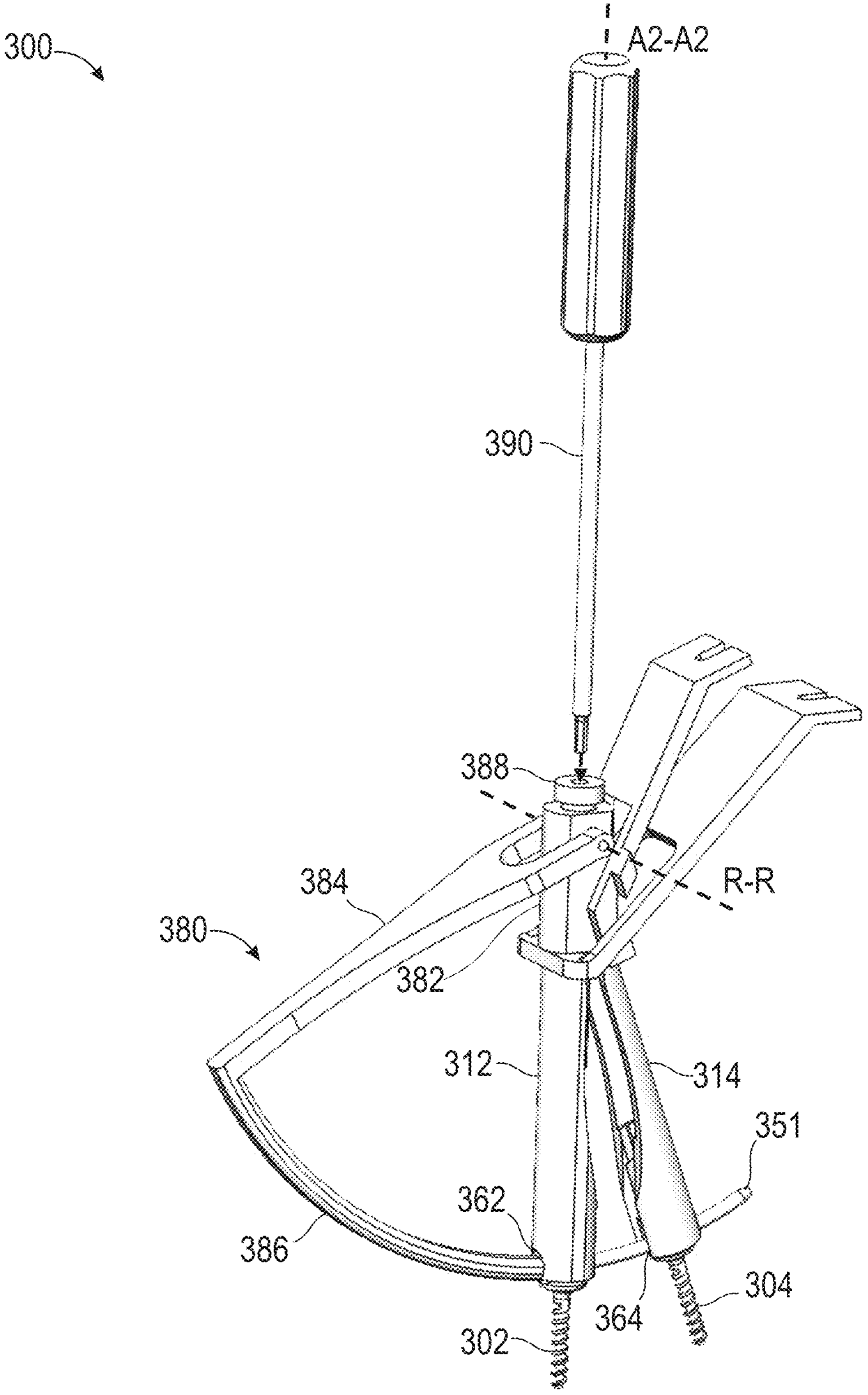

As shown in FIG. 3N, the tool 390 can be aligned with the lumen of the insertable support pin 388, the body portion 382, and the first tower 312 along the first axis A2-A2. The tool 390 can be inserted through the respective lumens of the insertable support pin 388, the body portion 382, and the first tower 312. In some embodiments, a screw (which can be an insert screw) can be placed through the rod insertion device 380. In some embodiments, the insert screw may be placed through the rod insertion device 380 using the guide and the tool 390. In some embodiments, the tool 390 may engage with the insert screw. In some embodiments, the insert screw can be prepositioned in a distal end of any tower so that the insert screw does not need to be advanced through the proximal end of any tower.

Figure 3O:
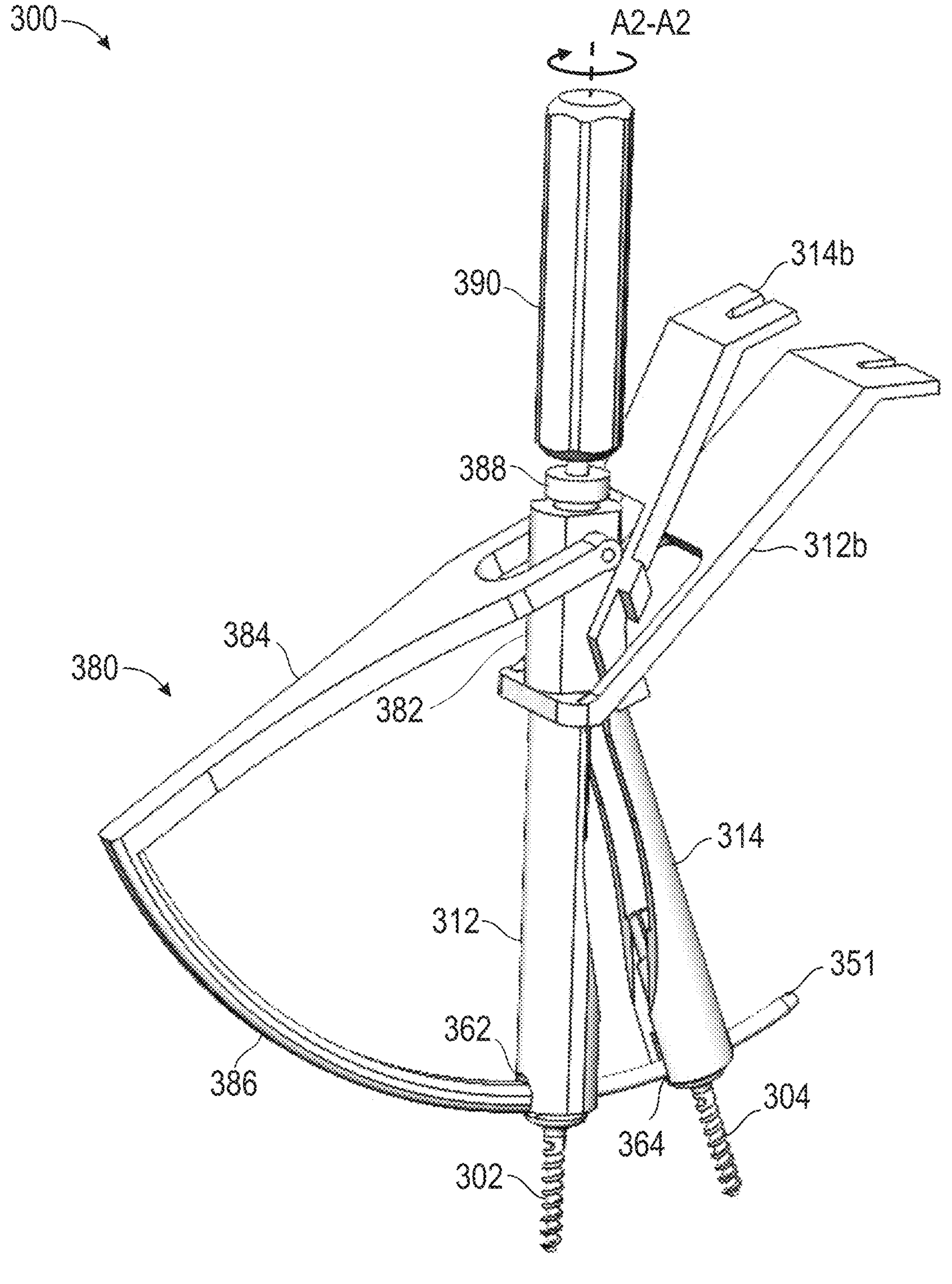

As shown in FIG. 3O, the tool 390 is actuated by rotating the tool 390 about the first axis A2-A2. Rotating the tool 390 may rotate the insert screw positioned at the distal end of the tool 390 between the screw head of the first screw 302 and the tip of the tool 390. In some embodiments, the rotation of the tool 390 may rotatably insert the insert screw within the screw head of the first screw 302 thereby securing the connection element 351 within the first screw 302. For example and without limitation, the insert screw may engage with threads of the screw head of the first screw 302 to secure the connection element 351 between the insert screw and the screw head of the first screw 302. In some embodiments, additional towers may be used. In such embodiments, similar steps may be repeated until the connection element 351 is secured to all towers.

The tool 390 may be removed from the first tower 312. The rod insertion tool may be rotated about the rotational axis R-R to disconnect the arc member from the connection element 351 and to advance the arc member away from the first tower 312. The insertable support pin and the rod insertion device 380 may be disconnected and removed from the first tower 312. Accordingly, the connection element 351 may be left in a secured position between the first tower 312 and the second tower 314, respectively. Before one or all of the insert screws are tightened, the first tower 312 and the second tower 314 may be moved or otherwise manipulated to apply compression or reduction to the vertebrae. In some embodiments, the proximal portions **312*b*, 314*b* may be manipulated to actuate the first tower and the second tower 314, respectively, before one or all of the insert screws are tightened. For example and without limitation, the first tower 302 and the second screw 304 may be compressed by squeezing the proximal portions 312*b*, 314*b* of the first tower 312 and the second tower 314** while locking the insert screws.

Figure 3P:
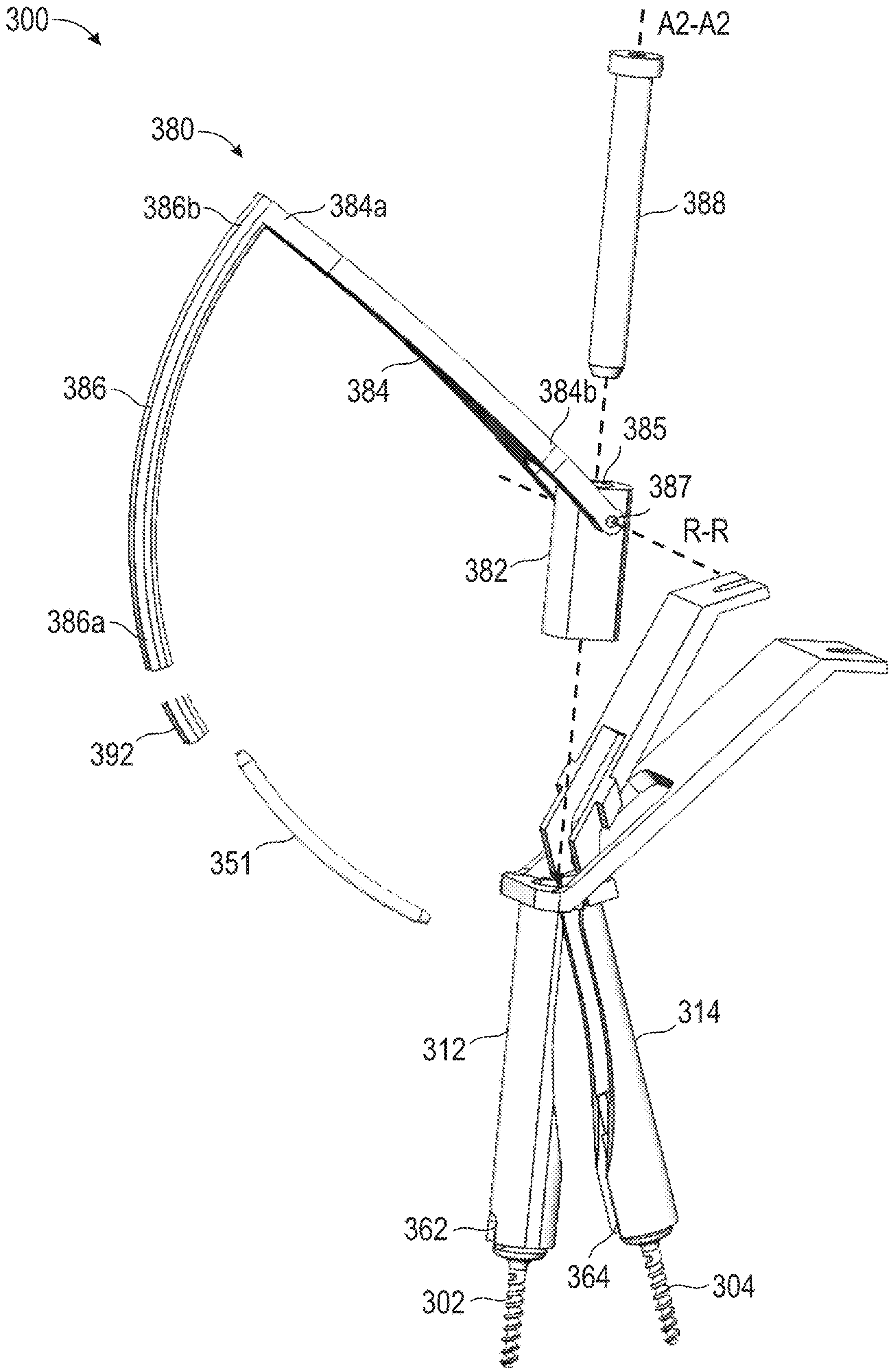

As shown in FIG. 3P, the system 300 may further include an interface member 392. The interface member 392 can couple to a distal end of the arc member 386 and can engage the connecting element 351. The interface member 392 can be referred to as an intermediate member or an intermediary member. In some examples, the interface member 392 can be an adapter configured to couple the arc member 386 to one of a variety of types of connecting elements 351. For example, the interface member 392 can be one of several designs. Each of the several designs can be configured to engage with a particular type of connecting element 351. For example, a first example design can include a lumen extending through the interface member 392, a second example design can include a divot and/or depression extending at least partially from the distal end of the interface member 392, a third example design can include a gear system. A particular interface member 392 can be selected based on the type of connecting element 351. Accordingly, the rod insertion device 380 can be a universal device configured to engage with a plurality of different connecting elements.

The interface member 392 can be made from one or more materials. The one or more materials can include titanium alloy, stainless steel, PEEK, and/or other polymer materials. In some examples, the interface member 392 can be a disposable element. Accordingly, the interface member 392 can be a single-use component. In some examples, the interface member 392 can be sterilized. Accordingly, the interface member 392 can be a multi-use element.

The interface member 392 can have a similar profile and curvature as the arc member 386. For example, the interface member 392 can have the same or similar cross-sectional shape as the arc member 386. In some examples, the interface member 392 can have a radial profile no greater than the arc member 386. In such examples, the interface member 392 can more readily pass through tissue.

Systems, Devices and Methods of FIGS. 4A-4J

Additional embodiments of a system 400 that can be used for stabilizing or treating spinal vertebrae through a skin incision S are disclosed below. In any embodiments disclosed herein, any components, features, or other details of the system 400 can have any of the components, features, or other details of any other system embodiments disclosed herein or be used according to any of the steps of any other method embodiments disclosed herein, including without limitation the embodiments of the systems 100, 200, 300 or methods of use thereof described herein, in any combination with any of the components, features, or details of the systems 100, 200, 300 or methods of use disclosed herein.

Some embodiments of the system 400 for stabilizing spinal vertebrae through a skin incision S can include two or more screws and a corresponding number of towers. In some embodiments, the system 400 may include the same or substantially similar tower configuration as systems 100, 200, 300.

Figure 4A:
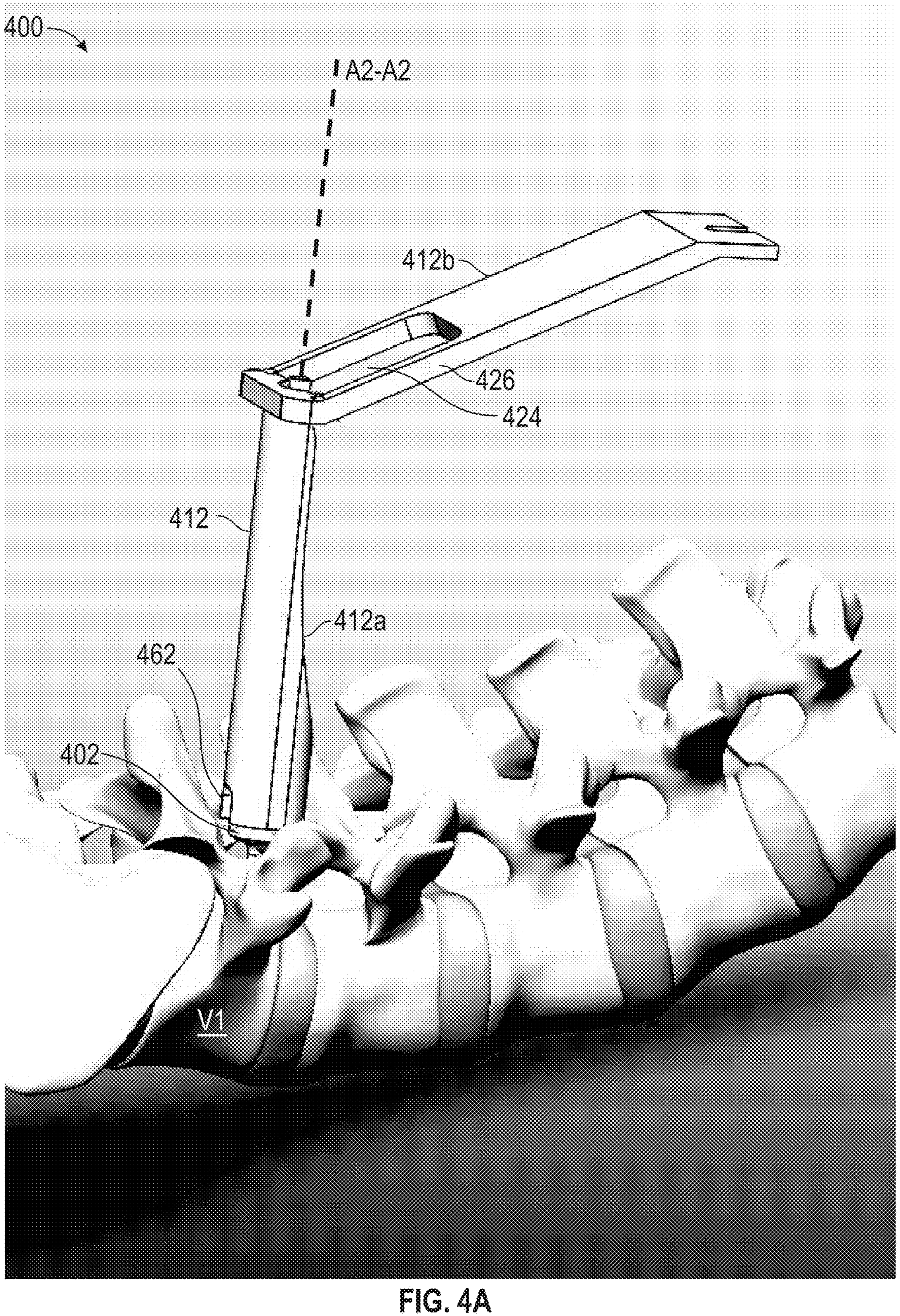
FIGS. 4A-4J illustrate another embodiment of a system for stabilizing spinal vertebrae comprising spinal screws.

As shown in FIG. 4A, the system 400 can include a first screw 402 and a first tower 412 having a distal portion 412*a*, a proximal portion 312*b*, and an opening or cutout 424 formed through a wall portion 426 of the proximal portion 412*b* of the first tower 412. In some embodiments, the first tower 412 can have an opening or window 462 (also referred to herein as a slot) in the distal portion 412*a* of the first tower 412.

In some embodiments, the first screw 402 may be the same or similar to the first screws 102, 202, 302. In some embodiments, the first tower 412 may be the same or similar to the first towers 112, 212, 312 such that the distal portion 412*a*, window or slot 462, the proximal portion 412*b*, the cutout 444, and the wall portion 446 may correspond to the distal portions 112*a*, 212*a*, 312*a*, the window or slot 162, 262, 362, the proximal portions 112*b*, 212*b*, 312*b*, the cutouts 124, 224, 324, and the wall portions 126, 226, 326, respectively.

Additionally, the first tower 412 can include an opening 423 that permits access to the inside of the distal portion 412*a* of the first tower 412. The opening 423 may be the same or similar to the opening 323. A longitudinal axis A2-A2 can extend through a longitudinal centerline of the distal portion 412*a* of the first tower 412. As further shown in FIG. 4A, the first screw 402 can be inserted within a first vertebra V1. The first tower 412 can be inserted through an incision in the skin and advanced to insert the first screw 402 within the first vertebra V1.

Figure 4B:
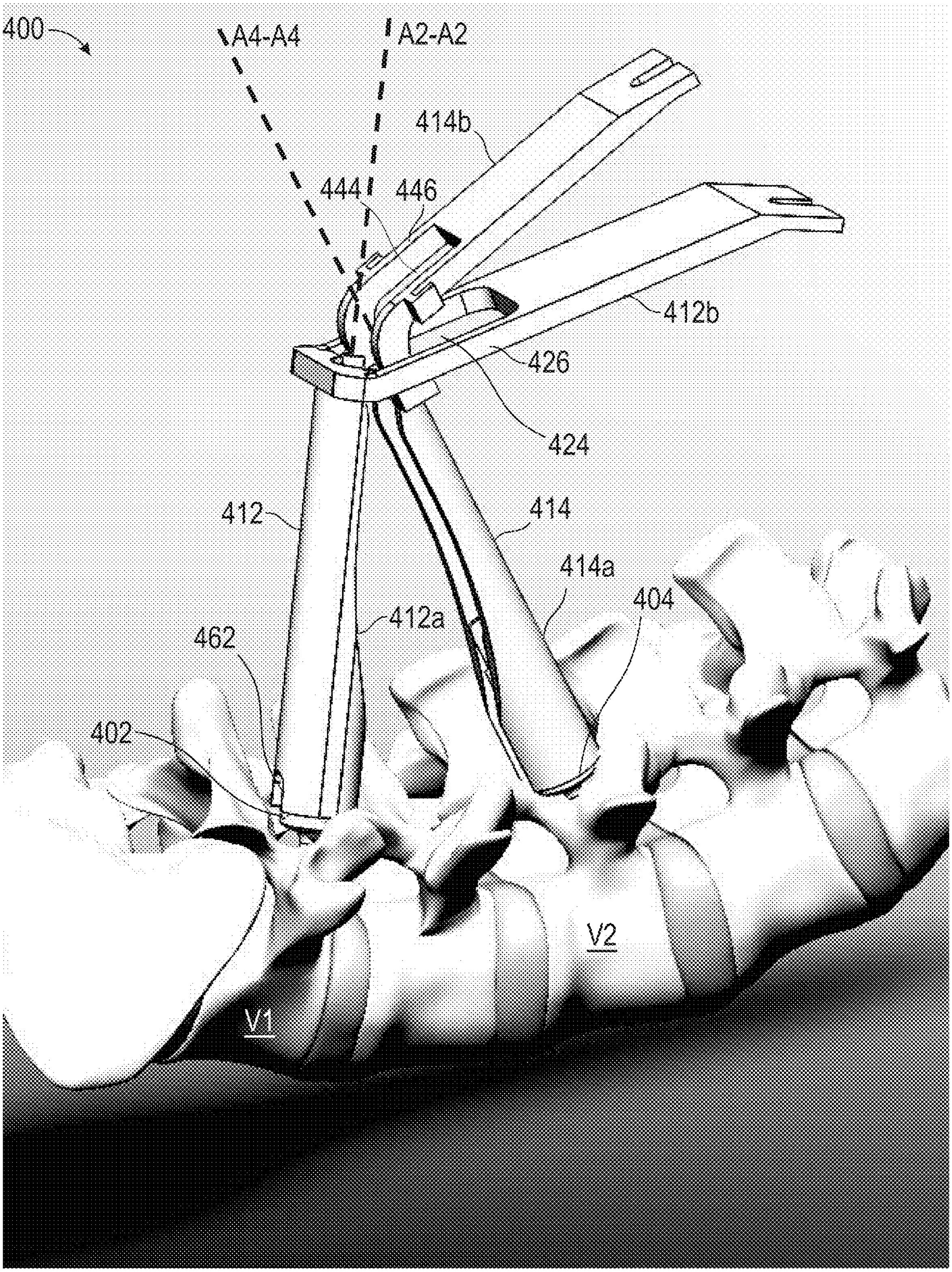
Figure 4C:
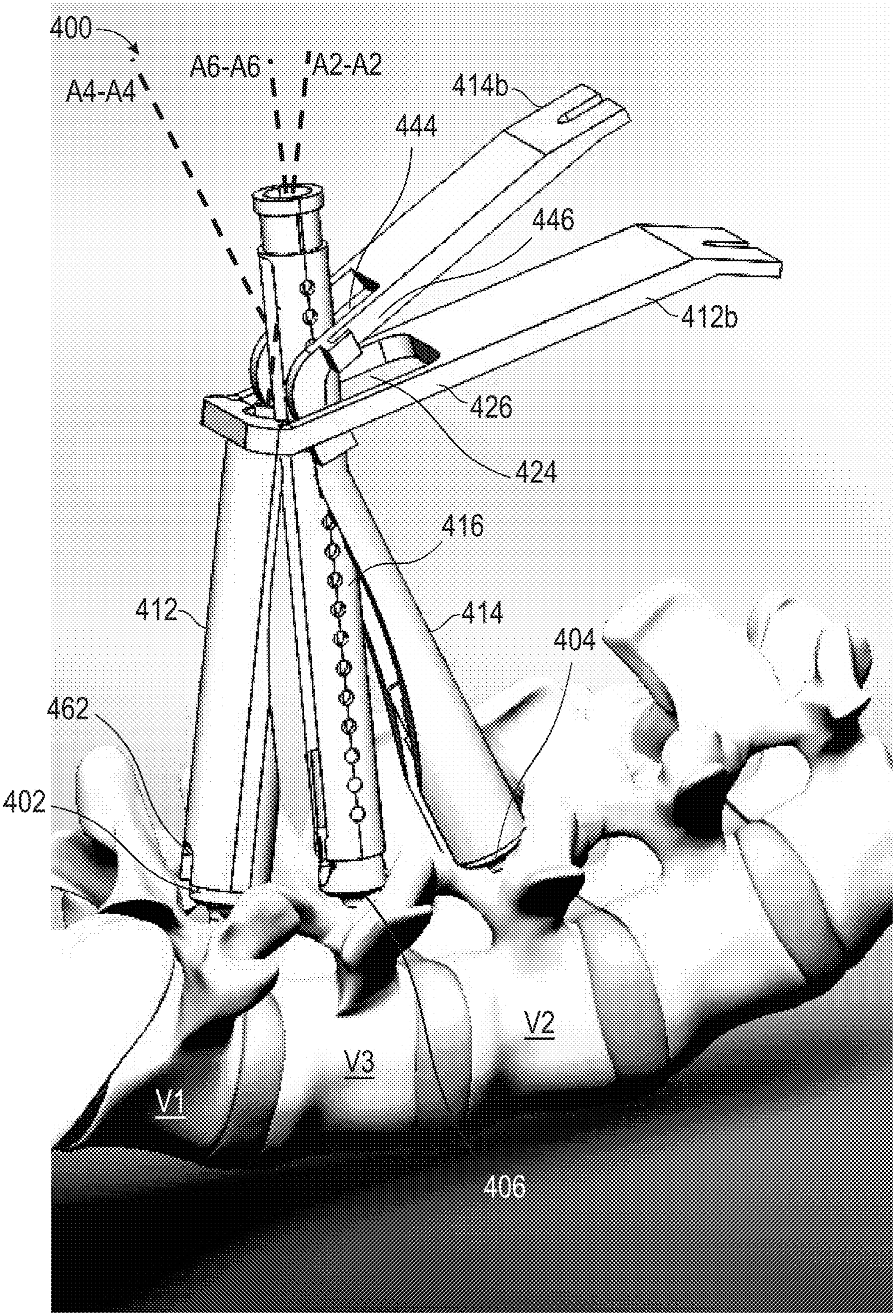

As shown in FIG. 4B, the system 400 can further include a second screw 404 and a second tower 414 having a distal portion 414*a*, a proximal portion 414*b*, and an opening or cutout 444 formed through a wall portion 446 of the proximal portion 414*b* of the second tower 414. In some embodiments, the second tower 414 can have an opening or window 464 (also referred to herein as a slot) in the distal portion 414*a* of the first tower 414.

In some embodiments, the second screw 404 may be the same or similar to the second screws 104, 204, 304. In some embodiments, the second tower 414 may be the same or similar to the second towers 114, 214, 314 such that the distal portion 414*a*, the window or slot 464, the proximal portion 414*b*, the cutout 444, and the wall portion 446 may correspond to the distal portions 114*a*, 214*a*, 314*a*, the window or slot 164, 264, 364, the proximal portions 114*b*, 214*b*, 314*b*, the cutouts 144, 244, 344, and the wall portions 146, 246, 346, respectively.

Additionally, the second tower 314 can include an opening that permits access to the inside of the distal portion 414*a* of the second tower 414. A longitudinal axis A4-A4 can extend through a longitudinal centerline of the distal portion 414*a* of the second tower 414. As further shown in FIG. 4B, the second tower 414 can be coupled to the second screw 402 which can be inserted within a second vertebra V2, wherein the second tower 414 can be advanced through the cutout 424 formed in the first tower 412. The second tower 414 may be inserted through an incision in the skin via the cutout 424 formed in the first tower 412 and advanced to insert the second screw 404 within the second vertebra V2. In some embodiments, the incision for the second tower 414 may be the same as the incision for the first tower 412. In some embodiments, the second vertebra V2 may be positioned adjacent to the first vertebra V1. Alternatively, in some embodiments, an intermediate vertebra may be positioned between the first vertebra V1 and the second vertebra V2.

As shown in FIG. 4C, the system 400 can further include a third screw 406 and a third tower 416. In some embodiments, the third screw 406 may be the same or similar to the third screws 106, 206, 306. In some embodiments, the third tower 416 may be the same or similar to the third towers 116, 216 described above. Additionally, the third tower 316 can have an opening that permits access to the inside of the third tower 416. A longitudinal axis A6-A6 can extend through a longitudinal centerline of the third tower 416. In some embodiments, the third tower 416 may further include one or more extended tabs and one or more wires extending from the one or more extended tabs. The one or more extended tabs and the one or more wires can enable the third tower 416 to decouple and then realign and recouple to the third screw 406. In some embodiments, the third tower 416 may be removed from the third screw if the third tower obstructs the movement of the rod insertion device. The extended tabs and wires facilitate alignment of the third tower with the third screw once the user desires to recouple the third tower with the third screw. Additionally, in any embodiments disclosed herein, the system can be configured so that that the rod insertion device can couple with the third tower (e.g., the middle tower).

As further shown in FIG. 4C, the third tower 416 can be coupled to the third screw 406 which can be inserted within a third vertebra V3, wherein the third tower 416 can be advanced through the cutouts 424, 444 formed in the first tower 412 and the second tower 414, respectively. The third tower 416 can be inserted through an incision in the skin via the cutout 424 formed in the first tower 412 and the cutout 444 formed in the second tower 414 and advanced to insert the third screw 406 within the third vertebra V3. In some embodiments, the incision for the third tower 416 may be the same as the incision for the first tower 412 and the second incision 414. In some embodiments, the third vertebra V3 may be positioned adjacent to the first vertebra V1 and the second vertebra V2.

As described herein with respect to FIGS. 1A-1G, each of the first tower 412, the second tower 414, and the third tower 416 can arranged along a respective plane. In some examples, the first tower 412, the second tower 414, and the third tower 416 can be coplanar in an operative state. For example, as shown in FIG. 4C, the first tower 412, the second tower 414, and the third tower 416 can be coplanar along the direction of the patient's spine in the operative state.

As further shown in FIG. 4B, the proximal portion 412*b* of the first tower 412 and the proximal portion 414*b* of the second tower 414 can extend in the direction of the spine. In some examples, the proximal portion 412*b* can extend a first distance in the direction of the spine and the proximal portion 412*c* can extend a second distance in the direction of the spine. In some examples, the position of the proximal ends of the towers relative to the direction of the spine can change via actuation of the towers. As described herein, the proximal portion 412*b* and the proximal portion 414*b* of the first tower 412 and the second tower 414, respectively, can be used as a handle. The handle can be used to exert a force on the distal ends of the towers to compress and/or expand the distance between adjacent vertebrae. Accordingly, adjusting the proximal portions closer together can separate distal ends of the towers and adjusting the proximal portions away from one another can close the distance between the distal portions and corresponding vertebrae. The motion of the proximal portions can change the axial position of the proximal portions relative to the direction of the spine.

Figure 4D:
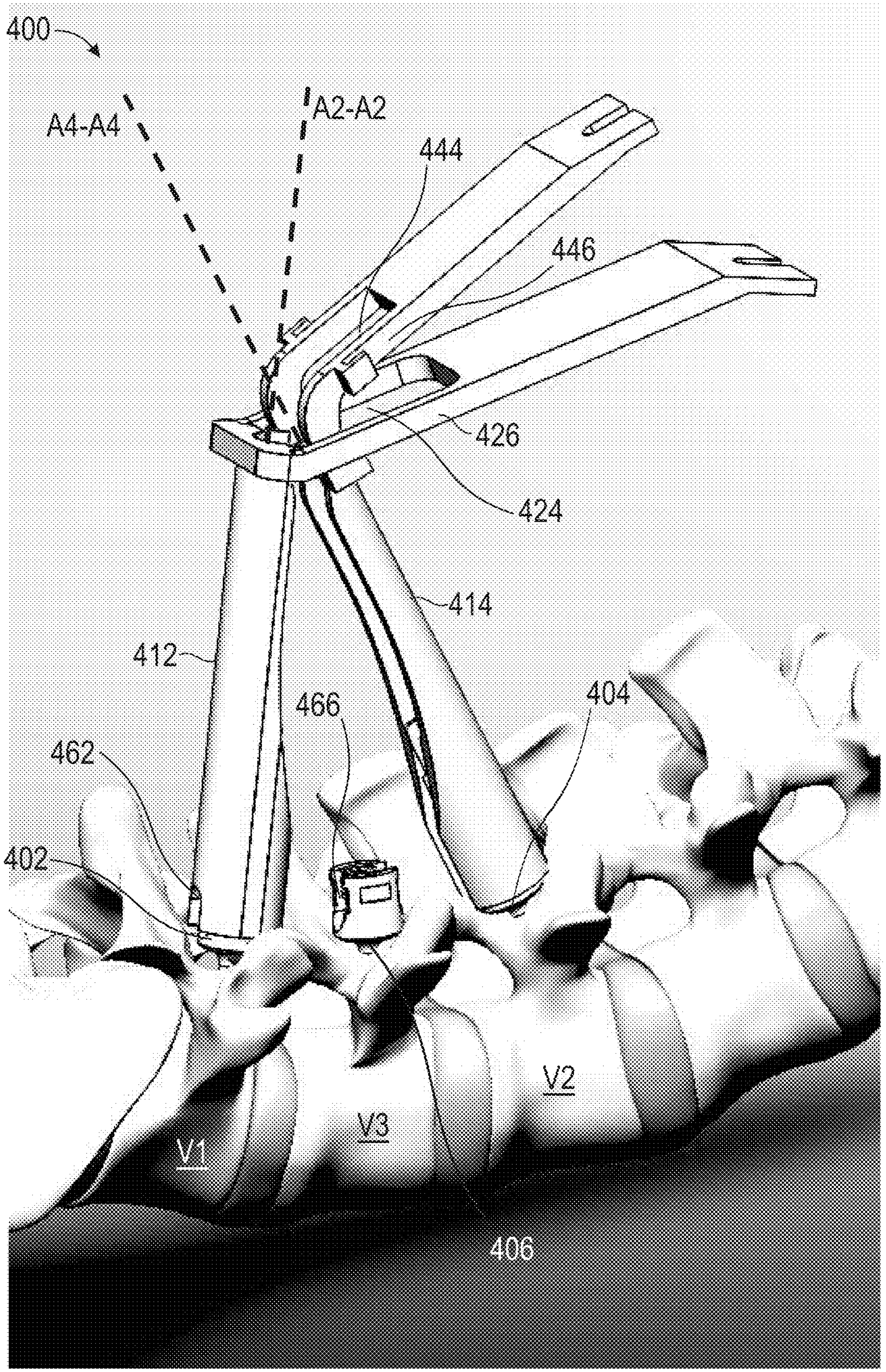
Figure 4E:
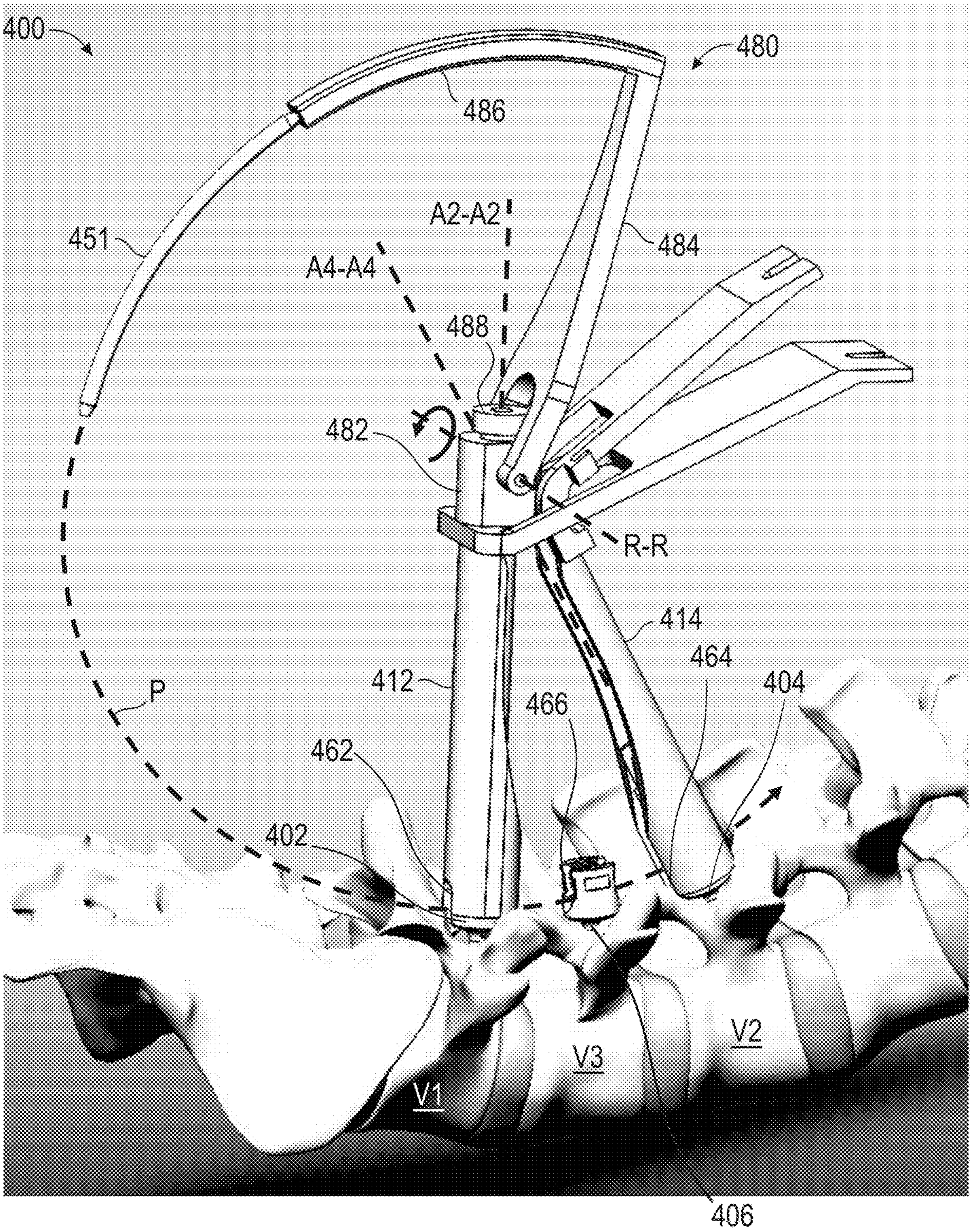

As shown in FIGS. 4D-4E, the third tower 416 can be removed, leaving the third screw 406 inserted within the third vertebra V3. Removing the third tower 416 can provide space for a rod insertion device 480 to couple to the first tower 412 or the second tower 414. In some embodiments, the third tower 416 may remain and the rod insertion device 480 may couple to the third tower 416. The rod insertion device 480 can include a body portion 482, a radial member 484, and an arc member 486. The rod insertion device 480 can be configured to advance a connection element 451 toward the first screw 402, the second screw 404, and/or the third screw 406. In some embodiments, the rod insertion device 480 can be coupled to the first tower 412. The rod insertion device 480 can be secured to the first tower 412 via an insertable support pin 488.

In some embodiments, the rod insertion device 480 may be the same or similar to the rod insertion device 380 described above such that the body portion 482, the radial member 484, and the arc member 486 may be the same or similar to the body portion 382, the radial member 384, and the arc member 386, respectively. In some embodiments, the insertable support pin 488 may be the same or similar to the insertable support pin 388 described above. In some embodiments, the connection element 451 may be the same as or similar to the connection element 151, 251, 351 described above.

The radial member 484 may be configured as a lever arm for rotating the arc member 486 about a rotational axis R-R. The rotation of the radial member 484 can advance the arc member 486 along an arcuate path P. In some embodiments, the arcuate path P may be the same or similar to the arcuate path P described above. In some embodiments, the arcuate path P may intersect the skin at a surgical site positioned distally of the incision for the first tower 412. In some embodiments, the arcuate path P may intersect the axes A2-A2, A4-A4, A6-A6 at points corresponding to seats of the first screw 402, the second screw 404, and the third screw 406, respectively.

Figure 4F:
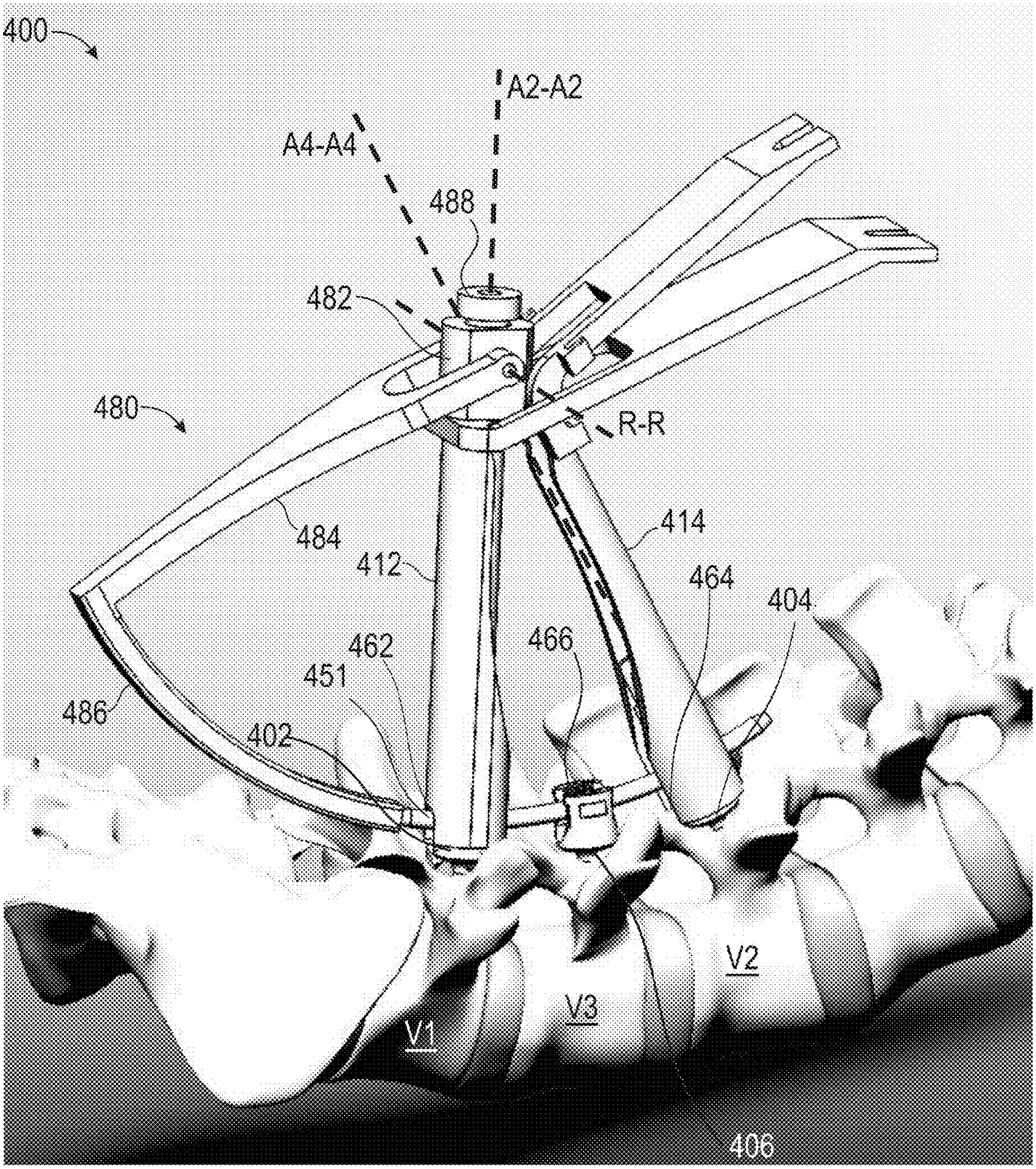
Figure 4G:
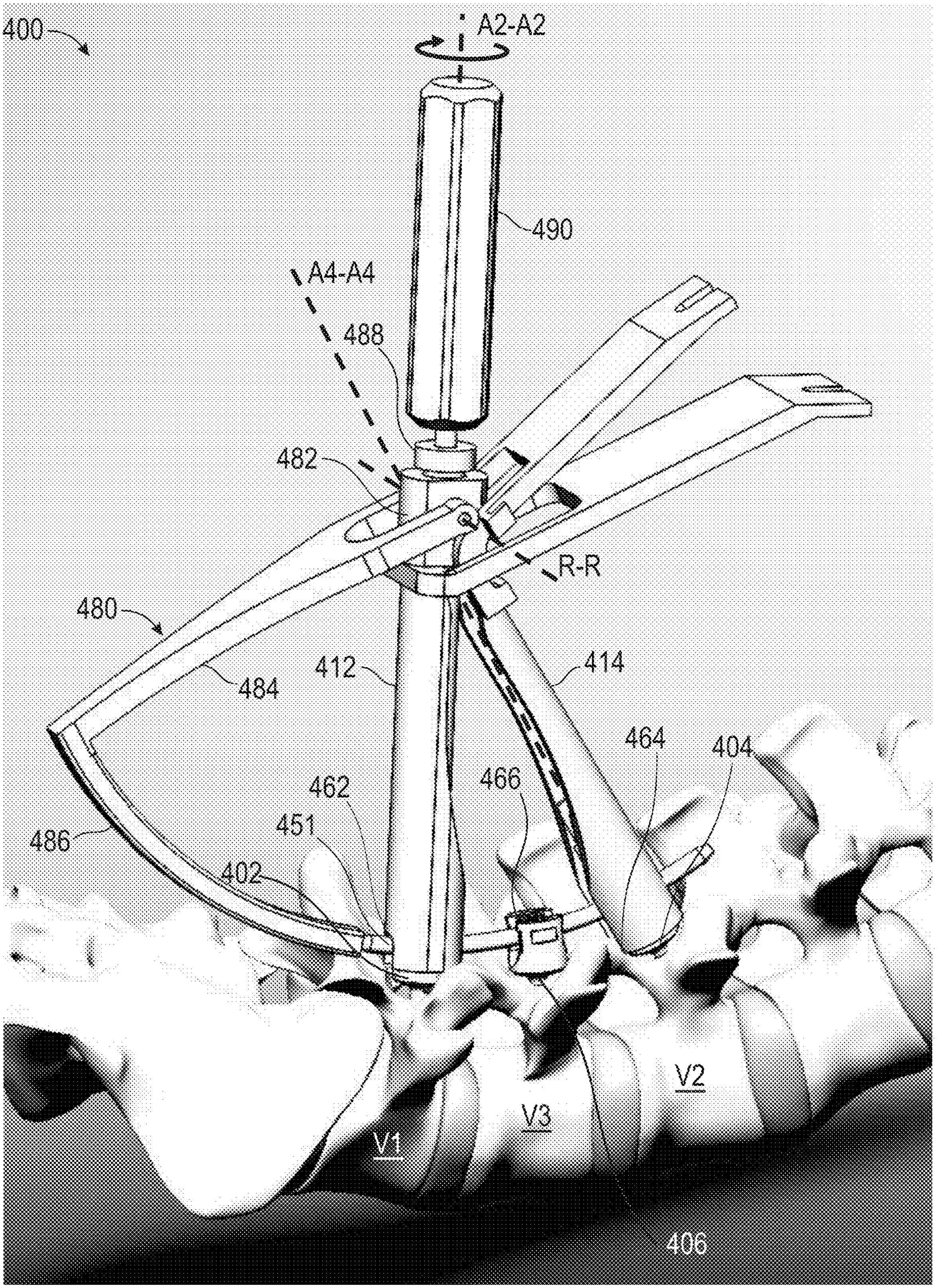

As shown in FIG. 4F, the rod insertion device 480 can be rotated through the seats of the first screw 402, the second screw 404, and the third screw 406 while being coupled to the first tower 412. In some embodiments, the rod insertion device 480 may be transferred to another tower to adjust the arcuate path P for guiding the connection member 451 to the seat of the screw corresponding to the other tower. Transferring the rod insertion device 480 to other towers may assist in guiding a connection member 451 through the seats of all of the screws despite possible misalignment. Accordingly, the system 400 may advantageously adapt to each operation, patient, and position of the screws.

As shown in FIG. 5G, an insert screw may be inserted within a lumen of the insertable support pin 488 and first tower 412 and advanced to the screw head of the first screw 402. A tool 490 can be subsequently advanced through the insertable support pin 488 and the first tower 412 to engage with the insert screw. In some embodiments, the tool 490 may be the same or similar to the tool 390 described above. The tool 490 can be rotated about the first axis A2-A2 of the first tower 412 to advance the insert screw within the screw head of the first screw 402 to secure the connection element 451 to the first screw 402.

Figure 4H:
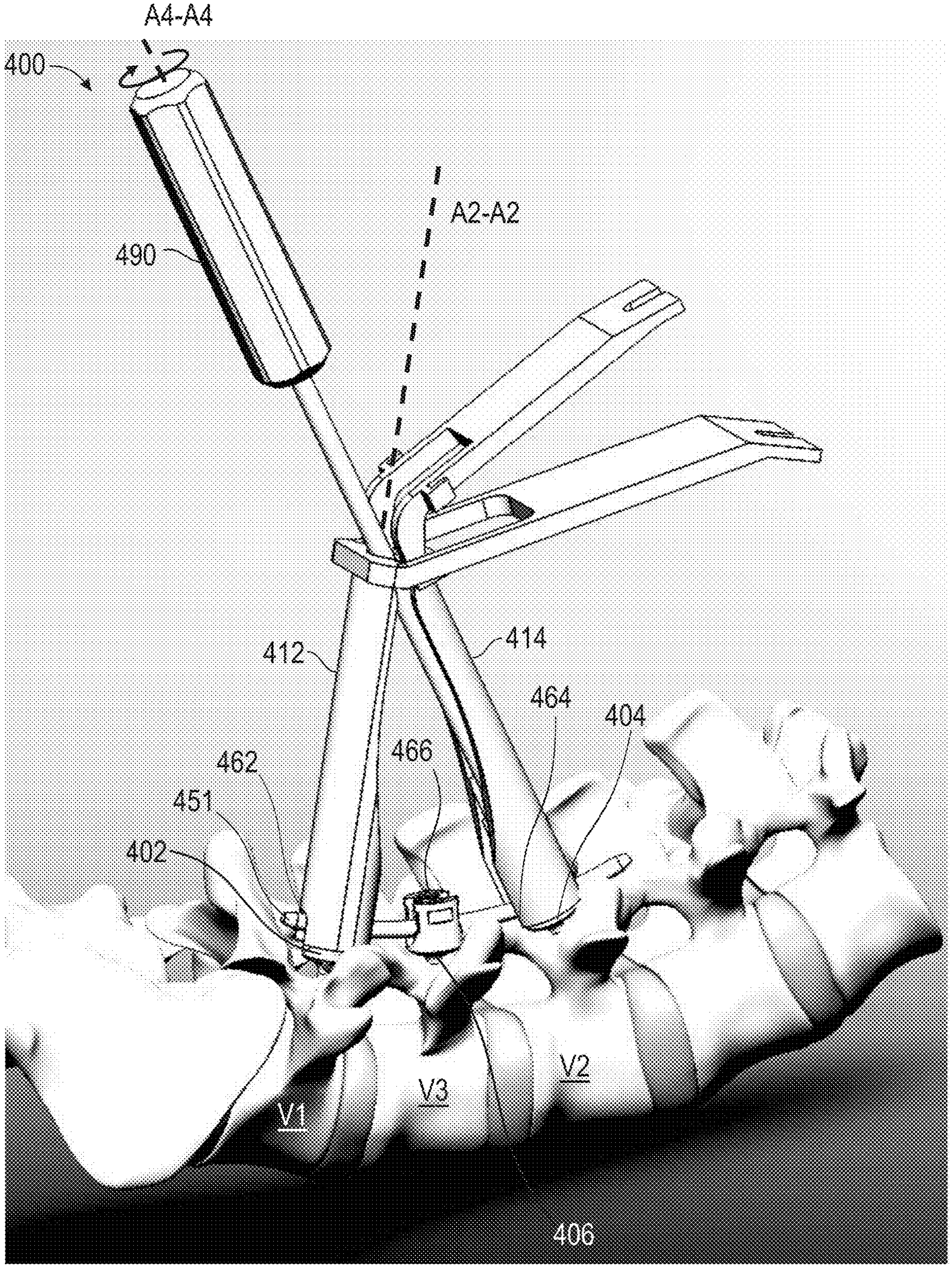

As shown in FIG. 4H, the tool 490 and rod insertion device 480 can be removed from the first tower 412. The tool 490 may subsequently be inserted within a lumen of the second tower 414. An insert screw can be advanced through the second tower 414 prior to advancing the tool 490 through the second tower 414. The tool 490 can engage with an insert screw positioned at the distal end of the second tower 414. The tool 490 can be rotated about the second axis A4-A4 of the second tower 414 to advance the insert screw within the screw head of the second screw 404 to secure the connection element 451 to the second screw 404.

Figure 4I:
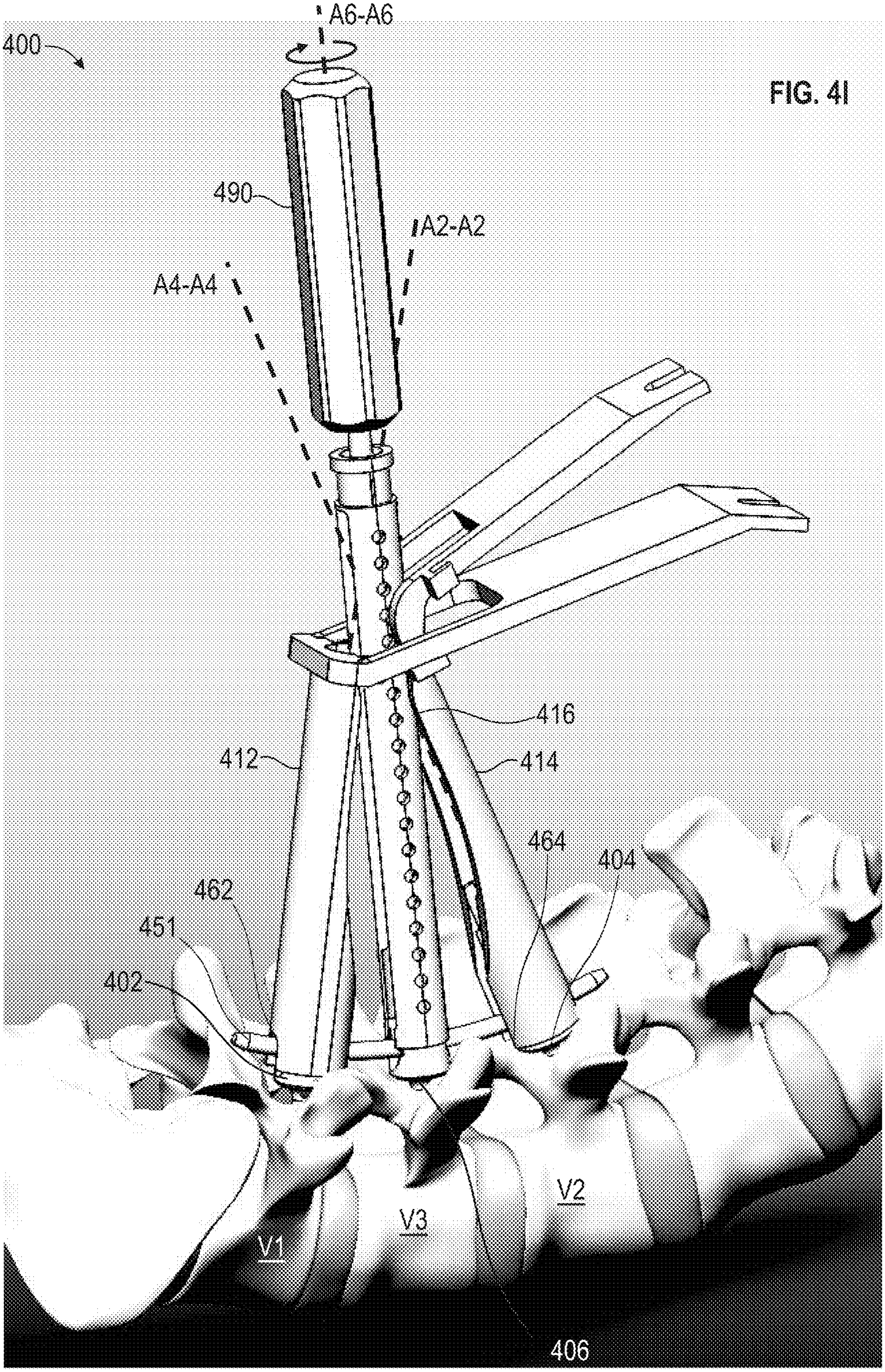

As shown in FIG. 4I, the tool 490 can be removed from the second tower 414 and the third tower 416 can be advanced through the cutouts 424, 444 to engage with the third screw 406. The tool 490 can be subsequently advanced through the lumen of the third tower 416. An insert screw can be advanced through the third tower 416 prior to advancing the tool 490 through the third tower 416. The tool 490 can engage with the insert screw positioned at the distal end of the third tower 416. The tool 490 can be rotated about the third axis A6-A6 of the third tower 416 to advance the insert screw within the screw head of the third screw 406 to secure the connection element 451 to the third screw 406.

Figure 4J:
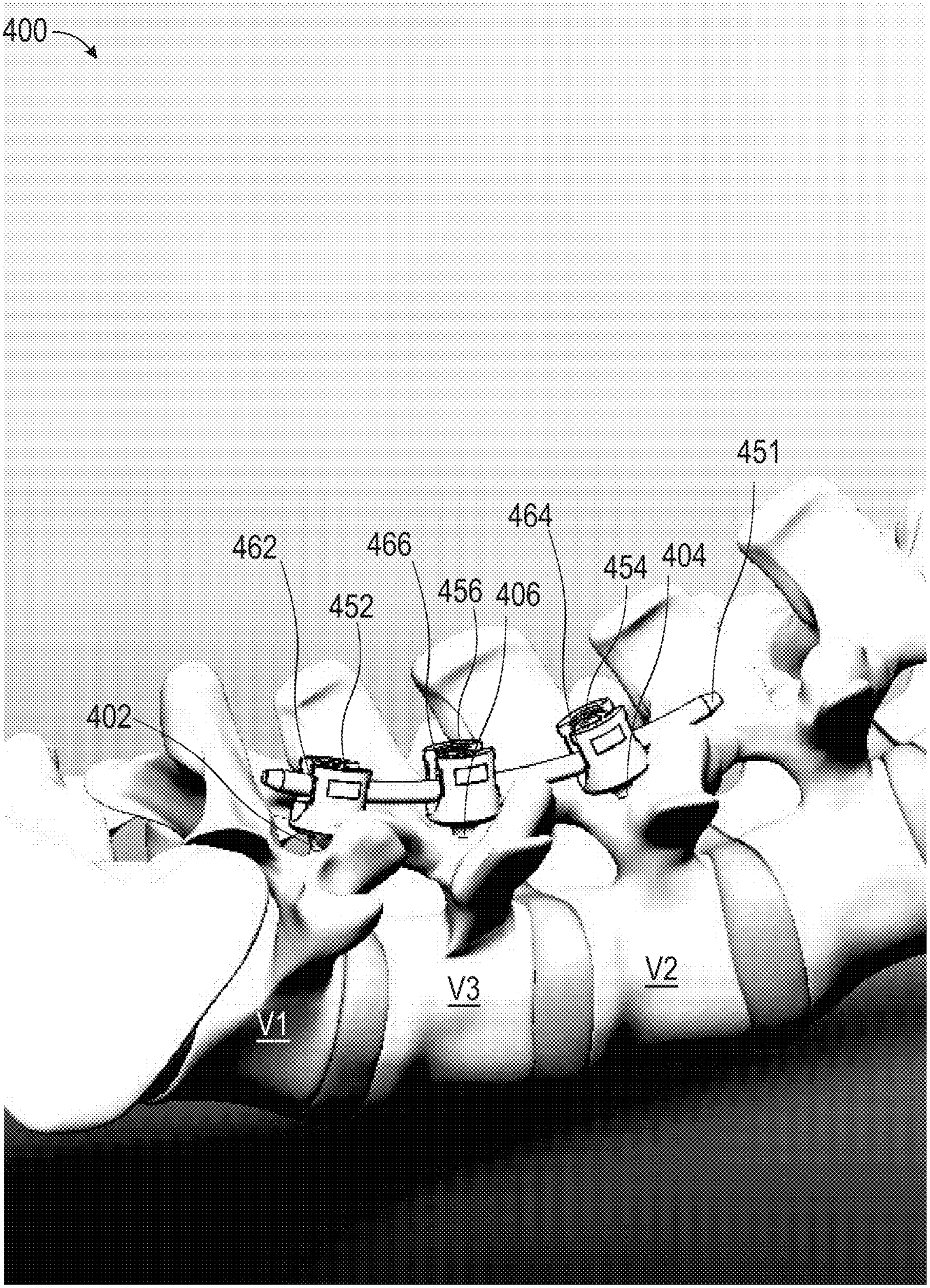

As shown in FIG. 4J, the first screw 402, the second screw 404, the third screw 406, the first insert screw 452, the second insert screw 454, the third insert screw 456, and the connection element 451 can remain attached to the spine after removing the tool 490, the first tower 412, the second tower 414, and the third tower 416. In some embodiments, the tool 490, the first tower 412, the second tower 414, and the third tower 416 can be removed in an inverse order opposite the order of insertion. For example, the tool 490 can be removed first, followed by the third tower 416, the second tower 414, and finally the first tower 412. As further shown in FIG. 4J, the connection element 451 can extend through a screw head of the first screw 402, the second screw 404, and the third screw 406. The first insert screw 452 can be advanced within the screw head of the first screw 402 and presses against the connection element 451. Similarly, the second insert screw 454 and the third insert screw 456 can be advanced within the screw heads of the second screw 404 and the third screw 406, respectively, and press against the connection element 451.

Figure 5:
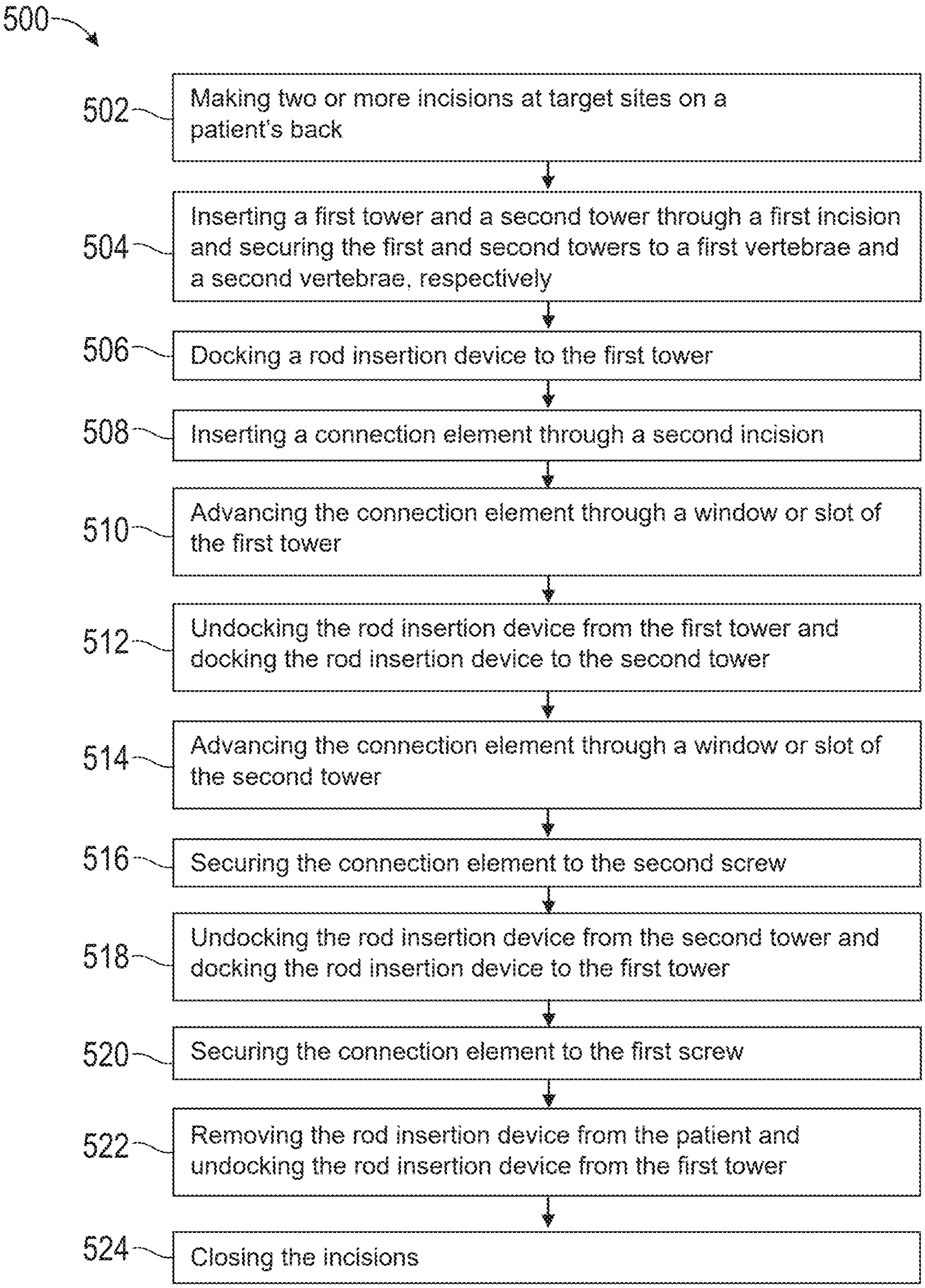
FIG. 5 illustrates a flow chart of a method for stabilizing spinal vertebrae comprising spinal screws.

Systems, Devices and Methods of FIG. 5

FIG. 5 is a flow chart illustrating an embodiment of a method 500 for securing a connection element to a patient's vertebrae. The method 500 may implement the systems 300 or 400 discussed above. The method 500 may be controlled and operated at least in part by a human operator. In some embodiments, a control system or robotic device may assist in controlling or operating at least part of method 500. For example, a control system or robotic device may engage with proximal portions of the towers to control compression or retraction of the distal portions of the towers.

The method 500 begins with step 502 where incisions, or surgical cuts, are made at two or more operating sites on a patient's back. A first incision can be made at or above a position corresponding to one or more target vertebrae. For example, an incision can be made between two adjacent vertebrae. A second incision can be made at a point away from the first incision. In some embodiments, the first and second incisions may be aligned along a longitudinal axis corresponding to a side of the spine of the patient. In some embodiments, the second incision may be separated from the first incision by a distance. In some embodiments, the distance may correspond to the length of a radial member of a rod insertion device. For example, the second incision may be positioned at a length of the radial member from the first incision along the longitudinal axis. In such embodiments, the radial member can rotate about a rotational axis positioned at the skin level of the patient when in an operative state. In some embodiments, the distance may correspond to the height of the body portion and the length of a radial member of the rod insertion device. For example, the second incision may be positioned at a length away from the first incision, wherein the length corresponds to the sine of the angle between the radial member and the body portion of the rod insertion device multiplied by the length of the radial member of the rod insertion device. In such embodiments, the radial member can be at an elevated position from the skin level by the height of the body portion of the rod insertion device.

The method 500 then moves to step 504 in which two or more towers are inserted and secured to the one or more target vertebrae. In some embodiments, each tower can configured to be secured to a distinct vertebra. For example and without limitation, two towers can be configured to secure to a first vertebrae and a second vertebrae, respectively. In some embodiments, a first tower may be inserted through the first incision and secured to a first vertebrae via a first screw positioned at the distal end of the first tower and a second tower may be inserted through the first incision and secured to a second vertebrae via a second screw positioned at the distal end of the second tower. In some embodiments, the second tower may be inserted through a cutout formed through a wall portion of the proximal portion of the first tower. In such embodiments, the first and second towers can both be positioned in a first plane. In some embodiments, the first and second towers may be inserted through the first opening at an angle such that the first and second towers intersect at a pivot point corresponding to a skin level of the first incision.

The method 500 then moves to step 506 in which a rod insertion device couples onto one of the towers. In some embodiments, the rod insertion device can be coupled to the first tower. In some embodiments, the rod insertion device can include a body portion configured to engage with and dock to a platform of the towers. In some embodiments, the platform may be positioned at the skin level of the first incision. The body portion can extend the effective length of the towers by at least a length of the body portion. In some embodiments, the rod insertion device may be the rod insertion device of systems 300, 400 described above. The rod insertion device can be coupled to the first tower by advancing the body portion to the platform of the first tower and inserting an insertable securing pin within a lumen of the body portion extending at least partially into a distal portion of the first tower. The insertable securing pin can include threading to engage with the corresponding threading of the body portion and/or first tower.

The method 500 then moves to step 508 in which the rod insertion device inserts a connection element through the second incision. In some embodiments, a radial member of the rod insertion device may rotate about a rotational axis to advance an arc member of the rod insertion device towards the second incision. The arc member can extend orthogonally from the distal end of the radial member of the rod insertion device. The arc member can engage with and support the connection element. The arc member can have a curvature corresponding to a circumference of a circle defined by a radius of the length of the radial member. Accordingly, as the radial member rotates about a rotational axis, the arc member can advance along a circumferential path intersecting the skin of the patient at the second incision.

The method 500 then moves to step 510 in which the rod insertion device advances the connection element through a window or slot of the first tower such that the connection element is within a seat of the first screw. In some embodiments, the rod insertion device may continue to advance the connection element through a window or slot of the second tower such that the connection element is within a seat of the second screw. In such embodiments, the first and second towers may be properly aligned. In some embodiments, the towers may not be correctly aligned such that the rod insertion device would not properly advance the connection element through the window or slot of the second tower.

The method 500 then moves to step 512 in which the rod insertion device uncouples from the first tower and coupled to the second tower. In some embodiments, the arc member may not be moved and the connection element may remain within the window or slot of the first tower and the seat of the first screw while the body portion is uncoupled from the first tower and coupled to the second tower. Coupling the body portion to the second tower can advantageously aligns a second circumferential path with the second tower such that the second circumferential path intersects the window or slot of the second tower such that the connecting element can be advanced to a seat of the second screw.

The method 500 then moves to step 514 in which the rod insertion device advances the connection element through the window or slot of the second tower such that the connection element is within a seat of the second screw.

The method 500 then moves to step 516 in which the connection element secures to the second screw. An insert screw can be inserted through a lumen of the rod insertion device and second tower and advanced to the screw head of the second screw. In some embodiments, the insert screw may be inserted with a guide and a tool. In some embodiments, the guide and the tool may be separate devices. In some embodiments, the guide and the tool may be a unitary tool. The tool can be inserted through the lumen of the rod insertion device and the second tower to secure the insert screw onto the screw head of the second screw. In some embodiments, the tool may be a screwdriver configured to thread the insert screw onto the screw head of the second screw. Advancing the insert screw distally along the screw head can press against the connection element thereby securing the connection element to the second screw.

The method 500 then moves to step 518 in which the rod insertion device uncouples from the second tower and coupled to the tower. The tool can be removed from the second tower and the body portion can be uncoupled from the second tower and coupled to the first tower.

The method 500 then moves to step 520 in which the connection element secures to the first screw. An insert screw can be inserted through a lumen of the rod insertion device and first tower and advanced to the screw head of the first screw. In some embodiments, the insert screw may be inserted with a guide and the tool. The tool can be inserted through the lumen of the rod insertion device and the second tower to secure the insert screw onto the screw head of the second screw. The tool can advance the insert screw distally along the screw head to press against the connection element thereby securing the connection element to the first screw.

The method 500 then moves to step 522 in which the rod insertion device is removed from the patient and uncouples from the first tower. The radial member can rotate about a rotational axis in a direction opposite the circumferential path to remove the arc member from the patient's back. The rod insertion device can then be uncoupled from the first tower.

The method 500 then moves to step 524 in which the incisions are closed. In some embodiments, a physician may sterilize the surgical site, close the incisions, and dress the wounds.

In some embodiments, steps 512 through 514 may be repeated until the connection element is advanced to a seat of the last screw of the last tower. For example, in some embodiments with three towers, the steps 512 through 514 may be repeated until the connection element extends through all three towers. Similarly, steps 516 through 520 may be repeated until the connection element is secured to all of the screws. Securing the first and second screws one at a time may advantageously allow the connection element to be secured, accessed, or threaded even when not perfectly aligned. Alternatively, the rod insertion device may advance the connection element through at least the first and second screw while coupled to a single tower as described above with respect to system 400.

In some embodiments, the method 500 may further comprise a step of compression retraction to adjust the spacing between the vertebrae by applying forces to a proximal end of the first and second towers.

EXAMPLE CLAUSES

Examples of the implementations of the present disclosure can be described in view of the following example clauses. The features recited in the below example implementations can be combined with additional features disclosed herein. Furthermore, additional inventive combinations of features are disclosed herein, which are not specifically recited in the below example implementations, and which do not include the same features as the specific implementations below. For sake of brevity, the below example implementations do not identify every inventive aspect of this disclosure. The below example implementations are not intended to identify key features or essential features of any subject matter described herein. Any of the example clauses below, or any features of the example clauses, can be combined with any one or more other example clauses, or features of the example clauses or other features of the present disclosure.

Clause 1. A system for stabilizing spinal vertebrae through a skin incision, comprising: a first screw having a first screw head, and a second screw having a second screw head; a first tower having a distal portion, a proximal portion, and a bend between the distal portion and the proximal portion, the first tower being configured to be removably coupled with the first screw at a distal end of the first tower; a second tower having a distal portion and a proximal portion, the second tower configured to be removably coupled with the second screw at a distal end of the second tower; and a rod insertion device comprising a rotating arm, the rod insertion device configured to couple with at least one of the first tower and the second tower such that the rotating arm can rotate about an axis of rotation relative to the first tower and/or the second tower, wherein the rod insertion device is configured to advance a connecting element into the first screw head of the first screw and the second screw head of the second screw.

Clause 2. The system of Clause 1, wherein the rod insertion device is configured to be removably coupled to at least one of the first tower and the second tower.

Clause 3. The system of any one of Clauses 1-2, wherein the rod insertion device is configured to be removably coupled to only one of the first tower or the second tower at a time.

Clause 4. The system of any one of Clauses 1-3, wherein the rod insertion device further comprises a body portion comprising a longitudinal lumen and a transverse lumen, wherein the rotating arm comprises a radial member and an arc member extending from a distal end of the radial member, wherein the rotating arm is rotatably coupled to the body portion about the transverse lumen.

Clause 5. The system of any one of Clauses 1-4, wherein the first tower has an opening therein that is completely enclosed, the opening sized and configured to receive the second tower and at least part of the rod insertion device therein such that, in an operable state, an outer wall of a portion of the first tower surrounds an outer surface of a portion of the second tower and an outer surface of at least part of the rod insertion device.

Clause 6. The system of Clause 5, wherein the opening extends at least through a proximal end of the distal portion of the first tower.

Clause 7. The system of any one of Clauses 1-6, wherein the proximal portion of the first tower is configured such that, in an operable state of the system, the proximal portion of the first tower also extends at an acute, nonzero angle away from a longitudinal centerline of the proximal portion of the second tower so that the proximal portion of the first tower forms an acute angle relative to the proximal portion of the second tower.

Clause 8. The system of any one of Clauses 1-7, wherein the distal portion of the first tower is configured such that, in an operable state of the system, the distal portion of the first tower extends at an acute, nonzero angle away from a longitudinal centerline of the distal portion of the second tower so that the distal portion of the first tower forms an acute angle relative to the distal portion of the second tower.

Clause 9. The system of any one of Clauses 1-8, wherein first tower comprises one or more first longitudinal axes and the second tower comprises one or more second longitudinal axes, wherein, in an operable state of the system, the one or more first longitudinal axes and the one or more second longitudinal axes are coplanar.

Clause 10. The system of any one of Clauses 1-9, wherein, in an operable state of the system, the proximal portion of the first tower extends in the direction of the spine.

Clause 11. The system of any one of Clauses 1-10, wherein, in an operable state of the system, the proximal portion of the first tower is axially displaced from the proximal portion of the second tower in the direction of the spine.

Clause 12. A system for stabilizing spinal vertebrae through a skin incision, comprising: a first screw having a first screw head and a second screw having a second screw head; a first tower having a first outer wall defining a lumen extending along a first longitudinal centerline, and a first opening orthogonal to the first longitudinal centerline, the opening positioned at a proximal end of the first outer wall, the first tower configured to be removably coupled with the first screw at a distal end of the first tower; a second tower having a second outer wall defining a lumen extending along a second longitudinal centerline, and a second opening orthogonal to the second longitudinal centerline, the second opening positioned at a proximal end of the second outer wall, the second tower configured to be removably coupled with the second screw at a distal end of the second tower; and a rod insertion device comprising: a body portion configured to be removably coupled to at least one of the first tower and the second tower, the body portion comprising a longitudinal lumen and a transverse lumen orthogonal to the longitudinal lumen; a rotating member configured to be rotatably coupled to the body portion about the transverse lumen; an arc member extending from a distal end of the rotating member opposite the body portion, the arc member configured to removably support a connection rod; and an insertable support pin configured to be removably inserted through the longitudinal lumen of the body portion and into the lumen of at least one of the first tower and the second tower; wherein: the rod insertion device is configured to advance the connection rod to at least the first screw and the second screw; and the longitudinal lumen is configured to be coaxial with at least one of the first longitudinal centerline or the second longitudinal centerline.

Clause 13. The system of Clause 12, wherein: the first tower further comprises a first distal portion defining the first outer wall and a first proximal portion extending from a proximal end of the first distal portion, wherein the first opening is positioned at the proximal end of the first distal portion; and the second tower further comprises a second distal portion defining the second outer wall and a second proximal portion extending from a proximal end of the second distal portion, wherein the second opening is positioned at the proximal end of the second distal portion.

Clause 14. The system of Clause 13, wherein: the first proximal portion extends at an acute, nonzero angle away from the first longitudinal centerline of the first distal portion; the second proximal portion extends at an acute, nonzero angle away from the second longitudinal centerline of the second distal portion.

Clause 15. The system of any one of Clauses 12-14, wherein first longitudinal centerline and the second longitudinal centerline are coplanar.

Clause 16. The system of any one of Clauses 1-15, wherein, in an operable state, the first tower and the second tower are configured to intersect in an operable state at or adjacent to a skin level of a patient such that a distance from the skin level to a proximal most end of the distal portion of the first tower is less than or equal to 10% of a length of the distal portion of the first tower and a distance from the skin level to a proximal most end of the distal portion of the second tower is less than or equal to 10% of a length of the distal portion of the second tower.

Clause 17. A method of stabilizing spinal vertebrae, comprising: implanting two or more screws coupled with a corresponding one of two or more towers through an incision into a corresponding vertebra; aligning a longitudinal lumen of a body portion of a rod insertion device with a longitudinal centerline of at least one of the two or more towers; inserting an insertion support pin through the longitudinal lumen and into a lumen defined by an outer wall of the at least one of the two or more towers; moving a first tower of the two or more towers relative to a second tower of the two or more towers to move a first vertebra from a first position relative to a second vertebra to a second position relative to the second vertebra; and advancing a connecting element toward the two or more screws; and securing the connecting element to at least one of the two or more screws to prevent the first vertebra from moving back to the first position relative to the second vertebra.

Clause 18. The method of Clauses 17, wherein implanting two or more screws coupled with a corresponding tower through an incision into a corresponding vertebra comprises: inserting a first screw that is coupled with the first tower through an incision into the first vertebra; advancing the second tower that is coupled with a second screw through an opening formed in the first tower and implanting the second screw into the second vertebra.

Clause 19. The method of any one of Clauses 17-18, wherein advancing the connecting element toward the two or more screws comprises rotating a radial arm of the rod insertion device about a transverse lumen, wherein an arc member extending from a distal end of the radial arm follows an arcuate path to the two or more screws.

Clause 20. The method of any one of Clauses 17-19 further comprising: retracting the insertion support pin from the at least one of the two or more towers after the connecting element is advanced past a first screw of the two or more screws; aligning the longitudinal lumen of the body portion of the rod insertion device with a longitudinal centerline of another one of the two or more towers; inserting the insertion support pin through the longitudinal lumen and into a lumen defined by an outer wall of another one of the two or more towers; and advancing the connecting element toward a second one of the two or more screws.

Clause 21. The method of any one of Clauses 17-20 wherein the two or more towers comprises: a first tower having a proximal portion, a distal portion, and a bend between the proximal portion of the first tower and the distal portion of the first tower such that an axial centerline of the proximal portion of the first tower is at an acute angle relative to an axial centerline of the distal portion of the first tower. A second tower having a proximal portion, a distal portion, and a bend between the proximal portion of the second tower and the distal portion of the second tower such that an axial centerline of the proximal portion of the second tower is at an acute angle relative to an axial centerline of the distal portion of the second tower.

Clause 22. A method of stabilizing spinal vertebrae, comprising: implanting a first screw that is coupled with a first tower through an incision into a first vertebra; advancing a second tower that is coupled with a second screw through an opening formed in the first tower and implanting the second screw into a second vertebra; coupling a rod insertion device to at least one of the first tower or the second tower; moving a proximal portion of the first tower relative to a proximal portion of the second tower to move the first vertebra from a first position relative to the second vertebra to a second position relative to the second vertebra; and advancing a connecting element toward the first screw and the second screw; and securing the connecting element to at least one of the first screw and the second screw to prevent the first vertebra from moving back to the first position relative to the second vertebra; wherein the first tower has a proximal portion, a distal portion, and a bend between the proximal portion of the first tower and the distal portion of the first tower such that an axial centerline of the proximal portion of the first tower is at an acute angle relative to an axial centerline of the distal portion of the first tower, wherein the second tower has a proximal portion, a distal portion, and a bend between the proximal portion of the second tower and the distal portion of the second tower such that an axial centerline of the proximal portion of the second tower is at an acute angle relative to an axial centerline of the distal portion of the second tower.

Clause 23. A method of stabilizing spinal vertebrae, comprising: implanting a first screw that is coupled with a first extension through a single incision into a first vertebra, the first extension having a proximal portion and a distal portion; advancing a second extension that is coupled with a second screw through the single incision and through a first opening formed in the first extension so that an axial centerline of at least a distal portion of the second extension is at an acute angle relative to an axial centerline of at least the distal portion of the first extension; implanting the second screw into a second vertebra; coupling a rod insertion device onto at least one of a first tower or a second tower; and advancing the rod insertion device toward the first screw and the second screw.

Clause 24. The system of Clause 1, further comprising a third tower having a distal portion, a proximal portion, and a bend between the distal portion and the proximal portion, the third tower being configured to be removably coupled with a third screw at a distal end of the third tower.

Clause 25. The system of Clause 1, wherein the rod insertion device further comprises a body portion, a radial member rotatably coupled to the body portion, and an arc member extending from the radial member.

Clause 26. The system of Clause 24, wherein the third tower is configured to removably couple with the third screw such that, when the third tower is coupled with the third screw, an axial centerline of the distal portion of the third tower is approximately collinear with an axial centerline of the third screw; the proximal portion of the first tower extends at an acute, nonzero angle away from the axial centerline of the distal portion of the first tower; the proximal portion of the third tower extends at an acute, nonzero angle away from the axial centerline of the distal portion of the third tower; and in an operable state, the first tower, the second tower, and the third tower are configured to intersect one another.

Clause 27. The system of Clause 24, wherein, in an operable state, the proximal portion of the third tower is positioned between the proximal portion of the first tower and the second tower.

Clause 28. The system of Clause 24, wherein the second tower has an opening formed through a wall portion of the second tower, the opening being configured to allow the third tower to pass through the opening of the second tower in an operable state and such that at least a portion of a wall of the second tower at least partially surrounds an outside surface of the third tower.

Clause 29. The method of Clause 23, further comprising a third screw having a third screw head and a third tower having a distal portion and a proximal portion, the third tower being configured to be removably coupled with the third screw at a distal end of the third tower.

Clause 30. The method of Clause 23, wherein a third tower is configured to removably couple with a third screw such that, when the third tower is coupled with the third screw, an axial centerline of the distal portion of the third tower is approximately collinear with an axial centerline of the third screw.

Clause 31. The method of Clause 23, further comprising advancing a third tower that is coupled with a third screw through an opening formed in the first tower and implanting the third screw into a third vertebra.

Clause 32. The method of Clause 30, further comprising advancing a connecting element toward the third screw and securing the connecting element to the third screw to prevent the first vertebra from moving back to a first position relative to a third vertebra.

Clause 33. A method of stabilizing spinal vertebrae, comprising: implanting a first screw that is coupled with a first tower through an incision into a first vertebra; advancing a second tower that is coupled with a second screw through a cutout formed in the first tower and implanting the second screw into a second vertebra; coupling a rod insertion device to the first tower; advancing a connection element through a first window of the first tower; uncoupling the rod insertion device from the first tower and coupling the rod insertion device to the second tower; advancing the connection element through a second window of the second tower; securing the connection element to the second screw; uncoupling the rod insertion device from the second tower and coupling the rod insertion device to the first tower; and securing the connection element to the first screw.

Clause 34. The method of Clause 33, further comprising coupling a rigid connector element with the first screw and the second screw to generally fix a position of the first screw relative to the second screw and a third screw.

Clause 35. The method of Clause 33, further comprising removing the rod insertion device from the patient and uncoupling the rod insertion device from the first tower.

Clause 36. The system of Clause 1, wherein: the first tower is configured to removably couple with the first screw such that, when the first tower is coupled with the first screw, an axial centerline of the distal portion of the first tower is approximately collinear with an axial centerline of the first screw; the second tower is configured to removably couple with the second screw such that, when the second tower is coupled with the second screw, an axial centerline of the distal portion of the second tower is approximately collinear with an axial centerline of the second screw; and the rod insertion device is configured to dock to or couple to at least one of the first tower and the second tower.

Clause 37. The system of Clause 36, wherein the first tower is configured to removably couple with the first screw such that, when the first tower is coupled with the first screw, an axial centerline of the distal portion of the first tower is approximately collinear with an axial centerline of the first screw; and the second tower is configured to removably couple with the second screw such that, when the second tower is coupled with the second screw, an axial centerline of the distal portion of the second tower is approximately collinear with an axial centerline of the second screw.

Clause 38. The system of Clause 37, further comprising a third tower, wherein: in an operable state, the proximal portion of the first tower extends away from the third tower in a first direction; and in an operable state, the proximal portion of the second tower also extends away from the third tower in the first direction.

Clause 39. A system for stabilizing spinal vertebrae through a skin incision, comprising: a first screw having a first screw head, a second screw having a second screw head, and a third screw having a third screw head; a first tower having a distal portion, a proximal portion, and a bend between the distal portion and the proximal portion, the first tower being configured to be removably coupled with the first screw at a distal end of the first tower; a second tower having a distal portion and a proximal portion, the second tower configured to be removably coupled with the second screw at a distal end of the second tower; a rod insertion device comprising a rotating arm configured to couple with at least one of the first tower and the second tower such that the rotating arm can rotate about an axis of rotation relative to the first tower and/or the second tower; and an interface member removably coupled with the rod insertion device at a distal end of the rod insertion device, wherein the interface member is configured to couple with a proximal end of a connecting element into the first screw head of the first screw and the second screw head of the second screw.

Clause 40. The system of Clause 39 wherein the interface member has a recess in an end thereof that is configured to releasably receive the proximal end of the connecting element.

Clause 41. The system of Clause 1, wherein the first tower has an opening therein that is completely enclosed, wherein the second tower and at least part of the rod insertion device are received within the opening in an operable state of the system such that an outer wall of a portion of the first tower surrounds an outer surface of a portion of the second tower and an outer surface of at least part of the rod insertion device.

Clause 42. The system of Clause 1, wherein the first tower comprises one or more longitudinal axes that extend axially through a portion of the first tower and the second tower comprises one or more longitudinal axes that extend axially through a portion of the second tower, wherein, in an operable state of the system, the one or more longitudinal axes that extend axially through a portion of the first tower and the one or more longitudinal axes that extend axially through a portion of the second tower are coplanar.

Clause 43. The system of Clause 12, wherein: the first tower further comprises a first distal portion defining the first outer wall and a first proximal portion adjacent to the first distal portion, wherein the first opening is positioned at the proximal end of the first distal portion; and the second tower further comprises a second distal portion defining the second outer wall and a second proximal portion adjacent to the second distal portion, wherein the second opening is positioned at the proximal end of the second distal portion.

Any of the embodiments of the system or systems disclosed below can have any of the screws, towers, or guide elements, or other components, features, and/or other details of any other embodiments of the implant systems disclosed herein or which are disclosed in US Patent Publication No. 2022-0361922 A1 or components thereof, which patent is included herein in Appendix A and is incorporated by reference herein as if fully set forth herein, in place of or in any combination with any of the components, features, and/or other details disclosed herein for the embodiments of the system or systems disclosed below. Additionally, any of the steps, sequences of steps, or procedures described above with respect to any other system embodiments or which are disclosed in US Patent Publication No. 2022-031922A1, which is included herein in Appendix A, can be used in place of or in any combination with any of the steps, sequences of steps, or procedures described below for any of the embodiments of the systems disclosed below to form new steps, sequences of steps, and procedures for the embodiments of the system disclosed below.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present embodiments is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as “can,” “could,” “might,” or “may,” unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15°, 10°, 5°, 3°, 1°, or 0.1°.

Further, the ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example±10%). For example, "about 7 mm" includes "7 mm" and numbers and ranges preceded by a term such as "about" or "approximately" should be interpreted as disclosing numbers and ranges with or without such a term such that this application supports claiming the number and ranges disclosed in the specification and/or claims with or without the term such as "about" or "approximately" before such numbers or ranges. Phrases preceded by a term such as "substantially" include the recited phrase and should be interpreted based on the circumstances (e.g., as much as reasonably possible under the circumstances). For example, "substantially straight" includes "straight."

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for stabilizing spinal vertebrae through a skin incision, comprising:

a first screw having a first screw head, and a second screw having a second screw head;

a first tower having a distal portion, a proximal portion, and a bend between the distal portion and the proximal portion, the first tower being configured to be removably coupled with the first screw at a distal end of the first tower;

a second tower having a distal portion and a proximal portion, the second tower configured to be removably coupled with the second screw at a distal end of the second tower; and a rod insertion device comprising a rotating arm, the rod insertion device configured to couple with at least one of the first tower and the second tower such that the rotating arm can rotate about an axis of rotation relative to the first tower and/or the second tower, wherein the rod insertion device is configured to advance a connecting element into the first screw head of the first screw and the second screw head of the second screw;

wherein the first tower has an opening therein that is completely enclosed, wherein the second tower and at least part of the rod insertion device are received within the opening in an operable state of the system such that an outer wall of a portion of the first tower surrounds an outer surface of a portion of the second tower and an outer surface of at least part of the rod insertion device.

2. The system of claim 1, wherein the rod insertion device is configured to be removably coupled to at least one of the first tower and the second tower.

3. The system of claim 2, wherein the rod insertion device is configured to be removably coupled to only one of the first tower or the second tower at a time.

4. The system of claim 1, wherein the rod insertion device further comprises a body portion comprising a longitudinal lumen and a transverse lumen, wherein the rotating arm comprises a radial member and an arc member extending from a distal end of the radial member, wherein the rotating arm is rotatably coupled to the body portion about the transverse lumen.

5. The system of claim 1, wherein the opening extends at least through a proximal end of the distal portion of the first tower.

6. The system of claim 1, wherein the proximal portion of the first tower is configured such that, in an operable state of the system, the proximal portion of the first tower also extends at an acute, nonzero angle away from a longitudinal centerline of the proximal portion of the second tower so that the proximal portion of the first tower forms an acute angle relative to the proximal portion of the second tower.

7. The system of claim 1, wherein the distal portion of the first tower is configured such that, in an operable state of the system, the distal portion of the first tower extends at an acute, nonzero angle away from a longitudinal centerline of the distal portion of the second tower so that the distal portion of the first tower forms an acute angle relative to the distal portion of the second tower.

8. The system of claim 1, wherein the first tower comprises one or more longitudinal axes that extend axially through a portion of the first tower and the second tower comprises one or more longitudinal axes that extend axially through a portion of the second tower, wherein, in an operable state of the system, the one or more longitudinal axes that extend axially through a portion of the first tower and the one or more longitudinal axes that extend axially through a portion of the second tower are coplanar.

9. The system of claim 1, wherein, in an operable state of the system, the proximal portion of the first tower extends in the direction of the spine.

10. The system of claim 1, wherein, in an operable state of the system, the proximal portion of the first tower is axially displaced from the proximal portion of the second tower in the direction of the spine.

11. A system for stabilizing spinal vertebrae through a skin incision, comprising:

a first screw having a first screw head and a second screw having a second screw head;

a first tower having a first outer wall defining a lumen extending along a first longitudinal centerline, and a first opening orthogonal to the first longitudinal centerline, the opening positioned at a proximal end of the first outer wall, the first tower configured to be removably coupled with the first screw at a distal end of the first tower;

a second tower having a second outer wall defining a lumen extending along a second longitudinal centerline, and a second opening orthogonal to the second longitudinal centerline, the second opening positioned at a proximal end of the second outer wall, the second tower configured to be removably coupled with the second screw at a distal end of the second tower; and a rod insertion device comprising:

a body portion configured to be removably coupled to at least one of the first tower and the second tower, the body portion comprising a longitudinal lumen and a transverse lumen orthogonal to the longitudinal lumen;

a rotating member configured to be rotatably coupled to the body portion about the transverse lumen;

an arc member extending from a distal end of the rotating member opposite the body portion, the arc member configured to removably support a connection rod; and an insertable support pin configured to be removably inserted through the longitudinal lumen of the body portion and into the lumen of at least one of the first tower and the second tower;

wherein:

the rod insertion device is configured to advance the connection rod to at least the first screw and the second screw; and the longitudinal lumen is configured to be coaxial with at least one of the first longitudinal centerline or the second longitudinal centerline.

12. The system of claim 11, wherein:

the first tower further comprises a first distal portion defining the first outer wall and a first proximal portion adjacent to the first distal portion, wherein the first opening is positioned at the proximal end of the first distal portion; and the second tower further comprises a second distal portion defining the second outer wall and a second proximal portion adjacent to the second distal portion, wherein the second opening is positioned at the proximal end of the second distal portion.

13. The system of claim 12, wherein:

the first proximal portion extends at an acute, nonzero angle away from the first longitudinal centerline of the first distal portion;

the second proximal portion extends at an acute, nonzero angle away from the second longitudinal centerline of the second distal portion.

14. The system of claim 11, wherein first longitudinal centerline and the second longitudinal centerline are coplanar.

15. A method of stabilizing spinal vertebrae, comprising:

implanting two or more screws coupled with a corresponding one of two or more towers through an incision into a corresponding vertebra, wherein a first screw of the two or more screws comprises a first screw head and a second screw of the two or more screws comprises a second screw head, wherein a first tower of the two or more towers comprises a distal portion, a proximal portion, a bend between the distal portion and the proximal portion, and an opening therein that is completely enclosed, wherein the first tower is configured to be removably coupled with the first screw at a distal end of the first tower, and a second tower of the two or more towers comprises a distal portion and a proximal portion, wherein the second tower is configured to be removably coupled with the second screw at a distal end of the second tower, and wherein the second tower is received within the opening of the first tower in an operable state such that an outer wall of a portion of the first tower surrounds an outer surface of a portion of the second tower;

aligning a longitudinal lumen of a body portion of a rod insertion device with a longitudinal centerline of at least one of the two or more towers, wherein the rod insertion device comprises a rotating arm that can rotate about an axis of rotation relative to at least one of the two or more towers;

positioning at least a portion of the rod insertion device into the opening of the first tower in the operable state such that the outer wall of the portion of the first tower surrounds an outer surface of at least the portion of the rod insertion device;

inserting an insertion support pin through the longitudinal lumen and into a lumen defined by an outer wall of the at least one of the two or more towers, wherein the outer wall of the portion of the first tower surrounds an outer surface of the insertion support pin;

moving a first tower of the two or more towers relative to a second tower of the two or more towers to move a first vertebra from a first position relative to a second vertebra to a second position relative to the second vertebra; and advancing a connecting element toward the two or more screws and into the first screw head of the first screw and the second screw head of the second screw with the rotating arm of the rod insertion device; and securing the connecting element to at least one of the two or more screws to prevent the first vertebra from moving back to the first position relative to the second vertebra.

16. The method of claim 15, wherein implanting two or more screws coupled with a corresponding tower through an incision into a corresponding vertebra comprises:

inserting the first screw that is coupled with the first tower through an incision into the first vertebra;

advancing the second tower that is coupled with the second screw through the opening formed in the first tower and implanting the second screw into the second vertebra.

17. The method of claim 15, wherein advancing the connecting element toward the two or more screws comprises rotating the rotating arm of the rod insertion device about a transverse lumen, wherein an arc member extending from a distal end of the rotating arm follows an arcuate path to the two or more screws.

18. The method of claim 17 further comprising:

retracting the insertion support pin from the at least one of the two or more towers after the connecting element is advanced past the first screw of the two or more screws;

aligning the longitudinal lumen of the body portion of the rod insertion device with a longitudinal centerline of another one of the two or more towers;

inserting the insertion support pin through the longitudinal lumen and into a lumen defined by an outer wall of the other one of the two or more towers; and advancing the connecting element toward the second screw of the two or more screws.

19. The method of claim 15 wherein an axial centerline of the proximal portion of the first tower is at an acute angle relative to an axial centerline of the distal portion of the first tower; and the second tower further comprises a bend between the proximal portion of the second tower and the distal portion of the second tower such that an axial centerline of the proximal portion of the second tower is at an acute angle relative to an axial centerline of the distal portion of the second tower.

* * * * *